United States Patent
Hull et al.

(10) Patent No.: US 12,357,195 B2
(45) Date of Patent: Jul. 15, 2025

(54) SYSTEM, METHOD AND APPARATUS FOR ANCHORING AN ELECTRONIC DEVICE AND MEASURING A JOINT ANGLE

(71) Applicant: ROM Technologies, Inc., Brookfield, CT (US)

(72) Inventors: Gordon J. Hull, Las Vegas, NV (US); Steven Mason, Las Vegas, NV (US); Bill McGrail, Las Vegas, NV (US); David Scheck, Las Vegas, NV (US); Daniel Lipszyc, Glasgow, MT (US); Mikael Taveras, Boston, MA (US); S. Adam Hacking, Nashua, NH (US); Sucheta Tamragouri, Nashua, NH (US); Jeff Cote, Woodbury, CT (US)

(73) Assignee: ROM Technologies, Inc., Brookfield, CT (US)

( * ) Notice: Subject to any disclaimer, the term of this patent is extended or adjusted under 35 U.S.C. 154(b) by 170 days.

(21) Appl. No.: 18/003,213

(22) PCT Filed: Jun. 23, 2021

(86) PCT No.: PCT/US2021/038617
§ 371 (c)(1),
(2) Date: Dec. 23, 2022

(87) PCT Pub. No.: WO2021/262809
PCT Pub. Date: Dec. 30, 2021

(65) Prior Publication Data
US 2023/0263428 A1 Aug. 24, 2023

Related U.S. Application Data

(60) Provisional application No. 63/123,301, filed on Dec. 9, 2020, provisional application No. 63/044,625, filed on Jun. 26, 2020.

(51) Int. Cl.
*A61B 5/107* (2006.01)
*A61B 90/00* (2016.01)

(52) U.S. Cl.
CPC ............ *A61B 5/1071* (2013.01); *A61B 90/39* (2016.02); *A61B 2090/3937* (2016.02)

(58) Field of Classification Search
CPC .................. A61B 5/1071; A61B 90/39; A61B 2090/3937; A61B 5/6811; A61B 5/6812; A61B 5/6828; A61B 5/6833
See application file for complete search history.

(56) References Cited

U.S. PATENT DOCUMENTS

| 823,712 A | 6/1906 | Uhlmann |
| 4,499,900 A | 2/1985 | Petrofsky et al. |

(Continued)

FOREIGN PATENT DOCUMENTS

| CA | 3193419 A1 | 3/2022 |
| CN | 2885238 Y | 4/2007 |

(Continued)

OTHER PUBLICATIONS

Jennifer Bresnick, "What is the Role of Natural Language Processing in Healthcare?", pp. 1-7, published Aug. 18, 2016, retrieved on Feb. 1, 2022 from https://healthitanalytics.com/ featu res/what-is-the-role-of-natural-language-processing-in-healthcare.

(Continued)

*Primary Examiner* — Timothy P Graves
(74) *Attorney, Agent, or Firm* — Dickinson Wright PLLC; Jonathan H. Harder; Stephen A. Mason

(57) ABSTRACT

A system and method for installing devices on a user can include an indicator set comprising a marker to place markings on the user, and a set of adhesive pads to be placed on the user. A knee pivot anchor can be attached to the user. A template having a proximal portion can be pivotally (Continued)

mounted to the knee pivot anchor. A distal portion of the template can be positioned at different locations on the user. The template also can have an aperture. A set of pods can be interchangeably located in the aperture of the template. Each pod can be secured to respective locations on the user. The template and the knee pivot anchor can be removed from the user with the pods remaining in place on the user to support a goniometer.

20 Claims, 40 Drawing Sheets

(56) References Cited

U.S. PATENT DOCUMENTS

| | | |
|---|---|---|
| 4,822,032 A | 4/1989 | Whitmore et al. |
| 4,869,497 A | 9/1989 | Stewart et al. |
| 4,932,650 A | 6/1990 | Bingham et al. |
| 5,137,501 A | 8/1992 | Mertesdorf |
| 5,161,430 A | 11/1992 | Febey |
| 5,202,794 A | 4/1993 | Schnee et al. |
| 5,240,417 A | 8/1993 | Smithson et al. |
| 5,247,853 A | 9/1993 | Dalebout |
| 5,256,117 A | 10/1993 | Potts et al. |
| D342,299 S | 12/1993 | Birrell et al. |
| 5,282,748 A | 2/1994 | Little |
| 5,284,131 A | 2/1994 | Gray |
| 5,316,532 A | 5/1994 | Butler |
| 5,318,487 A | 6/1994 | Golen |
| 5,324,241 A | 6/1994 | Artigues et al. |
| 5,336,147 A | 8/1994 | Sweeney, III |
| 5,338,272 A | 8/1994 | Sweeney, III |
| 5,356,356 A | 10/1994 | Hildebrandt |
| 5,361,649 A | 11/1994 | Slocum, Jr. |
| D359,777 S | 6/1995 | Hildebrandt |
| 5,429,140 A | 7/1995 | Burdea et al. |
| 5,458,022 A | 10/1995 | Mattfeld et al. |
| 5,487,713 A | 1/1996 | Butler |
| 5,566,589 A | 10/1996 | Buck |
| 5,580,338 A | 12/1996 | Scelta et al. |
| 5,676,349 A | 10/1997 | Wilson |
| 5,685,804 A | 11/1997 | Whan-Tong et al. |
| 5,738,636 A | 4/1998 | Saringer et al. |
| 5,860,941 A | 1/1999 | Saringer et al. |
| 5,950,813 A | 9/1999 | Hoskins et al. |
| 6,007,459 A | 12/1999 | Burgess |
| D421,075 S | 2/2000 | Hildebrandt |
| 6,053,847 A | 4/2000 | Stearns et al. |
| 6,077,201 A | 6/2000 | Cheng |
| 6,102,834 A | 8/2000 | Chen |
| 6,110,130 A | 8/2000 | Kramer |
| 6,155,958 A | 12/2000 | Goldberg |
| 6,162,189 A | 12/2000 | Girone et al. |
| 6,182,029 B1 | 1/2001 | Friedman |
| D438,580 S | 3/2001 | Shaw |
| 6,253,638 B1 | 7/2001 | Bermudez |
| 6,267,735 B1 | 7/2001 | Blanchard et al. |
| 6,273,863 B1 | 8/2001 | Avni et al. |
| D450,100 S | 11/2001 | Hsu |
| D450,101 S | 11/2001 | Hsu |
| D451,972 S | 12/2001 | Easley |
| D452,285 S | 12/2001 | Easley |
| D454,605 S | 3/2002 | Lee |
| 6,371,891 B1 | 4/2002 | Speas |
| D459,776 S | 7/2002 | Lee |
| 6,413,190 B1 | 7/2002 | Wood et al. |
| 6,430,436 B1 | 8/2002 | Richter |
| 6,436,058 B1 | 8/2002 | Krahner et al. |
| 6,450,923 B1 | 9/2002 | Vatti |
| 6,474,193 B1 | 11/2002 | Farney |
| 6,491,649 B1 | 12/2002 | Ombrellaro |
| 6,514,085 B2 | 2/2003 | Slattery et al. |
| 6,535,861 B1 | 3/2003 | OConnor et al. |
| 6,543,309 B2 | 4/2003 | Heim |
| 6,589,139 B1 | 7/2003 | Butterworth |
| 6,601,016 B1 | 7/2003 | Brown et al. |
| 6,602,191 B2 | 8/2003 | Quy |
| 6,613,000 B1 | 9/2003 | Reinkensmeyer et al. |
| 6,626,800 B1 | 9/2003 | Casler |
| 6,626,805 B1 | 9/2003 | Lightbody |
| 6,640,122 B2 | 10/2003 | Manoli |
| 6,640,662 B1 | 11/2003 | Baxter |
| 6,652,425 B1 | 11/2003 | Martin et al. |
| 6,820,517 B1 | 11/2004 | Farney |
| 6,865,969 B2 | 3/2005 | Stevens |
| 6,890,312 B1 | 5/2005 | Priester et al. |
| 6,895,834 B1 | 5/2005 | Baatz |
| 6,902,513 B1 | 6/2005 | McClure |
| 7,058,453 B2 | 6/2006 | Nelson et al. |
| 7,063,643 B2 | 6/2006 | Arai |
| 7,156,665 B1 | 1/2007 | OConnor et al. |
| 7,156,780 B1 | 1/2007 | Fuchs et al. |
| 7,169,085 B1 | 1/2007 | Killin et al. |
| 7,204,788 B2 | 4/2007 | Andrews |
| 7,209,886 B2 | 4/2007 | Kimmel |
| 7,226,394 B2 | 6/2007 | Johnson |
| RE39,904 E | 10/2007 | Lee |
| 7,406,003 B2 | 7/2008 | Burkhardt et al. |
| 7,507,188 B2 | 3/2009 | Nurre |
| 7,594,879 B2 | 9/2009 | Johnson |
| 7,628,730 B1 | 12/2009 | Watterson et al. |
| D610,635 S | 2/2010 | Hildebrandt |
| 7,778,851 B2 | 8/2010 | Schoenberg et al. |
| 7,809,601 B2 | 10/2010 | Shaya et al. |
| 7,815,551 B2 | 10/2010 | Merli |
| 7,833,135 B2 | 11/2010 | Radow et al. |
| 7,837,472 B1 | 11/2010 | Elsmore et al. |
| 7,955,219 B2 | 6/2011 | Birrell et al. |
| 7,969,315 B1 | 6/2011 | Ross et al. |
| 7,988,599 B2 | 8/2011 | Ainsworth et al. |
| 8,012,107 B2 | 9/2011 | Einav et al. |
| 8,021,270 B2 | 9/2011 | D'Eredita |
| 8,038,578 B2 | 10/2011 | Olrik et al. |
| 8,079,937 B2 | 12/2011 | Bedell |
| 8,113,991 B2 | 2/2012 | Kutliroff |
| 8,177,732 B2 | 5/2012 | Einav et al. |
| 8,287,434 B2 | 10/2012 | Zavadsky et al. |
| 8,298,123 B2 | 10/2012 | Hickman |
| 8,371,990 B2 | 2/2013 | Shea |
| 8,419,593 B2 | 4/2013 | Ainsworth et al. |
| 8,465,398 B2 | 6/2013 | Lee et al. |
| 8,506,458 B2 | 8/2013 | Dugan |
| 8,515,777 B1 | 8/2013 | Rajasenan |
| 8,540,515 B2 | 9/2013 | Williams et al. |
| 8,540,516 B2 | 9/2013 | Williams et al. |
| 8,556,778 B1 | 10/2013 | Dugan |
| 8,607,465 B1 | 12/2013 | Edwards |
| 8,613,689 B2 | 12/2013 | Dyer et al. |
| 8,672,812 B2 | 3/2014 | Dugan |
| 8,751,264 B2 | 6/2014 | Beraja et al. |
| 8,784,273 B2 | 7/2014 | Dugan |
| 8,823,448 B1 | 9/2014 | Shen |
| 8,845,493 B2 | 9/2014 | Watterson et al. |
| 8,849,681 B2 | 9/2014 | Hargrove et al. |
| 8,864,628 B2 | 10/2014 | Boyette et al. |
| 8,893,287 B2 | 11/2014 | Gjonej et al. |
| 8,911,327 B1 | 12/2014 | Boyette |
| 8,979,711 B2 | 3/2015 | Dugan |
| 9,004,598 B2 | 4/2015 | Weber |
| 9,044,630 B1 | 6/2015 | Lampert et al. |
| 9,167,281 B2 | 10/2015 | Petrov et al. |
| D744,050 S | 11/2015 | Colburn |
| 9,248,071 B1 | 2/2016 | Brenda |
| 9,272,091 B2 | 3/2016 | Skelton |
| 9,272,185 B2 | 3/2016 | Dugan |
| 9,283,434 B1 | 3/2016 | Wu |
| 9,295,878 B2 | 3/2016 | Corbalis et al. |
| 9,311,789 B1 | 4/2016 | Gwin |
| 9,312,907 B2 | 4/2016 | Auchinleck et al. |
| 9,367,668 B2 | 6/2016 | Flynt et al. |
| 9,409,054 B2 | 8/2016 | Dugan |
| 9,443,205 B2 | 9/2016 | Wall |
| 9,474,935 B2 | 10/2016 | Abbondanza et al. |

(56) References Cited

U.S. PATENT DOCUMENTS

| | | |
|---|---|---|
| 9,480,873 B2 | 11/2016 | Chuang |
| 9,481,428 B2 | 11/2016 | Gros |
| 9,514,277 B2 | 12/2016 | Hassing et al. |
| 9,566,472 B2 | 2/2017 | Dugan |
| 9,579,056 B2 | 2/2017 | Rosenbek et al. |
| 9,629,558 B2 | 4/2017 | Yuen et al. |
| 9,640,057 B1 | 5/2017 | Ross |
| 9,707,147 B2 | 7/2017 | Levital et al. |
| 9,713,744 B2 | 7/2017 | Suzuki |
| D794,142 S | 8/2017 | Zhou |
| 9,717,947 B2 | 8/2017 | Lin |
| 9,737,761 B1 | 8/2017 | Govindarajan |
| 9,757,612 B2 | 9/2017 | Weber |
| 9,782,621 B2 | 10/2017 | Chiang et al. |
| 9,802,076 B2 | 10/2017 | Murray et al. |
| 9,802,081 B2 | 10/2017 | Ridgel et al. |
| 9,813,239 B2 | 11/2017 | Chee et al. |
| 9,827,445 B2 | 11/2017 | Marcos et al. |
| 9,849,337 B2 | 12/2017 | Roman et al. |
| 9,868,028 B2 | 1/2018 | Shin |
| 9,872,087 B2 | 1/2018 | DelloStritto et al. |
| 9,872,637 B2 | 1/2018 | Kording et al. |
| 9,914,053 B2 | 3/2018 | Dugan |
| 9,919,198 B2 | 3/2018 | Romeo et al. |
| 9,937,382 B2 | 4/2018 | Dugan |
| 9,939,784 B1 | 4/2018 | Berardinelli |
| 9,977,587 B2 | 5/2018 | Mountain |
| 9,993,181 B2 | 6/2018 | Ross |
| 10,004,946 B2 | 6/2018 | Ross |
| D826,349 S | 8/2018 | Oblamski |
| 10,055,550 B2 | 8/2018 | Goetz |
| 10,058,473 B2 | 8/2018 | Oshima et al. |
| 10,074,148 B2 | 9/2018 | Cashman et al. |
| 10,089,443 B2 | 10/2018 | Miller et al. |
| 10,111,643 B2 | 10/2018 | Shulhauser et al. |
| 10,137,328 B2 | 11/2018 | Baudhuin |
| 10,143,395 B2 | 12/2018 | Chakravarthy et al. |
| 10,155,134 B2 | 12/2018 | Dugan |
| 10,159,872 B2 | 12/2018 | Sasaki et al. |
| 10,173,094 B2 | 1/2019 | Gomberg |
| 10,173,095 B2 | 1/2019 | Gomberg et al. |
| 10,173,096 B2 | 1/2019 | Gomberg et al. |
| 10,173,097 B2 | 1/2019 | Gomberg et al. |
| 10,198,928 B1 | 2/2019 | Ross et al. |
| 10,226,663 B2 | 3/2019 | Gomberg et al. |
| 10,231,664 B2 | 3/2019 | Ganesh |
| 10,244,990 B2 | 4/2019 | Hu et al. |
| 10,258,823 B2 | 4/2019 | Cole |
| 10,322,315 B2 | 6/2019 | Foley et al. |
| 10,325,070 B2 | 6/2019 | Beale et al. |
| 10,327,697 B1 | 6/2019 | Stein et al. |
| 10,369,021 B2 | 8/2019 | Zoss et al. |
| 10,380,866 B1 | 8/2019 | Ross et al. |
| 10,413,238 B1 | 9/2019 | Cooper |
| 10,424,033 B2 | 9/2019 | Romeo |
| 10,430,552 B2 | 10/2019 | Mihai |
| D866,957 S | 11/2019 | Ross et al. |
| 10,468,131 B2 | 11/2019 | Macoviak et al. |
| 10,475,323 B1 | 11/2019 | Ross |
| 10,475,537 B2 | 11/2019 | Purdie et al. |
| 10,492,977 B2 | 12/2019 | Kapure et al. |
| 10,507,358 B2 | 12/2019 | Kinnunen et al. |
| 10,542,914 B2 | 1/2020 | Forth et al. |
| 10,546,467 B1 | 1/2020 | Luciano, Jr. et al. |
| 10,569,122 B2 | 2/2020 | Johnson |
| 10,572,626 B2 | 2/2020 | Balram |
| 10,576,331 B2 | 3/2020 | Kuo |
| 10,581,896 B2 | 3/2020 | Nachenberg |
| 10,625,114 B2 | 4/2020 | Ercanbrack |
| 10,646,746 B1 | 5/2020 | Gomberg et al. |
| 10,660,534 B2 | 5/2020 | Lee et al. |
| 10,678,890 B2 | 6/2020 | Bitran et al. |
| 10,685,092 B2 | 6/2020 | Paparella et al. |
| 10,777,200 B2 | 9/2020 | Will et al. |
| 10,786,181 B1 | 9/2020 | Echols |
| D899,605 S | 10/2020 | Ross et al. |
| 10,792,495 B2 | 10/2020 | Izvorski et al. |
| 10,867,695 B2 | 12/2020 | Neagle |
| 10,874,905 B2 | 12/2020 | Belson et al. |
| D907,143 S | 1/2021 | Ach et al. |
| 10,881,911 B2 | 1/2021 | Kwon et al. |
| 10,918,332 B2 | 2/2021 | Belson et al. |
| 10,931,643 B1 | 2/2021 | Neumann |
| 10,987,176 B2 | 4/2021 | Poltaretskyi et al. |
| 10,991,463 B2 | 4/2021 | Kutzko et al. |
| 11,000,735 B2 | 5/2021 | Orady et al. |
| 11,045,709 B2 | 6/2021 | Putnam |
| 11,065,170 B2 | 7/2021 | Yang et al. |
| 11,065,527 B2 | 7/2021 | Putnam |
| 11,069,436 B2 | 7/2021 | Mason et al. |
| 11,071,597 B2 | 7/2021 | Posnack et al. |
| 11,075,000 B2 | 7/2021 | Mason et al. |
| D928,635 S | 8/2021 | Hacking et al. |
| 11,087,865 B2 | 8/2021 | Mason et al. |
| 11,101,028 B2 | 8/2021 | Mason et al. |
| 11,107,591 B1 | 8/2021 | Mason |
| 11,139,060 B2 | 10/2021 | Mason et al. |
| 11,185,735 B2 | 11/2021 | Arn et al. |
| D939,096 S | 12/2021 | Lee |
| D939,644 S | 12/2021 | Ach et al. |
| D940,797 S | 1/2022 | Ach et al. |
| D940,891 S | 1/2022 | Lee |
| 11,229,727 B2 | 1/2022 | Tatonetti |
| 11,229,788 B1 | 1/2022 | John |
| 11,265,234 B2 | 3/2022 | Guaneri et al. |
| 11,270,795 B2 | 3/2022 | Mason et al. |
| 11,272,879 B2 | 3/2022 | Wiedenhoefer et al. |
| 11,278,766 B2 | 3/2022 | Lee |
| 11,282,599 B2 | 3/2022 | Mason et al. |
| 11,282,604 B2 | 3/2022 | Mason et al. |
| 11,282,608 B2 | 3/2022 | Mason et al. |
| 11,284,797 B2 | 3/2022 | Mason et al. |
| D948,639 S | 4/2022 | Ach et al. |
| 11,295,848 B2 | 4/2022 | Mason et al. |
| 11,298,284 B2 | 4/2022 | Bayerlein |
| 11,309,085 B2 | 4/2022 | Mason et al. |
| 11,317,975 B2 | 5/2022 | Mason et al. |
| 11,325,005 B2 | 5/2022 | Mason et al. |
| 11,328,807 B2 | 5/2022 | Mason et al. |
| 11,337,648 B2 | 5/2022 | Mason |
| 11,348,683 B2 | 5/2022 | Guaneri et al. |
| 11,370,328 B2 | 6/2022 | Main |
| 11,376,470 B2 | 7/2022 | Weldemariam |
| 11,404,150 B2 | 8/2022 | Guaneri et al. |
| 11,410,768 B2 | 8/2022 | Mason et al. |
| 11,422,841 B2 | 8/2022 | Jeong |
| 11,495,355 B2 | 11/2022 | McNutt et al. |
| 11,508,258 B2 | 11/2022 | Nakashima et al. |
| 11,508,482 B2 | 11/2022 | Mason et al. |
| 11,515,021 B2 | 11/2022 | Mason |
| 11,515,028 B2 | 11/2022 | Mason |
| 11,524,210 B2 | 12/2022 | Kim et al. |
| 11,527,326 B2 | 12/2022 | McNair et al. |
| 11,532,402 B2 | 12/2022 | Farley et al. |
| 11,534,654 B2 | 12/2022 | Silcock et al. |
| D976,339 S | 1/2023 | Li |
| 11,541,274 B2 | 1/2023 | Hacking |
| 11,636,944 B2 | 4/2023 | Hanrahan et al. |
| 11,663,673 B2 | 5/2023 | Pyles |
| 11,673,024 B2 | 6/2023 | Omid-Zohoor |
| 11,701,548 B2 | 7/2023 | Posnack et al. |
| 11,776,676 B2 | 10/2023 | Savolainen |
| 11,957,960 B2 | 4/2024 | Bissonnette et al. |
| 12,205,704 B2 | 1/2025 | Hosoi et al. |
| 2001/0044573 A1 | 11/2001 | Manoli |
| 2002/0072452 A1 | 6/2002 | Torkelson |
| 2002/0143279 A1 | 10/2002 | Porter et al. |
| 2002/0160883 A1 | 10/2002 | Dugan |
| 2002/0183599 A1 | 12/2002 | Castellanos |
| 2003/0013072 A1 | 1/2003 | Thomas |
| 2003/0036683 A1 | 2/2003 | Kehr et al. |
| 2003/0064860 A1 | 4/2003 | Yamashita et al. |
| 2003/0064863 A1 | 4/2003 | Chen |
| 2003/0083596 A1 | 5/2003 | Kramer et al. |

(56) References Cited

U.S. PATENT DOCUMENTS

| | | |
|---|---|---|
| 2003/0092536 A1 | 5/2003 | Romanelli et al. |
| 2003/0181832 A1 | 9/2003 | Carnahan et al. |
| 2004/0072652 A1 | 4/2004 | Alessandri et al. |
| 2004/0102931 A1 | 5/2004 | Ellis et al. |
| 2004/0106502 A1 | 6/2004 | Sher |
| 2004/0147969 A1 | 7/2004 | Mann et al. |
| 2004/0172093 A1 | 9/2004 | Rummerfield |
| 2004/0194572 A1 | 10/2004 | Kim |
| 2004/0204959 A1 | 10/2004 | Moreano et al. |
| 2005/0015118 A1 | 1/2005 | Davis et al. |
| 2005/0020411 A1 | 1/2005 | Andrews |
| 2005/0043153 A1 | 2/2005 | Krietzman |
| 2005/0049122 A1 | 3/2005 | Vallone et al. |
| 2005/0085346 A1 | 4/2005 | Johnson |
| 2005/0085353 A1 | 4/2005 | Johnson |
| 2005/0115561 A1 | 6/2005 | Stahmann |
| 2005/0274220 A1 | 12/2005 | Reboullet |
| 2006/0003871 A1 | 1/2006 | Houghton et al. |
| 2006/0046905 A1 | 3/2006 | Doody et al. |
| 2006/0058648 A1 | 3/2006 | Meier |
| 2006/0064136 A1 | 3/2006 | Wang |
| 2006/0064329 A1 | 3/2006 | Abolfathi et al. |
| 2006/0199700 A1 | 9/2006 | LaStayo et al. |
| 2006/0247095 A1 | 11/2006 | Rummerfield |
| 2006/0277074 A1 | 12/2006 | Einav |
| 2007/0042868 A1 | 2/2007 | Fisher et al. |
| 2007/0118389 A1 | 5/2007 | Shipon |
| 2007/0137307 A1 | 6/2007 | Gruben et al. |
| 2007/0173392 A1 | 7/2007 | Stanford |
| 2007/0184414 A1 | 8/2007 | Perez |
| 2007/0194939 A1 | 8/2007 | Alvarez et al. |
| 2007/0219059 A1 | 9/2007 | Schwartz |
| 2007/0287597 A1 | 12/2007 | Cameron |
| 2008/0021834 A1 | 1/2008 | Holla et al. |
| 2008/0082356 A1 | 4/2008 | Friedlander et al. |
| 2008/0096726 A1 | 4/2008 | Riley et al. |
| 2008/0153592 A1 | 6/2008 | James-Herbert |
| 2008/0161166 A1 | 7/2008 | Lo |
| 2008/0161733 A1 | 7/2008 | Einav et al. |
| 2008/0281633 A1 | 11/2008 | Burdea et al. |
| 2008/0300914 A1 | 12/2008 | Karkanias et al. |
| 2008/0312040 A1 | 12/2008 | Ochi |
| 2009/0011907 A1 | 1/2009 | Radow et al. |
| 2009/0058635 A1 | 3/2009 | LaLonde et al. |
| 2009/0070138 A1 | 3/2009 | Langheier et al. |
| 2009/0211395 A1 | 8/2009 | Mule |
| 2009/0270227 A1 | 10/2009 | Ashby et al. |
| 2009/0287503 A1 | 11/2009 | Angell et al. |
| 2009/0299766 A1 | 12/2009 | Friedlander et al. |
| 2010/0048358 A1 | 2/2010 | Tchao et al. |
| 2010/0062818 A1 | 3/2010 | Haughay, Jr. |
| 2010/0076786 A1 | 3/2010 | Dalton et al. |
| 2010/0121160 A1 | 5/2010 | Stark et al. |
| 2010/0173747 A1 | 7/2010 | Chen et al. |
| 2010/0216168 A1 | 8/2010 | Heinzman et al. |
| 2010/0234184 A1 | 9/2010 | Le Page et al. |
| 2010/0248899 A1 | 9/2010 | Bedell et al. |
| 2010/0248905 A1 | 9/2010 | Lu |
| 2010/0268304 A1 | 10/2010 | Matos |
| 2010/0298102 A1 | 11/2010 | Bosecker et al. |
| 2010/0326207 A1 | 12/2010 | Topel |
| 2011/0010188 A1 | 1/2011 | Yoshikawa et al. |
| 2011/0047108 A1 | 2/2011 | Chakrabarty et al. |
| 2011/0082007 A1 | 4/2011 | Birrell |
| 2011/0087137 A1 | 4/2011 | Hanoun |
| 2011/0119212 A1 | 5/2011 | De Bruin et al. |
| 2011/0172059 A1 | 7/2011 | Watterson et al. |
| 2011/0195819 A1 | 8/2011 | Shaw et al. |
| 2011/0218814 A1 | 9/2011 | Coats |
| 2011/0275483 A1 | 11/2011 | Dugan |
| 2011/0306846 A1 | 12/2011 | Osorio |
| 2012/0041771 A1 | 2/2012 | Cosentino et al. |
| 2012/0065987 A1 | 3/2012 | Farooq et al. |
| 2012/0116258 A1 | 5/2012 | Lee |
| 2012/0167709 A1 | 7/2012 | Chen et al. |
| 2012/0183939 A1 | 7/2012 | Aragones et al. |
| 2012/0190502 A1 | 7/2012 | Paulus et al. |
| 2012/0232438 A1 | 9/2012 | Cataldi et al. |
| 2012/0259648 A1 | 10/2012 | Mallon et al. |
| 2012/0295240 A1 | 11/2012 | Walker et al. |
| 2012/0296455 A1 | 11/2012 | Ohnemus et al. |
| 2012/0310667 A1 | 12/2012 | Altman et al. |
| 2013/0123071 A1 | 5/2013 | Rhea |
| 2013/0123667 A1 | 5/2013 | Komatireddy et al. |
| 2013/0137550 A1 | 5/2013 | Skinner et al. |
| 2013/0165195 A1 | 6/2013 | Watterson |
| 2013/0178334 A1 | 7/2013 | Brammer |
| 2013/0211281 A1 | 8/2013 | Ross et al. |
| 2013/0253943 A1 | 9/2013 | Lee et al. |
| 2013/0274069 A1 | 10/2013 | Watterson et al. |
| 2013/0296987 A1 | 11/2013 | Rogers et al. |
| 2013/0318027 A1 | 11/2013 | Almogy et al. |
| 2013/0332616 A1 | 12/2013 | Landwehr |
| 2013/0345025 A1 | 12/2013 | van der Merwe |
| 2014/0006042 A1 | 1/2014 | Keefe et al. |
| 2014/0011640 A1 | 1/2014 | Dugan |
| 2014/0031174 A1 | 1/2014 | Huang |
| 2014/0089836 A1 | 3/2014 | Damani et al. |
| 2014/0113261 A1 | 4/2014 | Akiba |
| 2014/0113768 A1 | 4/2014 | Lin et al. |
| 2014/0135173 A1 | 5/2014 | Watterson |
| 2014/0155129 A1 | 6/2014 | Dugan |
| 2014/0172442 A1 | 6/2014 | Broderick |
| 2014/0172460 A1 | 6/2014 | Kohli |
| 2014/0188009 A1 | 7/2014 | Lange et al. |
| 2014/0194250 A1 | 7/2014 | Reich et al. |
| 2014/0194251 A1 | 7/2014 | Reich et al. |
| 2014/0200414 A1 | 7/2014 | Osorio |
| 2014/0207264 A1 | 7/2014 | Quy |
| 2014/0207486 A1 | 7/2014 | Carty et al. |
| 2014/0228649 A1 | 8/2014 | Rayner et al. |
| 2014/0246499 A1 | 9/2014 | Proud et al. |
| 2014/0256511 A1 | 9/2014 | Smith |
| 2014/0257837 A1 | 9/2014 | Walker et al. |
| 2014/0274565 A1 | 9/2014 | Boyette et al. |
| 2014/0274622 A1 | 9/2014 | Leonhard |
| 2014/0303540 A1 | 10/2014 | Baym |
| 2014/0309083 A1 | 10/2014 | Dugan |
| 2014/0322686 A1 | 10/2014 | Kang |
| 2014/0371816 A1 | 12/2014 | Matos |
| 2015/0025816 A1 | 1/2015 | Ross |
| 2015/0045700 A1* | 2/2015 | Cavanagh ............. G16H 40/67 600/595 |
| 2015/0065213 A1 | 3/2015 | Dugan |
| 2015/0073814 A1 | 3/2015 | Linebaugh |
| 2015/0088544 A1 | 3/2015 | Goldberg |
| 2015/0094192 A1 | 4/2015 | Skwortsow et al. |
| 2015/0099458 A1 | 4/2015 | Weisner et al. |
| 2015/0099952 A1 | 4/2015 | Lain et al. |
| 2015/0112230 A1 | 4/2015 | Iglesias |
| 2015/0130830 A1 | 5/2015 | Nagasaki |
| 2015/0141200 A1 | 5/2015 | Murray et al. |
| 2015/0149217 A1 | 5/2015 | Kaburagi |
| 2015/0151162 A1 | 6/2015 | Dugan |
| 2015/0161331 A1 | 6/2015 | Oleynik |
| 2015/0196804 A1 | 7/2015 | Koduri |
| 2015/0196805 A1 | 7/2015 | Koduri |
| 2015/0217056 A1 | 8/2015 | Kadavy et al. |
| 2015/0251074 A1 | 9/2015 | Ahmed et al. |
| 2015/0257679 A1 | 9/2015 | Ross |
| 2015/0265209 A1 | 9/2015 | Zhang |
| 2015/0290061 A1 | 10/2015 | Stafford et al. |
| 2015/0339442 A1 | 11/2015 | Oleynik |
| 2015/0341812 A1 | 11/2015 | Dion et al. |
| 2015/0351664 A1 | 12/2015 | Ross |
| 2015/0351665 A1 | 12/2015 | Ross |
| 2015/0360069 A1 | 12/2015 | Marti et al. |
| 2015/0379232 A1 | 12/2015 | Mainwaring et al. |
| 2015/0379430 A1 | 12/2015 | Dirac et al. |
| 2016/0007885 A1 | 1/2016 | Basta |
| 2016/0023081 A1 | 1/2016 | Popa-Simil et al. |
| 2016/0045170 A1 | 2/2016 | Migita |
| 2016/0096073 A1 | 4/2016 | Rahman et al. |
| 2016/0117471 A1 | 4/2016 | Belt et al. |

(56) References Cited

U.S. PATENT DOCUMENTS

| | | |
|---|---|---|
| 2016/0140319 A1 | 5/2016 | Stark |
| 2016/0143593 A1 | 5/2016 | Fu et al. |
| 2016/0151670 A1 | 6/2016 | Dugan |
| 2016/0166833 A1 | 6/2016 | Bum |
| 2016/0166881 A1 | 6/2016 | Ridgel et al. |
| 2016/0193306 A1 | 7/2016 | Rabovsky et al. |
| 2016/0213924 A1 | 7/2016 | Coleman |
| 2016/0275259 A1 | 9/2016 | Nolan et al. |
| 2016/0287166 A1 | 10/2016 | Tran |
| 2016/0302721 A1 | 10/2016 | Wiedenhoefer et al. |
| 2016/0317869 A1 | 11/2016 | Dugan |
| 2016/0322078 A1 | 11/2016 | Bose et al. |
| 2016/0325140 A1 | 11/2016 | Wu |
| 2016/0332028 A1 | 11/2016 | Melnik |
| 2016/0354636 A1 | 12/2016 | Jang |
| 2016/0361597 A1 | 12/2016 | Cole et al. |
| 2016/0373477 A1 | 12/2016 | Moyle |
| 2017/0004260 A1 | 1/2017 | Moturu et al. |
| 2017/0033375 A1 | 2/2017 | Ohmori et al. |
| 2017/0042467 A1 | 2/2017 | Herr et al. |
| 2017/0046488 A1 | 2/2017 | Pereira |
| 2017/0065851 A1 | 3/2017 | Deluca et al. |
| 2017/0080320 A1 | 3/2017 | Smith |
| 2017/0095670 A1 | 4/2017 | Ghaffari et al. |
| 2017/0095692 A1 | 4/2017 | Chang et al. |
| 2017/0095693 A1 | 4/2017 | Chang et al. |
| 2017/0100637 A1 | 4/2017 | Princen et al. |
| 2017/0106242 A1 | 4/2017 | Dugan |
| 2017/0113092 A1 | 4/2017 | Johnson |
| 2017/0128769 A1 | 5/2017 | Long et al. |
| 2017/0132947 A1 | 5/2017 | Maeda et al. |
| 2017/0136296 A1 | 5/2017 | Barrera et al. |
| 2017/0143261 A1 | 5/2017 | Wiedenhoefer et al. |
| 2017/0147752 A1 | 5/2017 | Toru |
| 2017/0147789 A1 | 5/2017 | Wiedenhoefer et al. |
| 2017/0148297 A1 | 5/2017 | Ross |
| 2017/0168555 A1 | 6/2017 | Munoz et al. |
| 2017/0181698 A1 | 6/2017 | Wiedenhoefer et al. |
| 2017/0190052 A1 | 7/2017 | Jaekel et al. |
| 2017/0202724 A1 | 7/2017 | De Rossi |
| 2017/0209766 A1 | 7/2017 | Riley et al. |
| 2017/0220751 A1 | 8/2017 | Davis |
| 2017/0235882 A1 | 8/2017 | Orlov et al. |
| 2017/0235906 A1 | 8/2017 | Dorris et al. |
| 2017/0243028 A1 | 8/2017 | LaFever et al. |
| 2017/0262604 A1 | 9/2017 | Francois |
| 2017/0265800 A1 | 9/2017 | Auchinleck et al. |
| 2017/0266501 A1 | 9/2017 | Sanders et al. |
| 2017/0270260 A1 | 9/2017 | Shetty |
| 2017/0278209 A1 | 9/2017 | Olsen et al. |
| 2017/0281390 A1 | 10/2017 | Abdul-Hafiz et al. |
| 2017/0282015 A1 | 10/2017 | Wicks et al. |
| 2017/0283508 A1 | 10/2017 | Demopulos et al. |
| 2017/0286621 A1 | 10/2017 | Cox |
| 2017/0291067 A1 | 10/2017 | Jang et al. |
| 2017/0296861 A1 | 10/2017 | Burkinshaw |
| 2017/0300654 A1 | 10/2017 | Stein et al. |
| 2017/0304024 A1 | 10/2017 | Nobrega |
| 2017/0312614 A1 | 11/2017 | Tran et al. |
| 2017/0323481 A1 | 11/2017 | Tran et al. |
| 2017/0329917 A1 | 11/2017 | McRaith et al. |
| 2017/0329933 A1 | 11/2017 | Brust |
| 2017/0333755 A1 | 11/2017 | Rider |
| 2017/0337033 A1 | 11/2017 | Duyan et al. |
| 2017/0337334 A1 | 11/2017 | Stanczak |
| 2017/0344726 A1 | 11/2017 | Duffy et al. |
| 2017/0347923 A1 | 12/2017 | Roh |
| 2017/0360586 A1 | 12/2017 | Dempers et al. |
| 2017/0368413 A1 | 12/2017 | Shavit |
| 2018/0017806 A1 | 1/2018 | Wang et al. |
| 2018/0036593 A1 | 2/2018 | Ridgel et al. |
| 2018/0052962 A1 | 2/2018 | Van Der Koijk et al. |
| 2018/0056104 A1 | 3/2018 | Cromie et al. |
| 2018/0060494 A1 | 3/2018 | Dias et al. |
| 2018/0071565 A1 | 3/2018 | Gomberg et al. |
| 2018/0071566 A1 | 3/2018 | Gomberg et al. |
| 2018/0071569 A1 | 3/2018 | Gomberg et al. |
| 2018/0071570 A1 | 3/2018 | Gomberg et al. |
| 2018/0071571 A1 | 3/2018 | Gomberg et al. |
| 2018/0071572 A1 | 3/2018 | Gomberg et al. |
| 2018/0075205 A1 | 3/2018 | Moturu et al. |
| 2018/0078843 A1 | 3/2018 | Tran et al. |
| 2018/0085615 A1 | 3/2018 | Astolfi et al. |
| 2018/0096111 A1 | 4/2018 | Wells et al. |
| 2018/0099178 A1 | 4/2018 | Schaefer et al. |
| 2018/0102190 A1 | 4/2018 | Hogue et al. |
| 2018/0103859 A1 | 4/2018 | Provenzano |
| 2018/0116741 A1 | 5/2018 | Garcia Kilroy et al. |
| 2018/0140927 A1 | 5/2018 | Kito |
| 2018/0146870 A1 | 5/2018 | Shemesh |
| 2018/0177612 A1 | 6/2018 | Trabish et al. |
| 2018/0177664 A1 | 6/2018 | Choi et al. |
| 2018/0178061 A1 | 6/2018 | O'larte et al. |
| 2018/0199855 A1 | 7/2018 | Odame et al. |
| 2018/0200577 A1 | 7/2018 | Dugan |
| 2018/0220935 A1 | 8/2018 | Tadano et al. |
| 2018/0228682 A1 | 8/2018 | Bayerlein et al. |
| 2018/0236307 A1 | 8/2018 | Hyde et al. |
| 2018/0240552 A1 | 8/2018 | Tuyl et al. |
| 2018/0253991 A1 | 9/2018 | Tang et al. |
| 2018/0256079 A1 | 9/2018 | Yang et al. |
| 2018/0256939 A1 | 9/2018 | Malcolm |
| 2018/0263530 A1 | 9/2018 | Jung |
| 2018/0263535 A1 | 9/2018 | Cramer |
| 2018/0263552 A1 | 9/2018 | Graman et al. |
| 2018/0264312 A1 | 9/2018 | Pompile et al. |
| 2018/0271432 A1 | 9/2018 | Auchinleck et al. |
| 2018/0272184 A1 | 9/2018 | Vassilaros et al. |
| 2018/0280784 A1 | 10/2018 | Romeo et al. |
| 2018/0296143 A1 | 10/2018 | Anderson et al. |
| 2018/0296157 A1 | 10/2018 | Bleich et al. |
| 2018/0318122 A1 | 11/2018 | Lecursi et al. |
| 2018/0326243 A1 | 11/2018 | Badi et al. |
| 2018/0330058 A1 | 11/2018 | Bates |
| 2018/0330810 A1 | 11/2018 | Gamarnik |
| 2018/0330824 A1 | 11/2018 | Athey et al. |
| 2018/0290017 A1 | 12/2018 | Fung |
| 2018/0353812 A1 | 12/2018 | Lannon et al. |
| 2018/0360340 A1 | 12/2018 | Rehse et al. |
| 2018/0373844 A1 | 12/2018 | Ferrandez-Escamez et al. |
| 2019/0009135 A1 | 1/2019 | Wu |
| 2019/0019163 A1 | 1/2019 | Batey et al. |
| 2019/0019573 A1 | 1/2019 | Lake et al. |
| 2019/0019578 A1 | 1/2019 | Vaccaro |
| 2019/0021929 A1 | 1/2019 | Einav et al. |
| 2019/0030415 A1 | 1/2019 | Volpe, Jr. |
| 2019/0031284 A1 | 1/2019 | Fuchs |
| 2019/0046794 A1 | 2/2019 | Goodall et al. |
| 2019/0060708 A1 | 2/2019 | Fung |
| 2019/0065970 A1 | 2/2019 | Bonutti et al. |
| 2019/0066832 A1 | 2/2019 | Kang et al. |
| 2019/0076701 A1 | 3/2019 | Dugan |
| 2019/0080802 A1 | 3/2019 | Ziobro et al. |
| 2019/0088356 A1 | 3/2019 | Oliver et al. |
| 2019/0090744 A1 | 3/2019 | Mahfouz |
| 2019/0111299 A1 | 4/2019 | Radcliffe et al. |
| 2019/0115097 A1 | 4/2019 | Macoviak et al. |
| 2019/0117128 A1* | 4/2019 | Chen .................. A61B 5/1121 |
| 2019/0118038 A1 | 4/2019 | Tana et al. |
| 2019/0126099 A1 | 5/2019 | Hoang |
| 2019/0132948 A1 | 5/2019 | Longinotti-Buitoni et al. |
| 2019/0134454 A1 | 5/2019 | Mahoney et al. |
| 2019/0137988 A1 | 5/2019 | Cella et al. |
| 2019/0163876 A1 | 5/2019 | Remme et al. |
| 2019/0167988 A1 | 6/2019 | Shahriari et al. |
| 2019/0172587 A1 | 6/2019 | Park et al. |
| 2019/0175988 A1 | 6/2019 | Volterrani et al. |
| 2019/0183715 A1 | 6/2019 | Kapure et al. |
| 2019/0200920 A1 | 7/2019 | Tien et al. |
| 2019/0209891 A1 | 7/2019 | Fung |
| 2019/0223797 A1 | 7/2019 | Tran |
| 2019/0224528 A1 | 7/2019 | Omid-Zohoor et al. |
| 2019/0228856 A1 | 7/2019 | Leifer |
| 2019/0240103 A1 | 8/2019 | Hepler et al. |

(56) References Cited

U.S. PATENT DOCUMENTS

| | | |
|---|---|---|
| 2019/0240541 A1 | 8/2019 | Denton et al. |
| 2019/0244540 A1 | 8/2019 | Errante et al. |
| 2019/0251456 A1 | 8/2019 | Constantin |
| 2019/0261959 A1 | 8/2019 | Frankel |
| 2019/0262084 A1 | 8/2019 | Roh |
| 2019/0269343 A1 | 9/2019 | Ramos Murguialday et al. |
| 2019/0274523 A1 | 9/2019 | Bates et al. |
| 2019/0275368 A1 | 9/2019 | Maroldi |
| 2019/0304584 A1 | 10/2019 | Savolainen |
| 2019/0307983 A1 | 10/2019 | Goldman |
| 2019/0314681 A1 | 10/2019 | Yang |
| 2019/0344123 A1 | 11/2019 | Rubin et al. |
| 2019/0354632 A1 | 11/2019 | Mital et al. |
| 2019/0362242 A1 | 11/2019 | Pillai et al. |
| 2019/0366146 A1 | 12/2019 | Tong et al. |
| 2019/0388728 A1 | 12/2019 | Wang et al. |
| 2020/0005928 A1 | 1/2020 | Daniel |
| 2020/0038703 A1 | 2/2020 | Cleary et al. |
| 2020/0051446 A1 | 2/2020 | Rubinstein et al. |
| 2020/0054922 A1 | 2/2020 | Azaria |
| 2020/0066390 A1 | 2/2020 | Svendrys et al. |
| 2020/0085300 A1 | 3/2020 | Kwatra et al. |
| 2020/0093418 A1 | 3/2020 | Kluger et al. |
| 2020/0139194 A1 | 5/2020 | Min |
| 2020/0143922 A1 | 5/2020 | Chekroud et al. |
| 2020/0151595 A1 | 5/2020 | Jayalath et al. |
| 2020/0151646 A1 | 5/2020 | De La Fuente Sanchez |
| 2020/0152339 A1 | 5/2020 | Pulitzer et al. |
| 2020/0160198 A1 | 5/2020 | Reeves et al. |
| 2020/0170876 A1 | 6/2020 | Kapure et al. |
| 2020/0176098 A1 | 6/2020 | Lucas et al. |
| 2020/0197744 A1 | 6/2020 | Schweighofer |
| 2020/0221975 A1 | 7/2020 | Basta et al. |
| 2020/0237291 A1 | 7/2020 | Raja |
| 2020/0261763 A1 | 8/2020 | Park |
| 2020/0267487 A1 | 8/2020 | Siva |
| 2020/0275886 A1 | 9/2020 | Mason |
| 2020/0289045 A1 | 9/2020 | Hacking et al. |
| 2020/0289046 A1 | 9/2020 | Hacking et al. |
| 2020/0289879 A1 | 9/2020 | Hacking et al. |
| 2020/0289880 A1 | 9/2020 | Hacking et al. |
| 2020/0289881 A1 | 9/2020 | Hacking et al. |
| 2020/0289889 A1 | 9/2020 | Hacking et al. |
| 2020/0293712 A1 | 9/2020 | Potts et al. |
| 2020/0303063 A1 | 9/2020 | Sharma et al. |
| 2020/0334972 A1 | 10/2020 | Gopalakrishnan |
| 2020/0353314 A1 | 11/2020 | Messinger |
| 2020/0357299 A1 | 11/2020 | Patel et al. |
| 2020/0365256 A1 | 11/2020 | Hayashitani et al. |
| 2020/0391080 A1 | 12/2020 | Powers |
| 2020/0395112 A1 | 12/2020 | Ronner |
| 2020/0401224 A1 | 12/2020 | Cotton |
| 2020/0410385 A1 | 12/2020 | Otsuki |
| 2020/0411162 A1 | 12/2020 | Lien et al. |
| 2021/0005224 A1 | 1/2021 | Rothschild et al. |
| 2021/0005319 A1 | 1/2021 | Otsuki et al. |
| 2021/0074178 A1 | 3/2021 | Ilan et al. |
| 2021/0076981 A1 | 3/2021 | Hacking et al. |
| 2021/0077860 A1 | 3/2021 | Posnack et al. |
| 2021/0077884 A1 | 3/2021 | De Las Casas Zolezzi et al. |
| 2021/0098129 A1 | 4/2021 | Neumann |
| 2021/0101051 A1 | 4/2021 | Posnack et al. |
| 2021/0113890 A1 | 4/2021 | Posnack et al. |
| 2021/0127974 A1 | 5/2021 | Mason et al. |
| 2021/0128080 A1 | 5/2021 | Mason et al. |
| 2021/0128255 A1 | 5/2021 | Mason et al. |
| 2021/0128978 A1 | 5/2021 | Gilstrom et al. |
| 2021/0134412 A1 | 5/2021 | Guaneri et al. |
| 2021/0134425 A1 | 5/2021 | Mason et al. |
| 2021/0134427 A1 | 5/2021 | Mason et al. |
| 2021/0134428 A1 | 5/2021 | Mason |
| 2021/0134430 A1 | 5/2021 | Mason et al. |
| 2021/0134432 A1 | 5/2021 | Mason et al. |
| 2021/0134456 A1 | 5/2021 | Posnack et al. |
| 2021/0134457 A1 | 5/2021 | Mason et al. |
| 2021/0134458 A1 | 5/2021 | Mason et al. |
| 2021/0134463 A1 | 5/2021 | Mason et al. |
| 2021/0138304 A1 | 5/2021 | Mason et al. |
| 2021/0142875 A1 | 5/2021 | Mason et al. |
| 2021/0142893 A1 | 5/2021 | Guaneri et al. |
| 2021/0142898 A1 | 5/2021 | Mason et al. |
| 2021/0142903 A1 | 5/2021 | Mason et al. |
| 2021/0144074 A1 | 5/2021 | Guaneri et al. |
| 2021/0186419 A1 | 6/2021 | Van Ee et al. |
| 2021/0202090 A1 | 7/2021 | ODonovan et al. |
| 2021/0202103 A1 | 7/2021 | Bostic et al. |
| 2021/0205660 A1 | 7/2021 | Shavit |
| 2021/0244998 A1 | 8/2021 | Hacking et al. |
| 2021/0245003 A1 | 8/2021 | Turner |
| 2021/0251562 A1 | 8/2021 | Jain |
| 2021/0272677 A1 | 9/2021 | Barbee |
| 2021/0338469 A1 | 11/2021 | Dempers |
| 2021/0343384 A1 | 11/2021 | Purushothaman et al. |
| 2021/0345879 A1 | 11/2021 | Mason et al. |
| 2021/0345975 A1 | 11/2021 | Mason et al. |
| 2021/0350888 A1 | 11/2021 | Guaneri et al. |
| 2021/0350898 A1 | 11/2021 | Mason et al. |
| 2021/0350899 A1 | 11/2021 | Mason et al. |
| 2021/0350901 A1 | 11/2021 | Mason et al. |
| 2021/0350902 A1 | 11/2021 | Mason et al. |
| 2021/0350914 A1 | 11/2021 | Guaneri et al. |
| 2021/0350926 A1 | 11/2021 | Mason et al. |
| 2021/0354002 A1 | 11/2021 | Schaefer |
| 2021/0361514 A1 | 11/2021 | Choi et al. |
| 2021/0366587 A1 | 11/2021 | Mason et al. |
| 2021/0375425 A1 | 12/2021 | Zhang |
| 2021/0379447 A1 | 12/2021 | Lee |
| 2021/0383909 A1 | 12/2021 | Mason et al. |
| 2021/0391091 A1 | 12/2021 | Mason |
| 2021/0398668 A1 | 12/2021 | Chock et al. |
| 2021/0407670 A1 | 12/2021 | Mason et al. |
| 2021/0407681 A1 | 12/2021 | Mason et al. |
| 2022/0000556 A1 | 1/2022 | Casey et al. |
| 2022/0015838 A1 | 1/2022 | Posnack |
| 2022/0016480 A1 | 1/2022 | Bissonnette et al. |
| 2022/0016482 A1 | 1/2022 | Bissonnette |
| 2022/0016485 A1 | 1/2022 | Bissonnette |
| 2022/0016486 A1 | 1/2022 | Bissonnette |
| 2022/0020469 A1 | 1/2022 | Tanner |
| 2022/0044806 A1 | 2/2022 | Sanders et al. |
| 2022/0047921 A1 | 2/2022 | Bissonnette |
| 2022/0066548 A1 | 3/2022 | Helot |
| 2022/0079690 A1 | 3/2022 | Mason et al. |
| 2022/0080256 A1 | 3/2022 | Arn et al. |
| 2022/0080265 A1 | 3/2022 | Watterson |
| 2022/0105384 A1 | 4/2022 | Hacking et al. |
| 2022/0105385 A1 | 4/2022 | Hacking et al. |
| 2022/0105390 A1 | 4/2022 | Yuasa |
| 2022/0115133 A1 | 4/2022 | Mason et al. |
| 2022/0118218 A1 | 4/2022 | Bense et al. |
| 2022/0126169 A1 | 4/2022 | Mason |
| 2022/0133576 A1 | 5/2022 | Choi et al. |
| 2022/0148725 A1 | 5/2022 | Mason et al. |
| 2022/0158916 A1 | 5/2022 | Mason et al. |
| 2022/0176039 A1 | 6/2022 | Lintereur et al. |
| 2022/0181004 A1 | 6/2022 | Zilca et al. |
| 2022/0193491 A1 | 6/2022 | Mason et al. |
| 2022/0230729 A1 | 7/2022 | Mason et al. |
| 2022/0238223 A1 | 7/2022 | Mason |
| 2022/0262483 A1 | 8/2022 | Rosenberg et al. |
| 2022/0262504 A1 | 8/2022 | Bratty et al. |
| 2022/0266094 A1 | 8/2022 | Mason et al. |
| 2022/0270738 A1 | 8/2022 | Mason et al. |
| 2022/0273985 A1 | 9/2022 | Jeong et al. |
| 2022/0273986 A1 | 9/2022 | Mason |
| 2022/0288460 A1 | 9/2022 | Mason |
| 2022/0288461 A1 | 9/2022 | Ashley et al. |
| 2022/0288462 A1 | 9/2022 | Ashley et al. |
| 2022/0293257 A1 | 9/2022 | Guaneri et al. |
| 2022/0300787 A1 | 9/2022 | Wall et al. |
| 2022/0304881 A1 | 9/2022 | Choi et al. |
| 2022/0304882 A1 | 9/2022 | Choi |
| 2022/0305328 A1 | 9/2022 | Choi et al. |
| 2022/0314072 A1 | 10/2022 | Bissonnette et al. |

(56) References Cited

U.S. PATENT DOCUMENTS

| | | | |
|---|---|---|---|
| 2022/0314075 A1 | 10/2022 | Mason et al. |
| 2022/0323826 A1 | 10/2022 | Khurana |
| 2022/0327714 A1 | 10/2022 | Cook et al. |
| 2022/0327807 A1 | 10/2022 | Cook et al. |
| 2022/0328181 A1 | 10/2022 | Mason et al. |
| 2022/0330823 A1 | 10/2022 | Janssen |
| 2022/0331663 A1 | 10/2022 | Mason |
| 2022/0338761 A1 | 10/2022 | Maddahi et al. |
| 2022/0339052 A1 | 10/2022 | Kim |
| 2022/0339501 A1 | 10/2022 | Mason et al. |
| 2022/0346703 A1 | 11/2022 | Abdo et al. |
| 2022/0351812 A1 | 11/2022 | Gassman et al. |
| 2022/0384010 A1 | 12/2022 | Kanayama |
| 2022/0384012 A1 | 12/2022 | Mason |
| 2022/0392591 A1 | 12/2022 | Guaneri et al. |
| 2022/0395232 A1 | 12/2022 | Locke |
| 2022/0401783 A1 | 12/2022 | Choi |
| 2022/0415469 A1 | 12/2022 | Mason |
| 2022/0415471 A1 | 12/2022 | Mason |
| 2023/0001268 A1 | 1/2023 | Bissonnette et al. |
| 2023/0013530 A1 | 1/2023 | Mason |
| 2023/0014598 A1 | 1/2023 | Mason et al. |
| 2023/0029639 A1 | 2/2023 | Roy |
| 2023/0048040 A1 | 2/2023 | Hacking et al. |
| 2023/0051751 A1 | 2/2023 | Hacking et al. |
| 2023/0058605 A1 | 2/2023 | Mason |
| 2023/0060039 A1 | 2/2023 | Mason |
| 2023/0072368 A1 | 3/2023 | Mason |
| 2023/0078793 A1 | 3/2023 | Mason |
| 2023/0119461 A1 | 4/2023 | Mason |
| 2023/0190100 A1 | 6/2023 | Stump |
| 2023/0197240 A1 | 6/2023 | Rosenberg |
| 2023/0201656 A1 | 6/2023 | Hacking et al. |
| 2023/0207097 A1 | 6/2023 | Mason |
| 2023/0207124 A1 | 6/2023 | Walsh et al. |
| 2023/0215539 A1 | 7/2023 | Rosenberg et al. |
| 2023/0215552 A1 | 7/2023 | Khotilovich et al. |
| 2023/0218950 A1 | 7/2023 | Belson et al. |
| 2023/0245747 A1 | 8/2023 | Rosenberg et al. |
| 2023/0245748 A1 | 8/2023 | Rosenberg et al. |
| 2023/0245750 A1 | 8/2023 | Rosenberg et al. |
| 2023/0245751 A1 | 8/2023 | Rosenberg et al. |
| 2023/0249599 A1 | 8/2023 | Nicola |
| 2023/0253089 A1 | 8/2023 | Rosenberg et al. |
| 2023/0255555 A1 | 8/2023 | Sundaram et al. |
| 2023/0263428 A1 | 8/2023 | Hull et al. |
| 2023/0274813 A1 | 8/2023 | Rosenberg et al. |
| 2023/0282329 A1 | 9/2023 | Mason et al. |
| 2023/0364472 A1 | 11/2023 | Posnack |
| 2023/0368886 A1 | 11/2023 | Rosenberg |
| 2023/0377710 A1 | 11/2023 | Chen et al. |
| 2023/0377711 A1 | 11/2023 | Rosenberg |
| 2023/0377712 A1 | 11/2023 | Rosenberg |
| 2023/0386639 A1 | 11/2023 | Rosenberg |
| 2023/0395231 A1 | 12/2023 | Rosenberg |
| 2023/0395232 A1 | 12/2023 | Rosenberg |
| 2024/0029856 A1 | 1/2024 | Rosenberg |

FOREIGN PATENT DOCUMENTS

| | | |
|---|---|---|
| CN | 101964151 A | 2/2011 |
| CN | 201889024 U | 7/2011 |
| CN | 202220794 U | 5/2012 |
| CN | 102670381 A | 9/2012 |
| CN | 103263336 A | 8/2013 |
| CN | 103390357 A | 11/2013 |
| CN | 103473631 A | 12/2013 |
| CN | 103488880 A | 1/2014 |
| CN | 103501328 A | 1/2014 |
| CN | 103721343 A | 4/2014 |
| CN | 203677851 U | 7/2014 |
| CN | 104335211 A | 2/2015 |
| CN | 104337668 A | 2/2015 |
| CN | 105263448 A | 1/2016 |
| CN | 105620643 A | 6/2016 |
| CN | 105683977 A | 6/2016 |
| CN | 103136447 B | 8/2016 |
| CN | 105894088 A | 8/2016 |
| CN | 105930668 A | 9/2016 |
| CN | 205626871 U | 10/2016 |
| CN | 106127646 A | 11/2016 |
| CN | 106236502 A | 12/2016 |
| CN | 106510985 A | 3/2017 |
| CN | 106621195 A | 5/2017 |
| CN | 107066819 A | 8/2017 |
| CN | 107430641 A | 12/2017 |
| CN | 107551475 A | 1/2018 |
| CN | 107736982 A | 2/2018 |
| CN | 107930021 A | 4/2018 |
| CN | 108078737 A | 5/2018 |
| CN | 208224811 A | 12/2018 |
| CN | 109191954 A | 1/2019 |
| CN | 109363887 A | 2/2019 |
| CN | 208573971 U | 3/2019 |
| CN | 209004370 U | 6/2019 |
| CN | 109968339 A | 7/2019 |
| CN | 110148472 A | 8/2019 |
| CN | 110201358 A | 9/2019 |
| CN | 110215188 A | 9/2019 |
| CN | 110322957 A | 10/2019 |
| CN | 110808092 A | 2/2020 |
| CN | 110931103 A | 3/2020 |
| CN | 110993057 A | 4/2020 |
| CN | 111105859 A | 5/2020 |
| CN | 111111110 A | 5/2020 |
| CN | 111370088 A | 7/2020 |
| CN | 111460305 A | 7/2020 |
| CN | 112071393 A | 12/2020 |
| CN | 212141371 U | 12/2020 |
| CN | 112289425 A | 1/2021 |
| CN | 212624809 U | 2/2021 |
| CN | 112603295 A | 4/2021 |
| CN | 213190965 U | 5/2021 |
| CN | 113384850 A | 9/2021 |
| CN | 113499572 A | 10/2021 |
| CN | 215136488 U | 12/2021 |
| CN | 113885361 A | 1/2022 |
| CN | 114049961 A | 2/2022 |
| CN | 114203274 A | 3/2022 |
| CN | 216258145 U | 4/2022 |
| CN | 114694824 A | 7/2022 |
| CN | 114898832 A | 8/2022 |
| CN | 114983760 A | 9/2022 |
| CN | 217472652 U | 9/2022 |
| CN | 110270062 B | 10/2022 |
| CN | 218420859 U | 2/2023 |
| CN | 115954081 A | 4/2023 |
| DE | 95019 C | 1/1897 |
| DE | 7628633 U1 | 12/1977 |
| DE | 8519150 U1 | 10/1985 |
| DE | 3732905 A1 | 7/1988 |
| DE | 4330269 A1 | 3/1995 |
| DE | 19619820 A1 | 12/1996 |
| DE | 29620008 U1 | 2/1997 |
| DE | 19947926 A1 | 4/2001 |
| DE | 102018202497 A1 | 8/2018 |
| DE | 102018211212 A1 | 1/2019 |
| DE | 102019108425 B3 | 8/2020 |
| EP | 199600 A2 | 10/1986 |
| EP | 0383137 A2 | 8/1990 |
| EP | 634319 A2 | 1/1995 |
| EP | 0919259 A1 | 6/1999 |
| EP | 1034817 A1 | 9/2000 |
| EP | 1159989 A1 | 12/2001 |
| EP | 1968028 | 9/2008 |
| EP | 2564904 A1 | 3/2013 |
| EP | 1909730 B1 | 4/2014 |
| EP | 2815242 A4 | 12/2014 |
| EP | 2869805 A | 5/2015 |
| EP | 2997951 A1 | 3/2016 |
| EP | 2688472 B1 | 4/2016 |
| EP | 3264303 A1 | 1/2018 |
| EP | 3323473 A1 | 5/2018 |
| EP | 3547322 A1 | 10/2019 |

(56) References Cited

FOREIGN PATENT DOCUMENTS

| | | |
|---|---|---|
| EP | 3627514 A1 | 3/2020 |
| EP | 3671700 A1 | 6/2020 |
| EP | 3688537 A1 | 8/2020 |
| EP | 3731733 A1 | 11/2020 |
| EP | 3984508 A1 | 4/2022 |
| EP | 3984509 A1 | 4/2022 |
| EP | 3984510 A1 | 4/2022 |
| EP | 3984511 A1 | 4/2022 |
| EP | 3984512 A1 | 4/2022 |
| EP | 3984513 A1 | 4/2022 |
| EP | 4054699 A1 | 9/2022 |
| EP | 4112033 A1 | 1/2023 |
| FR | 2527541 A2 | 12/1983 |
| FR | 3127393 A1 | 3/2023 |
| GB | 141664 A | 11/1920 |
| GB | 2336140 A | 10/1999 |
| GB | 2372459 A | 8/2002 |
| GB | 2512431 A | 10/2014 |
| GB | 2591542 B | 3/2022 |
| IN | 201811043670 A | 7/2018 |
| JP | 2000005339 A | 1/2000 |
| JP | 2003225875 A | 8/2003 |
| JP | 2005227928 A | 8/2005 |
| JP | 2005227928 A1 | 8/2005 |
| JP | 2009011517 A | 1/2009 |
| JP | 2009112336 A | 5/2009 |
| JP | 2013515995 A | 5/2013 |
| JP | 3193662 U | 10/2014 |
| JP | 3198173 U | 6/2015 |
| JP | 5804063 B2 | 11/2015 |
| JP | 2018102842 A | 7/2018 |
| JP | 2019028647 A | 2/2019 |
| JP | 2019134909 A | 8/2019 |
| JP | 6573739 B1 | 9/2019 |
| JP | 6659831 B2 | 3/2020 |
| JP | 2020057082 A | 4/2020 |
| JP | 6710357 B1 | 6/2020 |
| JP | 6775757 B1 | 10/2020 |
| JP | 2021027917 A | 2/2021 |
| JP | 6871379 B2 | 5/2021 |
| JP | 2022521378 A | 4/2022 |
| JP | 3238491 U | 7/2022 |
| JP | 7198364 B2 | 12/2022 |
| JP | 7202474 B2 | 1/2023 |
| JP | 7231750 B2 | 3/2023 |
| JP | 7231751 B2 | 3/2023 |
| JP | 7231752 B2 | 3/2023 |
| KR | 20020009724 A | 2/2002 |
| KR | 200276919 Y1 | 5/2002 |
| KR | 20020065253 A | 8/2002 |
| KR | 100582596 B1 | 5/2006 |
| KR | 101042258 B1 | 6/2011 |
| KR | 101258250 B1 | 4/2013 |
| KR | 101325581 B1 | 11/2013 |
| KR | 20140128630 A | 11/2014 |
| KR | 20150017693 A | 2/2015 |
| KR | 20150078191 A | 7/2015 |
| KR | 101580071 B1 | 12/2015 |
| KR | 101647620 B1 | 8/2016 |
| KR | 20160093990 A | 8/2016 |
| KR | 20170038837 A | 4/2017 |
| KR | 20180004928 A | 1/2018 |
| KR | 20190029175 A | 3/2019 |
| KR | 20190056116 A | 5/2019 |
| KR | 101988167 B1 | 6/2019 |
| KR | 101969392 B1 | 8/2019 |
| KR | 102055279 B1 | 12/2019 |
| KR | 102088333 B1 | 3/2020 |
| KR | 20200025290 A | 3/2020 |
| KR | 20200029180 A | 3/2020 |
| KR | 102116664 B1 | 5/2020 |
| KR | 102116968 B1 | 5/2020 |
| KR | 20200056233 A | 5/2020 |
| KR | 102120828 B1 | 6/2020 |
| KR | 102121586 B1 | 6/2020 |
| KR | 102142713 B1 | 8/2020 |
| KR | 102162522 B1 | 10/2020 |
| KR | 20200119665 A | 10/2020 |
| KR | 102173553 B1 | 11/2020 |
| KR | 102180079 B1 | 11/2020 |
| KR | 102188766 B1 | 12/2020 |
| KR | 102196793 B1 | 12/2020 |
| KR | 20210006212 A | 1/2021 |
| KR | 102224188 B1 | 3/2021 |
| KR | 102224618 B1 | 3/2021 |
| KR | 102246049 B1 | 4/2021 |
| KR | 102246050 B1 | 4/2021 |
| KR | 102246051 B1 | 4/2021 |
| KR | 102246052 B1 | 4/2021 |
| KR | 102264498 B1 | 6/2021 |
| KR | 102352602 B1 | 1/2022 |
| KR | 102352603 B1 | 1/2022 |
| KR | 102352604 B1 | 1/2022 |
| KR | 20220004639 A | 1/2022 |
| KR | 102387577 B1 | 4/2022 |
| KR | 102421437 B1 | 7/2022 |
| KR | 20220102207 A | 7/2022 |
| KR | 102427545 B1 | 8/2022 |
| KR | 102467495 B1 | 11/2022 |
| KR | 102467496 B1 | 11/2022 |
| KR | 102469723 B1 | 11/2022 |
| KR | 102471990 B1 | 11/2022 |
| KR | 20220145989 A | 11/2022 |
| KR | 20220156134 A | 11/2022 |
| KR | 102502744 B1 | 2/2023 |
| KR | 20230019349 A | 2/2023 |
| KR | 20230019350 A | 2/2023 |
| KR | 20230026556 A | 2/2023 |
| KR | 20230026668 A | 2/2023 |
| KR | 20230040526 | 3/2023 |
| KR | 20230050506 A | 4/2023 |
| KR | 20230056118 A | 4/2023 |
| KR | 102528503 B1 | 5/2023 |
| KR | 102531930 B1 | 5/2023 |
| KR | 102532766 B1 | 5/2023 |
| KR | 102539190 B1 | 6/2023 |
| RU | 2014131288 A | 2/2016 |
| RU | 2607953 C2 | 1/2017 |
| TW | M474545 U | 3/2014 |
| TW | I442956 B | 7/2014 |
| TW | M638437 U | 3/2023 |
| WO | 1998009687 A1 | 3/1998 |
| WO | 0149235 A2 | 7/2001 |
| WO | 0151083 A2 | 7/2001 |
| WO | 2001050387 A1 | 7/2001 |
| WO | 2001056465 A1 | 8/2001 |
| WO | 02093312 A2 | 11/2002 |
| WO | 2003043494 A1 | 5/2003 |
| WO | 2005018453 A1 | 3/2005 |
| WO | 2005074369 A2 | 8/2005 |
| WO | 2006004430 A2 | 1/2006 |
| WO | 2006012694 A1 | 2/2006 |
| WO | 2007102709 A1 | 9/2007 |
| WO | 2008114291 A1 | 9/2008 |
| WO | 2009003170 A1 | 12/2008 |
| WO | 2011025322 A2 | 3/2011 |
| WO | 2012128801 A1 | 9/2012 |
| WO | 2013002568 A2 | 1/2013 |
| WO | 2023164292 A1 | 3/2013 |
| WO | 2013122839 A1 | 8/2013 |
| WO | 2014011447 A1 | 1/2014 |
| WO | 2014163976 A1 | 10/2014 |
| WO | 2015026744 A1 | 2/2015 |
| WO | 2015065298 A1 | 5/2015 |
| WO | 2015082555 A1 | 6/2015 |
| WO | 2016154318 A1 | 9/2016 |
| WO | 2017030781 A1 | 2/2017 |
| WO | 2017091691 A1 | 6/2017 |
| WO | 2017165238 A1 | 9/2017 |
| WO | 2018081795 A1 | 5/2018 |
| WO | 2018171853 A1 | 9/2018 |
| WO | 2019022706 A1 | 1/2019 |
| WO | 2019083450 A1 | 5/2019 |
| WO | 2019143940 A1 | 7/2019 |

(56) References Cited

FOREIGN PATENT DOCUMENTS

| | | |
|---|---|---|
| WO | 2020075190 A1 | 4/2020 |
| WO | 2020130979 A1 | 6/2020 |
| WO | 2020149815 A2 | 7/2020 |
| WO | 2020245727 A1 | 12/2020 |
| WO | 2020249855 A1 | 12/2020 |
| WO | 2020252599 A1 | 12/2020 |
| WO | 2020256577 A1 | 12/2020 |
| WO | 2021021447 A1 | 2/2021 |
| WO | 2021038980 A1 | 3/2021 |
| WO | 2021055427 A1 | 3/2021 |
| WO | 2021061061 A1 | 4/2021 |
| WO | 2021090267 A1 | 5/2021 |
| WO | 2021138620 A1 | 7/2021 |
| WO | 2021236961 A1 | 11/2021 |
| WO | 2022047006 A1 | 3/2022 |
| WO | 2022092493 A1 | 5/2022 |
| WO | 2022092494 A1 | 5/2022 |
| WO | 2022212883 A1 | 10/2022 |
| WO | 2022212921 A1 | 10/2022 |
| WO | 2022216498 A1 | 10/2022 |
| WO | 2022251420 A1 | 12/2022 |
| WO | 2023008680 A1 | 2/2023 |
| WO | 2023008681 A1 | 2/2023 |
| WO | 2023022319 A1 | 2/2023 |
| WO | 2023022320 A1 | 2/2023 |
| WO | 2023052695 A1 | 4/2023 |
| WO | 2023091496 A1 | 5/2023 |
| WO | 2023215155 A1 | 11/2023 |
| WO | 2023230075 A1 | 11/2023 |
| WO | 2024013267 A1 | 1/2024 |
| WO | 2024107807 A1 | 5/2024 |

OTHER PUBLICATIONS

Alex Bellec, "Part-of-Speech tagging tutorial with the Keras Deep Learning library," pp. 1-16, published Mar. 27, 2018, retrieved on Feb. 1, 2022 from https://becominghuman.ai/part-of-speech-tagging-tutorial-with-the-keras-deep-learning-library-d7f93fa05537.

Kavita Ganesan, All you need to know about text preprocessing for NLP and Machine Learning, pp. 1-14, published Feb. 23, 2019, retrieved on Feb. 1, 2022 from https://towardsdatascience.com/all-you-need-to-know-about-text-preprocessing-for-nlp-and-machine-learning-bc1c5765ff67.

Badreesh Shetty, "Natural Language Processing (NPL) for Machine Learning," pp. 1-13, published Nov. 24, 2018, retrieved on Feb. 1, 2022 from https://towardsdatascience.com/natural-language-processing-nlp-for-machine-learning-d44498845d5b.

Davenport et al., "The Potential For Artificial Intelligence In Healthcare", 2019, Future Healthcare Journal 2019, vol. 6, No. 2: Year: 2019, pp. 1-5.

Ahmed et al., "Artificial Intelligence With Multi-Functional Machine Learning Platform Development For Better Healthcare And Precision Medicine", 2020, Database (Oxford), 2020:baaa010. doi: 10.1093/database/baaa010 (Year: 2020), pp. 1-35.

Ruiz Ivan et al., "Towards a physical rehabilitation system using a telemedicine approach", Computer Methods in Biomechanics and Biomedical Engineering: Imaging & Visualization, vol. 8, No. 6, Jul. 28, 2020, pp. 671-680, XP055914810.

De Canniere Helene et al., "Wearable Monitoring and Interpretable Machine Learning Can Objectively Track Progression in Patients during Cardiac Rehabilitation", Sensors, vol. 20, No. 12, Jun. 26, 2020, XP055914617, pp. 1-15.

Boulanger Pierre et al., "A Low-cost Virtual Reality Bike for Remote Cardiac Rehabilitation", Dec. 7, 2017, Advances in Biometrics: International Conference, ICB 2007, Seoul, Korea, pp. 155-166.

Yin Chieh et al., "A Virtual Reality-Cycling Training System for Lower Limb Balance Improvement", BioMed Research International, vol. 2016, pp. 1-10.

Malloy, Online Article "AI-enabled EKGs find difference between numerical age and biological age significantly affects health, longevity", Website: https://newsnetwork.mayoclinic.org/discussion/ai-enabled-ekgs-find-difference-between-numerical-age-and-biological-age-significantly-affects-health-longevity/, Mayo Clinic News Network, May 20, 2021, retrieved: Jan. 23, 2023, p. 1-4.

Website for "Pedal Exerciser", p. 1, retrieved on Sep. 9, 2022 from https://www.vivehealth.com/collections/physical-therapy-equipment/products/pedalexerciser.

Website for "Functional Knee Brace with ROM", p. 1, retrieved on Sep. 9, 2022 from http://medicalbrace.gr/en/product/functional-knee-brace-with-goniometer-mbtelescopicknee/.

Website for "ComfySplints Goniometer Knee", pp. 1-5, retrieved on Sep. 9, 2022 from https://www.comfysplints.com/product/knee-splints/.

Website for "BMI FlexEze Knee Corrective Orthosis (KCO)", pp. 1-4, retrieved on Sep. 9, 2022 from https://orthobmi.com/products/bmi-flexeze%C2%AE-knee-corrective-orthosis-kco.

Website for "Neoprene Knee Brace with goniometer—Patella ROM MB.4070", pp. 1-4, retrieved on Sep. 9, 2022 from https://www.fortuna.com.gr/en/product/neoprene-knee-brace-with-goniometer-patella-rom-mb-4070/.

Kuiken et al., "Computerized Biofeedback Knee Goniometer: Acceptance and Effect on Exercise Behavior in Post-total Knee Arthroplasty Rehabilitation," Biomedical Engineering Faculty Research and Publications, 2004, pp. 1-10.

Ahmed et al., "Artificial intelligence with multi-functional machine learning platform development for better healthcare and precision medicine," Database, 2020, pp. 1-35.

Davenport et al., "The potential for artificial intelligence in healthcare," Digital Technology, Future Healthcare Journal, 2019, pp. 1-5, vol. 6, No. 2.

Website for "OxeFit XS1", pp. 1-3, retrieved on Sep. 9, 2022 from https://www.oxefit.com/xs1.

Website for "Preva Mobile", pp. 1-6, retrieved on Sep. 9, 2022 from https://www.precor.com/en-us/resources/introducing-preva-mobile.

Website for "J-Bike", pp. 1-3, retrieved on Sep. 9, 2022 from https://www.magneticdays.com/en/cycling-for-physical-rehabilitation.

Website for "Excy", pp. 1-12, retrieved on Sep. 9, 2022 from https://excy.com/portable-exercise-rehabilitation-excy-xcs-pro/.

Website for "OxeFit XP1", p. 1, retrieved on Sep. 9, 2022 from https://www.oxefit.com/xp1.

Alcaraz et al., "Machine Learning as Digital Therapy Assessment for Mobile Gait Rehabilitation," 2018 IEEE 28th International Workshop on Machine Learning for Signal Processing (MLSP), Aalborg, Denmark, 2018, 6 pages.

Androutsou et al., "A Smartphone Application Designed to Engage the Elderly in Home-Based Rehabilitation," Frontiers in Digital Health, Sep. 2020, vol. 2, Article 15, 13 pages.

Silva et al., "SapoFitness: A mobile health application for dietary evaluation," 2011 IEEE 13th International Conference on U e-Health Networking, Applications and Services, Columbia, MO, USA, 2011, 6 pages.

Wang et al., "Interactive wearable systems for upper body rehabilitation: a systematic review," Journal of NeuroEngineering and Rehabilitation, 2017, 21 pages.

Marzolini et al., "Eligibility, Enrollment, and Completion of Exercise-Based Cardiac Rehabilitation Following Stroke Rehabilitation: What Are the Barriers?," Physical Therapy, vol. 100, No. 1, 2019, 13 pages.

Nijjar et al., "Randomized Trial of Mindfulness-Based Stress Reduction in Cardiac Patients Eligible for Cardiac Rehabilitation," Scientific Reports, 2019, 12 pages.

Lara et al., "Human-Robot Sensor Interface for Cardiac Rehabilitation," IEEE International Conference on Rehabilitation Robotics, Jul. 2017, 8 pages.

Ishraque et al., "Artificial Intelligence-Based Rehabilitation Therapy Exercise Recommendation System," 2018 IEEE MIT Undergraduate Research Technology Conference (URTC), Cambridge, MA, USA, 2018, 5 pages.

Zakari et al., "Are There Limitations to Exercise Benefits in Peripheral Arterial Disease?," Frontiers in Cardiovascular Medicine, Nov. 2018, vol. 5, Article 173, 12 pages.

(56) References Cited

OTHER PUBLICATIONS

You et al., "Including Blood Vasculature into a Game-Theoretic Model of Cancer Dynamics," Games 2019, 10, 13, 22 pages.
Jeong et al., "Computer-assisted upper extremity training using interactive biking exercise (iBikE) platform," Sep. 2012, 34th Annual International Conference of the IEEE Embs, 5 pages.
Chrif et al., "Control design for a lower-limb paediatric therapy device using linear motor technology," Article, 2017, pp. 119-127, Science Direct, Switzerland.
Robben et al., "Delta Features From Ambient Sensor Data are Good Predictors of Change in Functional Health," Article, 2016, pp. 2168-2194, vol. 21, No. 4, IEEE Journal of Biomedical and Health Informatics.
Kantoch et al., "Recognition of Sedentary Behavior by Machine Learning Analysis of Wearable Sensors during Activities of Daily Living for Telemedical Assessment of Cardiovascular Risk," Article, 2018, 17 pages, Sensors, Poland.
Warburton et al., "International Launch of the PAR-•Q+ and ePARmed-•X+ Validation of the PAR-•Q+ and ePARmed••X+," Health & Fitness Journal of Canada, 2011, 9 pages, vol. 4, No. 2.
HCL Fitness, HCI Fitness PhysioTrainer Pro, 2017, retrieved on Aug. 19, 2021, 7 pages, https://www.amazon.com/HCI-Fitness-Physio Trainer-Electronically-Controlled/dp/B0759YMW78/.
International Searching Authority, International Preliminary Report on Patentability of International Application No. PCT/US2017/50895, Date of Mailing Dec. 11, 2018, 52 pages.
International Searching Authority, Search Report and Written Opinion for International Application No. PCT/US2017/50895, Date of Mailing Jan. 12, 2018, 6 pages.
International Searching Authority, Search Report and Written Opinion for International Application No. PCT/US2020/021876, Date of Mailing May 28, 2020, 8 pages.
International Searching Authority, Search Report and Written Opinion for International Application No. PCT/US2020/051008, Date of Mailing Dec. 10, 2020, 9 pages.
International Searching Authority, Search Report and Written Opinion for International Application No. PCT/US2020/056661, Date of Mailing Feb. 12, 2021, 12 pages.
International Searching Authority, Search Report and Written Opinion for International Application No. PCT/US2021/032807, Date of Mailing Sep. 6, 2021, 11 pages.
Matrix, R3xm Recumbent Cycle, retrieved on Aug. 4, 2020, 7 pages, https://www.matrixfitness.com/en/cardio/cycles/r3xm-recumbent.
ROM3 Rehab, ROM3 Rehab System, Apr. 20, 2015, retrieved on Aug. 31, 2018, 12 pages, https://vimeo.com/125438463.
International Search Report and Written Opinion for PCT/US2023/014137, dated Jun. 9, 2023, 13 pages.
Website for "Esino 2022 Physical Therapy Equipments Arm Fitness Indoor Trainer Leg Spin Cycle Machine Exercise Bike for Elderly," https://www.made-in-china.com/showroom/esinogroup/product-detailYdZtwGhCMKVR/China-Esino-2022-Physical-Therapy-Equipments-Arm-Fitness-Indoor-Trainer-Leg-Spin-Cycle-Machine-Exercise-Bike-for-Elderly.html, retrieved on Aug. 29, 2023, 5 pages.
Abedtash, "An Interoperable Electronic Medical Record-Based Platform For Personalized Predictive Analytics", ProQuest LLC, Jul. 2017, 185 pages.
Gerbild et al., "Physical Activity to Improve Erectile Dysfunction: A Systematic Review of Intervention Studies," Sexual Medicine, 2018, 15 pages.
Barrett et al., "Artificial intelligence supported patient self-care in chronic heart failure: a paradigm shift from reactive to predictive, preventive and personalised care," EPMA Journal (2019), pp. 445-464.
Oerkild et al., "Home-based cardiac rehabilitation is an attractive alternative to no cardiac rehabilitation for elderly patients with coronary heart disease: results from a randomised clinical trial," BMJ Open Accessible Medical Research, Nov. 22, 2012, pp. 1-9.
Bravo-Escobar et al., "Effectiveness and safety of a home-based cardiac rehabilitation programme of mixed surveillance in patients with ischemic heart disease at moderate cardiovascular risk: A randomised, controlled clinical trial," BMC Cardiovascular Disorders, 2017, pp. 1-11, vol. 17:66.
Thomas et al., "Home-Based Cardiac Rehabilitation," Circulation, 2019, pp. e69-e89, vol. 140.
Thomas et al., "Home-Based Cardiac Rehabilitation," Journal of the American College of Cardiology, Nov. 1, 2019, pp. 133-153, vol. 74.
Thomas et al., "Home-Based Cardiac Rehabilitation," HHS Public Access, Oct. 2, 2020, pp. 1-39.
Dittus et al., "Exercise-Based Oncology Rehabilitation: Leveraging the Cardiac Rehabilitation Model," Journal of Cardiopulmonary Rehabilitation and Prevention, 2015, pp. 130-139, vol. 35.
Chen et al., "Home-based cardiac rehabilitation improves quality of life, aerobic capacity, and readmission rates in patients with chronic heart failure," Medicine, 2018, pp. 1-5 vol. 97:4.
Lima de Melo Ghisi et al., "A systematic review of patient education in cardiac patients: Do they increase knowledge and promote health behavior change?," Patient Education and Counseling, 2014, pp. 1-15.
Fang et al., "Use of Outpatient Cardiac Rehabilitation Among Heart Attack Survivors—20 States and the District of Columbia, 2013 and Four States, 2015," Morbidity and Mortality Weekly Report, vol. 66, No. 33, Aug. 25, 2017, pp. 869-873.
Beene et al., "AI and Care Delivery: Emerging Opportunities For Artificial Intelligence To Transform How Care Is Delivered," Nov. 2019, American Hospital Association, pp. 1-12.
Website for iFit ActivePulse™: Personalized and Automatic Heart Rate Training, retrieved on Jul. 15, 2024, URL—https://web.archive.org/web/20210616201402/https://www.nordictrack.com/learn/ifit-activepulse/, 4 pages.
Jeong et al., "Computer-assisted upper extremity training using interactive biking exercise (iBikE) platform," Sep. 2012, pp. 1-5, 34th Annual International Conference of the IEEE EMBS.
Thimo et al., "Effect of self tailored high-intensity interval training versus moderate-intensity continuous exercise of cardiorespiratory fitness after myocardial infarction: A randomised controlled trial," Nov. 2020, 8 pages, Switzerland.

\* cited by examiner

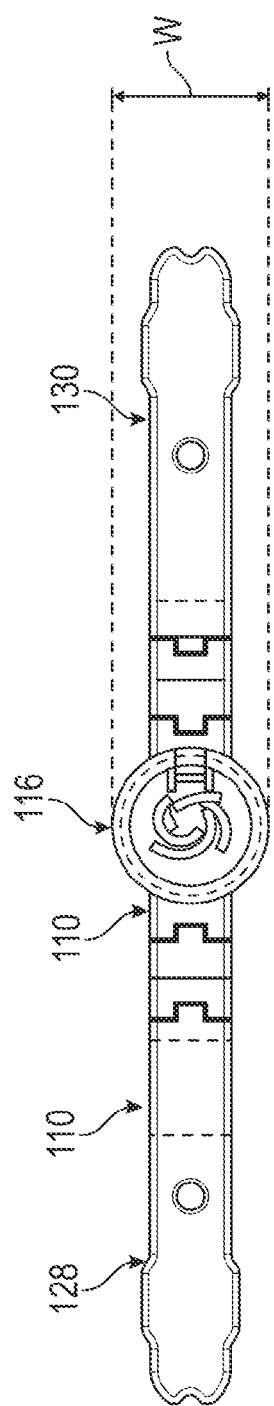
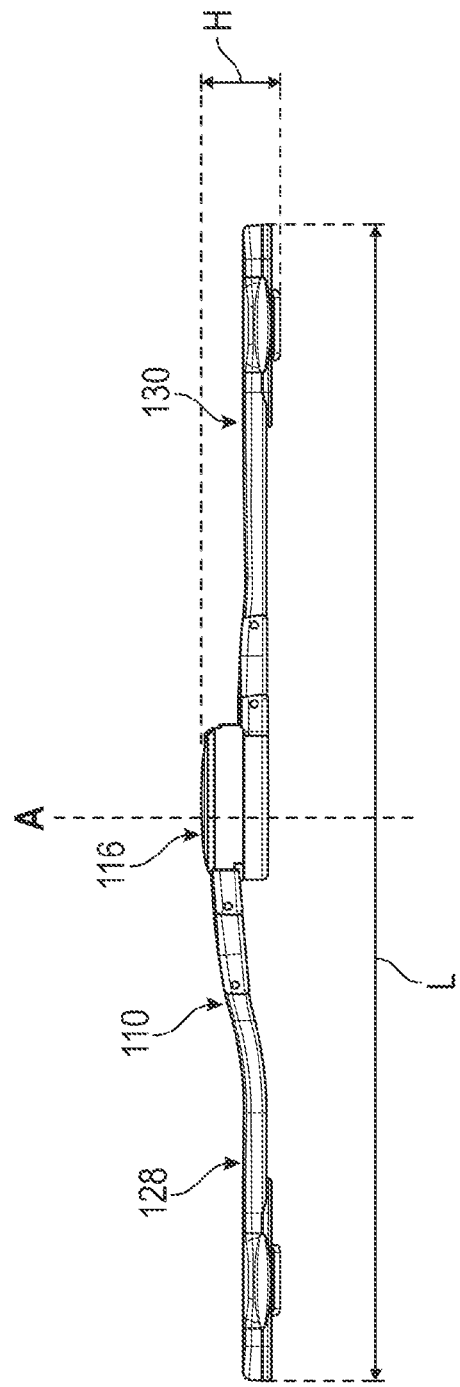
FIG. 3A
FIG. 3B

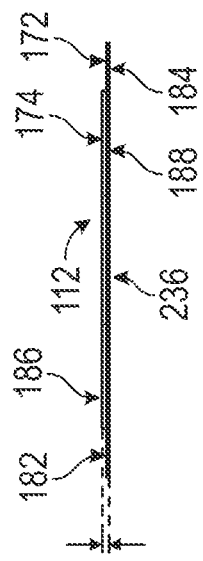
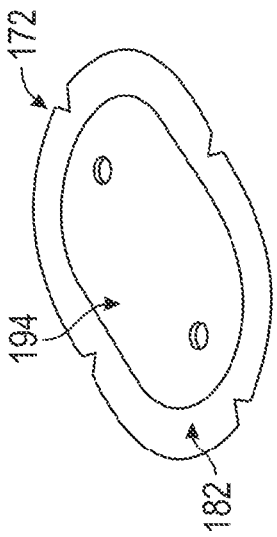
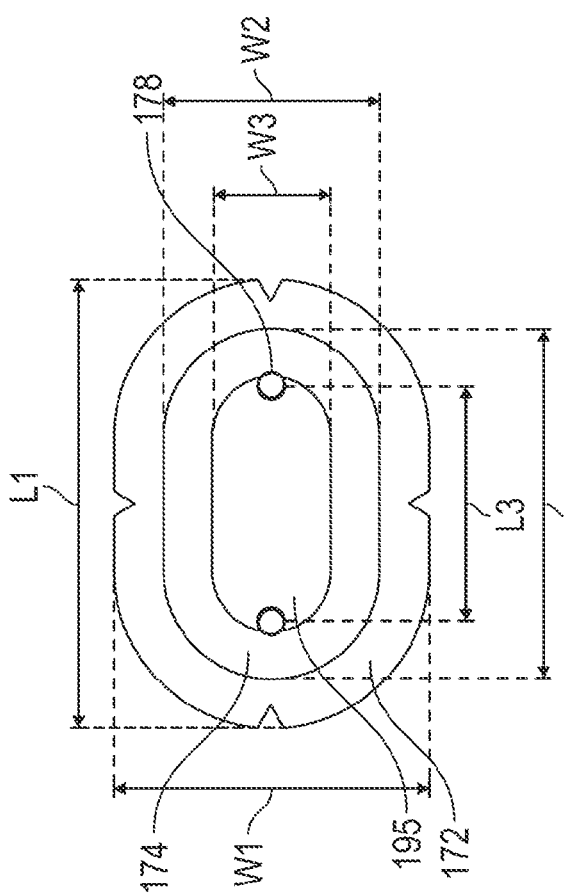
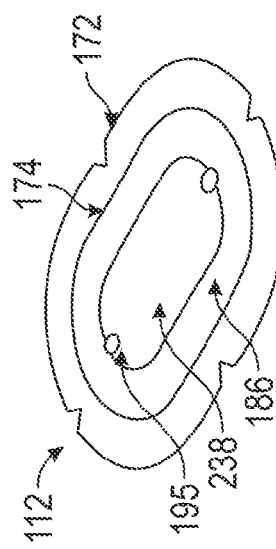
FIG. 9B
FIG. 9D
FIG. 9A
FIG. 9C

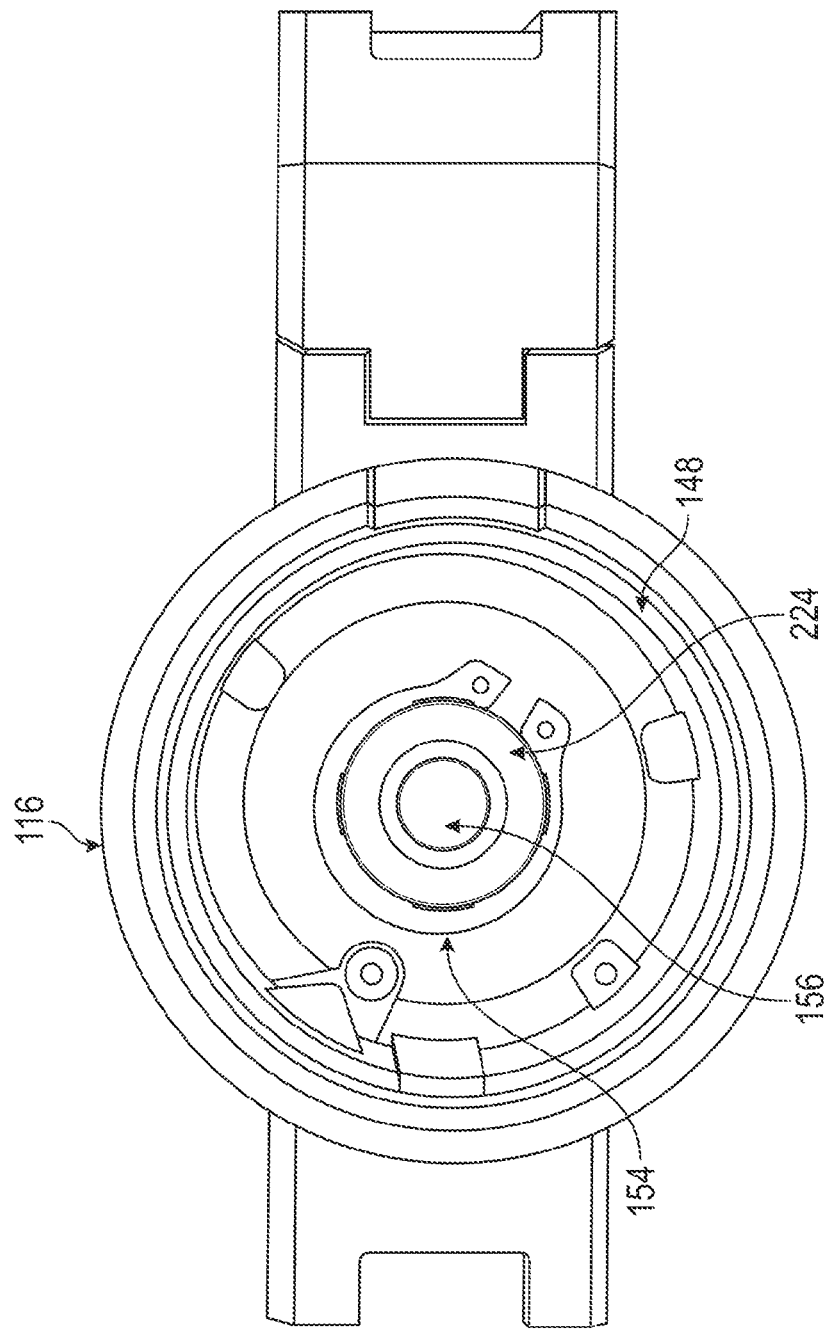

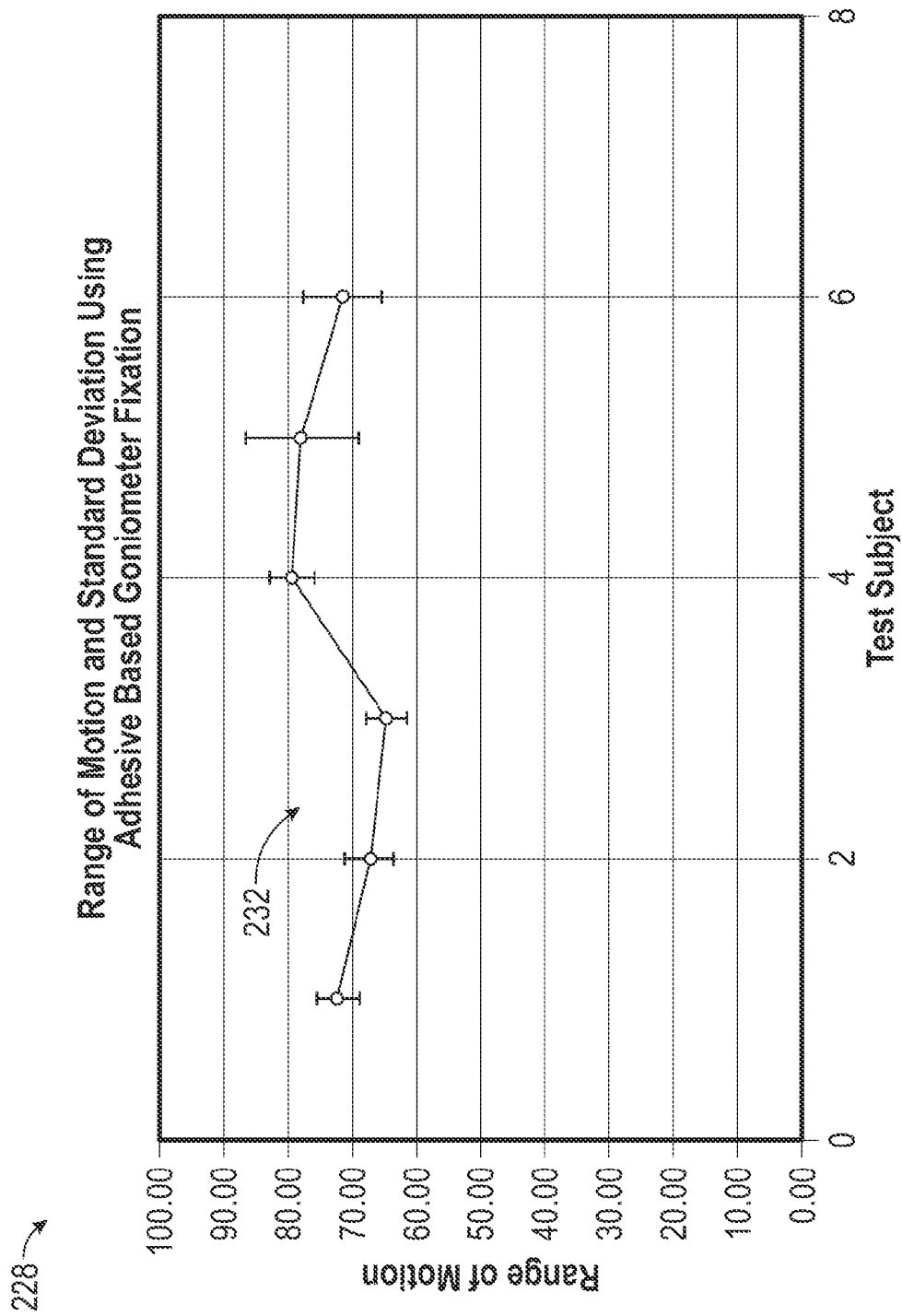

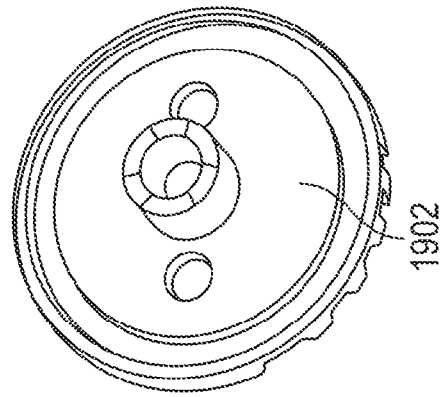
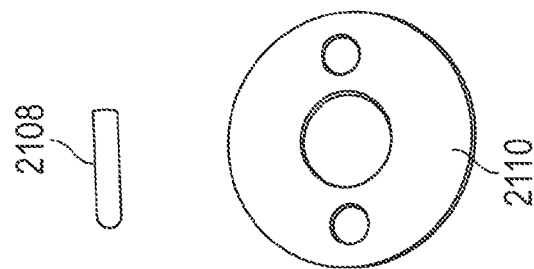
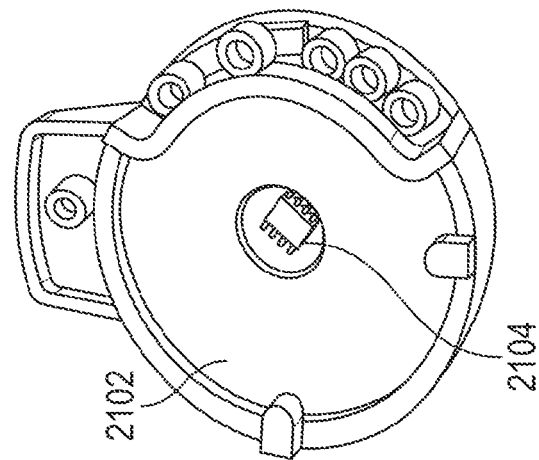
FIG. 21

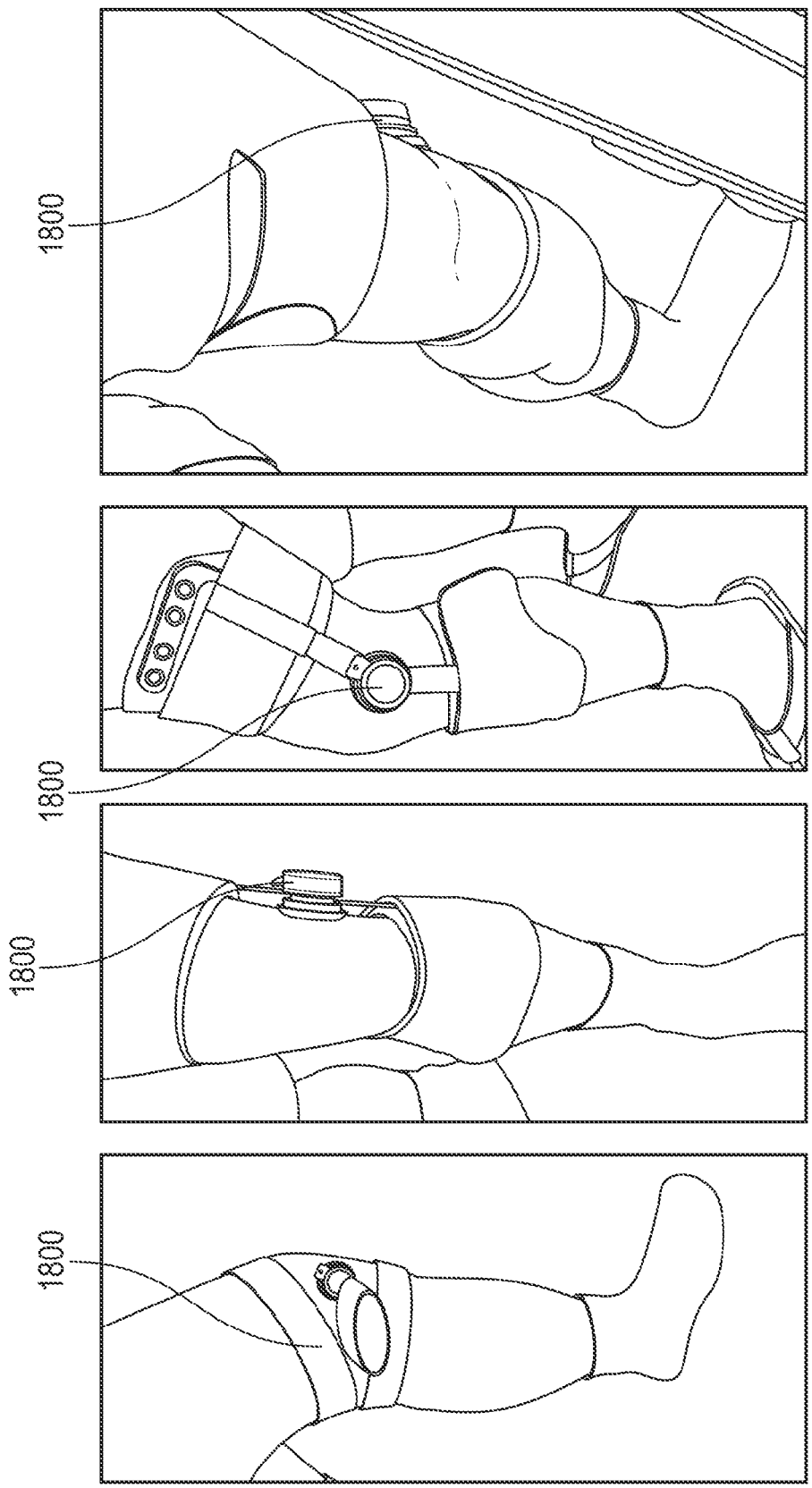

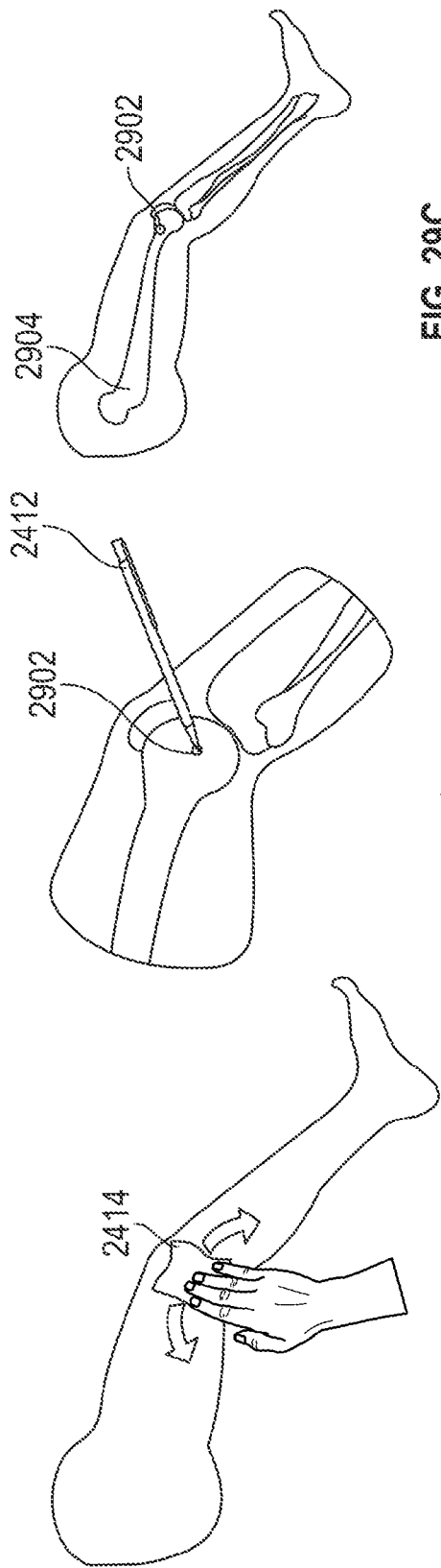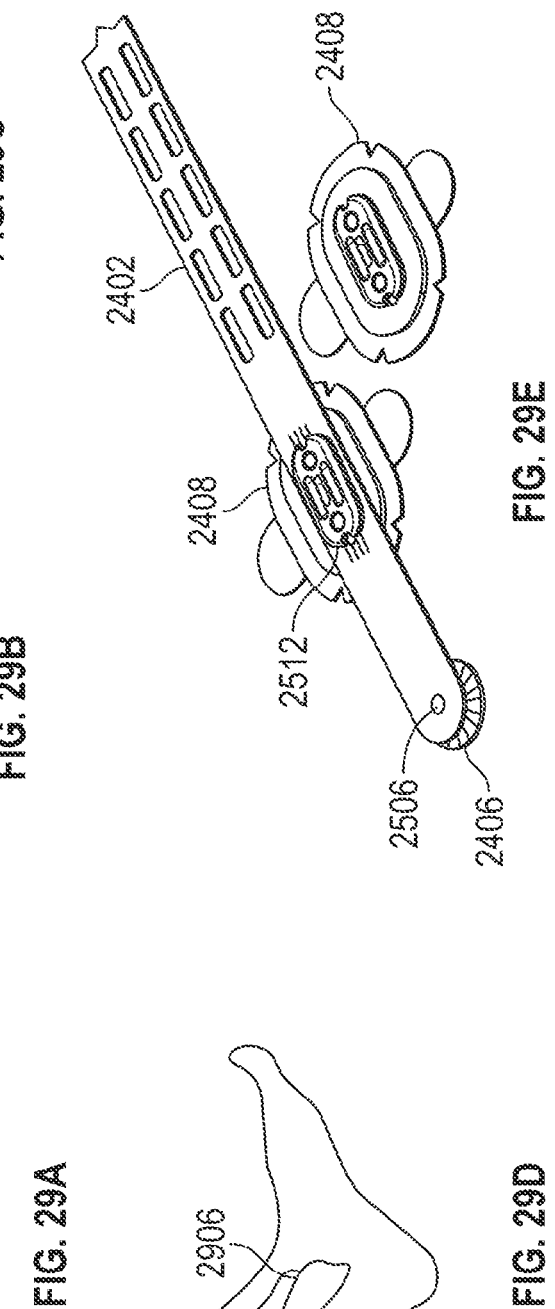

SYSTEM, METHOD AND APPARATUS FOR ANCHORING AN ELECTRONIC DEVICE AND MEASURING A JOINT ANGLE

CROSS-REFERENCE TO RELATED APPLICATION

This present application is a national stage application of International Patent Application No. PCT/US2021/038617, filed Jun. 23, 2021, which claims priority to and the benefit of U.S. Provisional Patent Application No. 63/044,625, filed Jun. 26, 2020, and U.S. Provisional Patent Application No. 63/123,301, filed Dec. 9, 2020, each of which is incorporated herein by reference in their entireties.

TECHNICAL FIELD

This disclosure generally relates to a system, apparatus and method of attaching a goniometer adjacent to a knee of a user.

BACKGROUND

A patient often requires physical therapy to recover from surgery or an injury, such as a knee replacement surgery. The physical therapy can include exercise to increase the patient's strength and flexibility. If a patient over-extends his or her muscles or joints, the muscles or joints, surrounding tissues or repaired tissues may become further injured. If a patient does not exercise his or her muscles or joints to gain the appropriate range of motion, the joint may become stiff and require additional surgery. Measuring and monitoring the range of motion during physical therapy can help prevent further injury to the patient and result in a faster recovery time.

A goniometer is an instrument that can be used to measure ranges of motion or joint angles of a patient's body. A standard goniometer consists of a stationary arm that cannot move independently, a moving arm attached to a fulcrum in the center of a body, and the body being a protractor of which 0 to 180 or 360 degrees are drawn. The stationary arm is attached to one limb or part of the patient's body (e.g., a thigh) and the moving arm is attached to another limb or part of the patient's body (e.g., a lower leg). The fulcrum can be a rivet or screw-like device at the center of the body that allows the moving arm to move freely on the body of the device in order for a clinician to obtain a measurement of the angle of movement of the patient's joint (e.g., a knee). The measurements can be used to track progress in a rehabilitation program. Each time a patient has a rehabilitation session, the clinician places or attaches the goniometer device onto the patient using straps, for example. The patient may have different clinicians setting up the goniometer device and measuring the joint movement. Based on the experience of the clinician, the goniometer may be attached onto different locations on the patient, which can affect the accuracy of the measurements. The accuracy of the repeated measurements also may be compromised due to issues with the device. Further, if the goniometer has never been attached to the patient, or if the goniometer is detached and needs to be reapplied, improper placement of the goniometer and any supporting devices may cause improper readings, thereby reducing the utility of having a goniometer.

Often, the patient needs additional support for their knee. A knee brace is often used to provide that support. In some examples, the knee brace may include a means of limiting the range of motion of the knee. Accordingly, improvements in such equipment and methods continue to be of interest.

SUMMARY

Embodiments of a system, apparatus and method of attaching a goniometer adjacent to a knee of a user are disclosed. For example, a method of installing devices on a user can include locating a lateral epicondyle at a knee of the user and indicating same to define a knee indicator; installing a knee pivot anchor at the knee indicator; locating a greater trochanter at a hip of the user and indicating same to define a hip indicator; locating a lateral malleolus at an ankle of the user and indicating same to define an ankle indicator; mounting a proximal portion of a template to the knee pivot anchor, pivoting the template about the knee pivot anchor, and aligning a distal portion of the template with the hip dot; placing a first pod in an aperture of the template and, with the distal portion of the template aligned with the hip dot, securing the first pod to a proximal location on the user; pivoting the template about the knee pivot anchor and aligning the distal portion of the template with the ankle dot; placing a second pod in the aperture of the template and, with the distal portion of the template aligned with the ankle dot, securing the second pod to a distal location on the user; and removing the template and the knee pivot anchor from the user.

In other embodiments, a kit for installing devices on a user can include an indicator set comprising a marker configured to place markings on the user, and a set of adhesive pads configured to be placed on the user; a knee pivot anchor configured to be attached to the user; a template having a proximal portion configured to be pivotally mounted to the knee pivot anchor, a distal portion configured to be positioned at different locations on the user, and an aperture; a set of pods configured to be interchangeably located in the aperture of the template, and each pod is configured to be secured to respective locations on the user; and the template and the knee pivot anchor can be configured to be removed from the user with the pods remaining in place on the user.

This section provides a general summary of the present disclosure and is not a comprehensive disclosure of its full scope or all of its features, aspects, and objectives.

BRIEF DESCRIPTION OF THE DRAWINGS

The disclosure is best understood from the following detailed description when read in conjunction with the accompanying drawings. It is emphasized that, according to common practice, the various features of the drawings are not to scale. On the contrary, the dimensions of the various features are arbitrarily expanded or reduced for clarity.

For a detailed description of example embodiments, reference will now be made to the accompanying drawings in which:

FIGS. 3A and 3B are top and side views of a goniometer in accordance with aspects of the present disclosure.

FIGS. 9A-D are views of first and second layers of the attachment in accordance with aspects of the present disclosure.

FIGS. 14A-C are perspective and top views of a center hub of the goniometer closed, open, and with components removed in accordance with aspects of the present disclosure.

FIGS. 16A and 16B are graphs illustrating test data in accordance with aspects of the present disclosure.

FIG. 21 is picture view of components of the knee brace of FIG. 18 in accordance with aspects of the present disclosure.

FIGS. 22A-22D are picture views of an embodiment of the knee brace in operation on a user in accordance with aspects of the present disclosure.

FIGS. 29A-29L illustrate individual steps of an embodiment of the method of FIGS. 28A-28C in accordance with aspects of the present disclosure.

NOTATION AND NOMENCLATURE

Figure 1A:
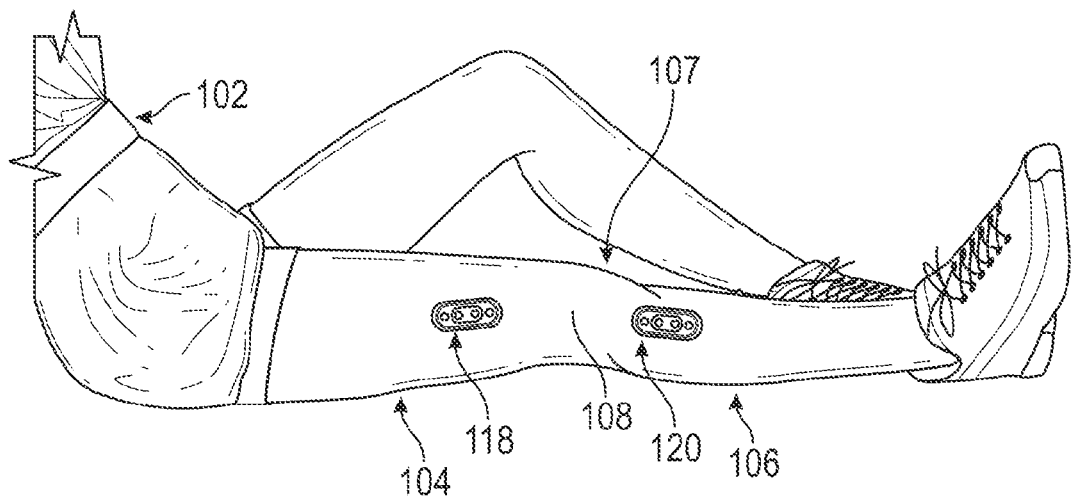
FIGS. 1A and 1B are side views of a wearable device for measuring and recording movement as placed on a user in accordance with aspects of the present disclosure.

Various terms are used to refer to particular system components. Different companies may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

The terminology used herein is for the purpose of describing particular example embodiments only, and is not intended to be limiting. As used herein, the singular forms "a," "an," and "the" may be intended to include the plural forms as well, unless the context clearly indicates otherwise. The method steps, processes, and operations described herein are not to be construed as necessarily requiring their performance in the particular order discussed or illustrated, unless specifically identified as an order of performance. It is also to be understood that additional or alternative steps may be employed.

The terms first, second, third, etc. may be used herein to describe various elements, components, regions, layers and/or sections; however, these elements, components, regions, layers and/or sections should not be limited by these terms. These terms may be only used to distinguish one element, component, region, layer or section from another region, layer or section. Terms such as "first," "second," and other numerical terms, when used herein, do not imply a sequence or order unless clearly indicated by the context. Thus, a first element, component, region, layer or section discussed below could be termed a second element, component, region, layer or section without departing from the teachings of the example embodiments. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C. In another example, the phrase "one or more"

when used with a list of items means there may be one item or any suitable number of items exceeding one.

Spatially relative terms, such as "inner," "outer," "beneath," "below," "lower," "above," "upper," "top," "bottom," and the like, may be used herein. These spatially relative terms can be used for ease of description to describe one element's or feature's relationship to another element(s) or feature(s) as illustrated in the figures. The spatially relative terms may also be intended to encompass different orientations of the device in use, or operation, in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptions used herein interpreted accordingly.

DETAILED DESCRIPTION

The following discussion is directed to various embodiments of the disclosure. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Figure 1B:
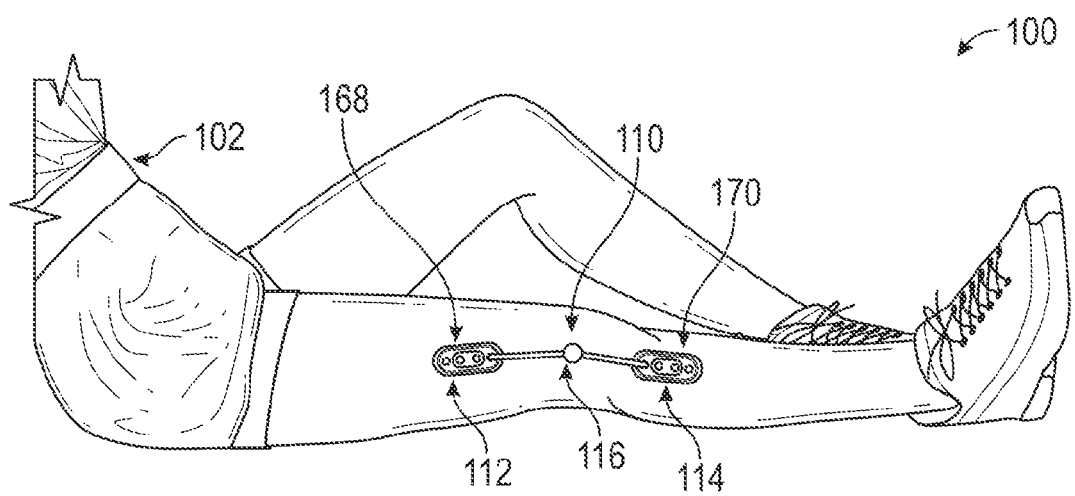
Figure 2A:
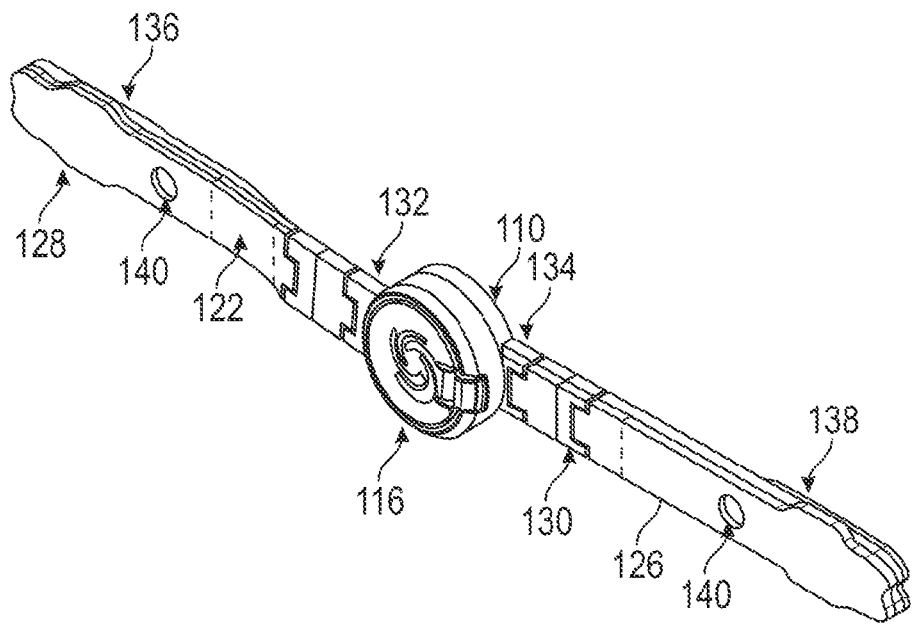
FIGS. 2A and 2B are top and bottom perspective views of a goniometer in accordance with aspects of the present disclosure.
Figure 2B:
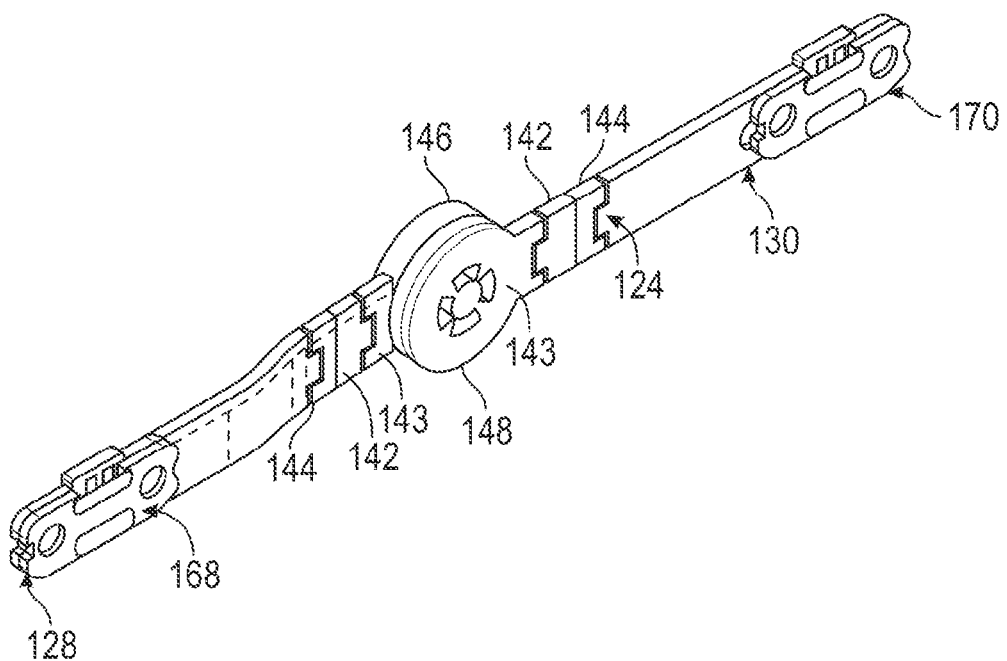

In accordance with aspects of the present disclosure, FIGS. 1A and 1B illustrate an exemplary system or wearable device 100, such as a goniometer, for measuring and recording flexion and extension at a joint 107 of a user 102. The wearable device 100 comprises first and second coupling apparatuses, or attachments, 112, 114, 118, 120 (hereinafter referred to as first and second attachments 118, 120) and may be configured to be removably coupled to the user 102 at opposing limb portions 104, 106 of the joint 107. For example, and as illustrated in FIGS. 1A and 1B, the first and second attachments 118, 120 may be coupled to a leg of a user at opposing limb portions 104, 106, e.g., thigh 104, and calf 106, of the knee or joint 107 of the user 102. As will be appreciated by those of skill in the art, the first and second attachments 118, 120 may be coupled to the user at opposing limb portions of any other joint of a patient or user 102. It is further contemplated that the wearable device 100 may be utilized for measuring flexion and extension of joints in animals, a joint of a robot, or any other desired joint or joint equivalent.

To position the wearable device 100 relative to the joint 107, a person, such as a clinician, may identify a joint center 108, where the joint center 108 may be used to align the wearable device 100 to the joint 107. The clinician may use an alignment device to identify and mark the joint center 108. For example, the alignment device may be used to mark the skin of the user 102 at the joint center 108 with a marker, pen, or any other desired tool. Further, the alignment device may be used to identify and mark positions at opposing limb portions 104, 106 for the first and second attachments 118, 120 relative to the joint center.

With reference to FIGS. 2A-6, the wearable device 100 comprises an exemplary device or apparatus 110, such as a goniometer. Hereinafter, the device or apparatus 110 may be referred to as a goniometer 110. The goniometer 110 is configured to measure the angular flexion and extension at the joint 107 of the user 102. The goniometer 110 has a top 122, a bottom 124, and opposing sides 126. The goniometer 110 may comprise a center hub 116 aligned coaxially with an axis A, and first and second arms 128, 130, wherein the arms 128, 130 couple to, and are pivotable or rotatable about, the axis A and the center hub 116. More specifically, first and second inner ends 132, 134 of the respective arms 128, 130 couple to the center hub 116. The arms 128, 130 extend outwardly from the center hub 116 to respective first and second outer ends 168, 170. In an alternative embodiment, the arms 128, 130 may be integrally formed with the center hub 116. Embodiments of the goniometer can enable various rotational or pivotal motions, such as with an axle, a rack and pinion system, etc.

With reference to FIGS. 3A and 3B, the goniometer 110 can have a length L that extends from the first outer end 136 to the second outer end 138. The length L can vary depending on the relative position of the first and second arms 128, 130. For example, a maximum length L of the goniometer 110 may be measured when the arms 128, 130 are positioned opposing one another. Whereas, when the arms 128, 130 are positioned parallel, and respectively directly above and below one another, a minimum length L of the goniometer 110 may be measured between the outer ends 136, 138 to an opposite side of the center hub 116. A width W of the goniometer may be measured as a diameter of the center hub 116. Further, a height H of the goniometer 110 may be measured from a bottom of the second arm 130 to a top of the first arm 128, or to a top of the center hub 116, whichever is greater.

In an exemplary embodiment, the center hub 116 comprises a first or upper hub 146 and a second or lower hub 148. The hubs 146, 148 are coaxially aligned with one another, and with axis A. Moreover, the hubs 146, 148 may be configured to rotate about the axis A for 360 degrees, and relative to one another. Further, each of the hubs 146, 148 may have a link arm 143 for coupling between the hubs 146, 148 and the respective arms 128, 130. For example, the first arm 128 may be coupled to the link arm 143 of the first hub 146, and the second arm 130 may be coupled to the link arm 143 of the second hub 148.

In operation, embodiments of the arms 128, 130 may rotate, pivot, flex or extend relative to the center hub 116. This design can account for the complex motion of a joint, slippage of the joint, and the broad range of shapes and sizes of the patient's joint 107. In addition, this design can maintain the position of the center hub relative to the joint center 108. Embodiments of the device can enable freedom of motion in many planes but not in the rotational plane of the joint. This enables the device to fit many different people but still make accurate measurements.

Figure 4:
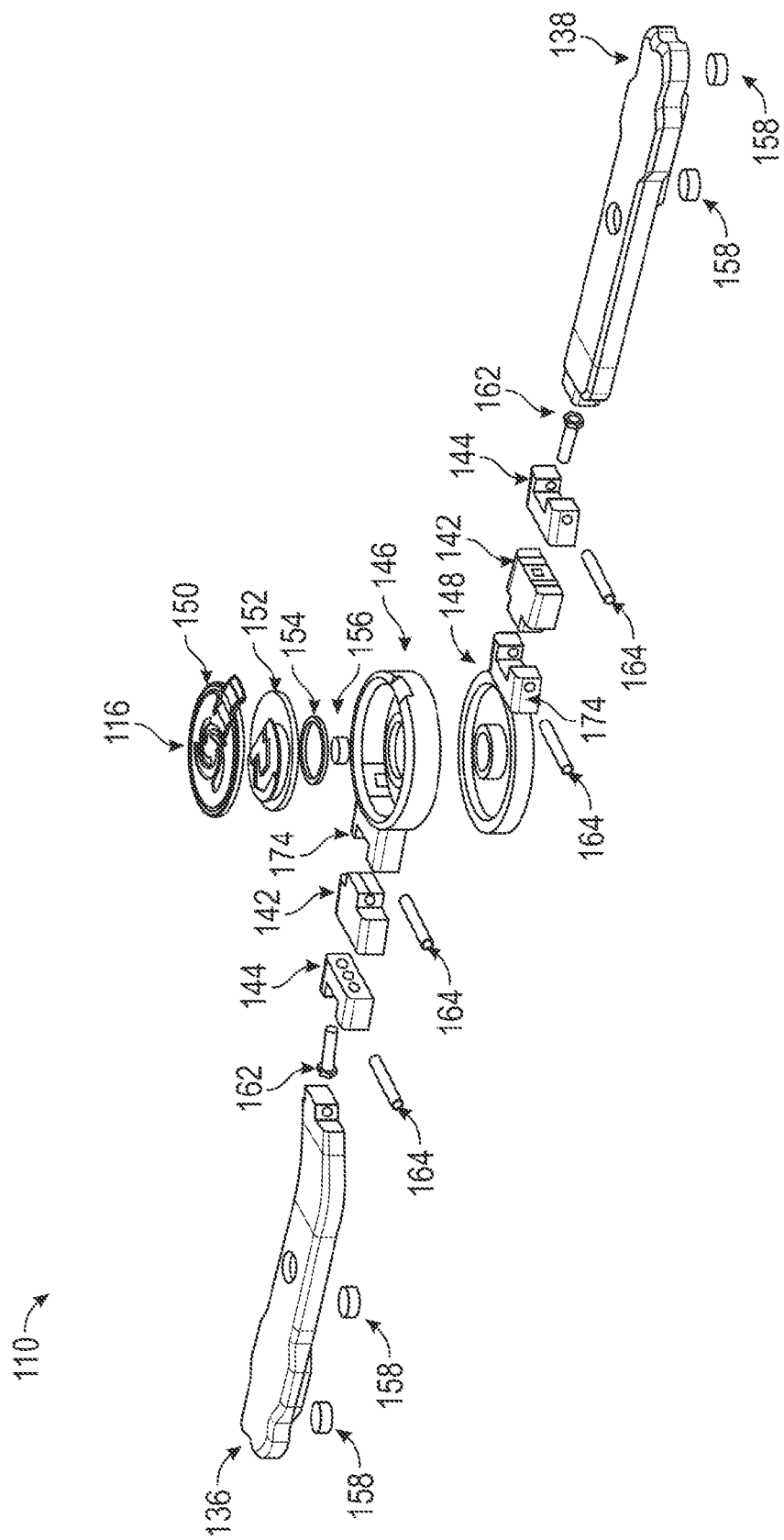
FIG. 4 is an exploded view of a goniometer in accordance with aspects of the present disclosure.
Figure 5A:
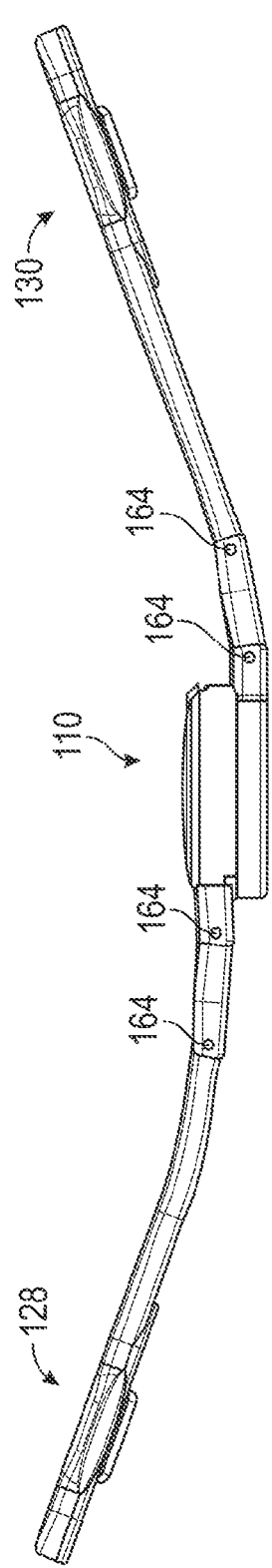
FIGS. 5A-C are side views of the goniometer with its arms rotating in accordance with aspects of the present disclosure.
Figure 5B:
Figure 5C:
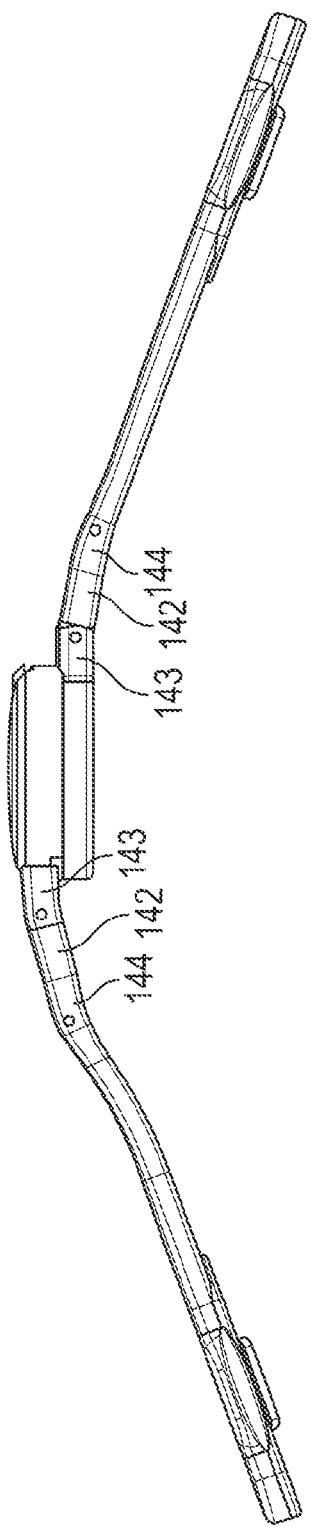

More specifically, and as best illustrated in FIG. 4, the first and second arms 128, 130 may each include an inner link 142 disposed adjacent to the respective inner ends 132, 134, and an outer link 144 disposed between the inner link 142 and the outer ends 168, 170. With reference to FIGS. 5A-C, the inner link 142 may couple to the link arm 143 in order to couple between respective arms 128, 130 and hubs 146, 148. The inner link 142 may be configured to facilitate the pivot, flex, or extension of the respective arm 128, 130 relative to the center hub 116. A pin 164 may be used to couple the inner link 142 and the link arm 143 of each arm 128, 130 to allow for the pivot, flexion, or extension of the respective arms 128, 130. The pin 164 may be disposed perpendicular to the length of the arms 128, 130.

Figure 6:
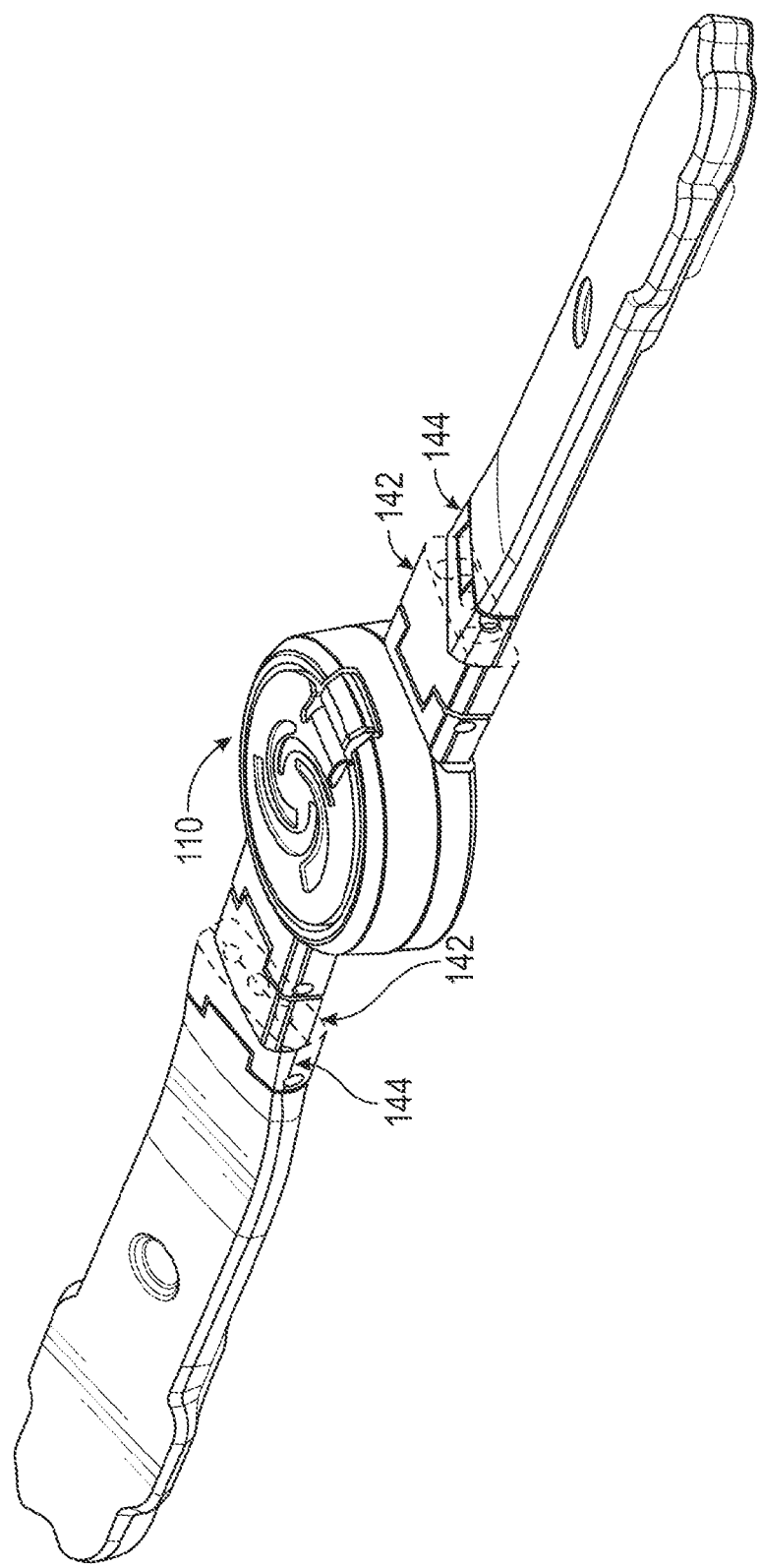
FIG. 6 is a perspective view of the goniometer with its arms twisting in accordance with aspects of the present disclosure.
Figure 7A:
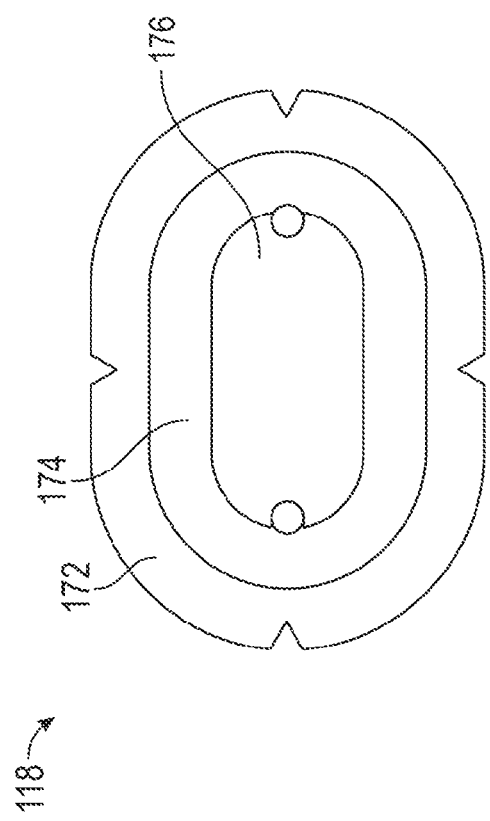
FIGS. 7A-D are top schematic views of the attachment in accordance with aspects of the present disclosure.
Figure 7B:
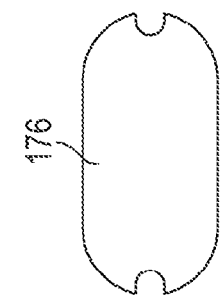
Figure 7C:
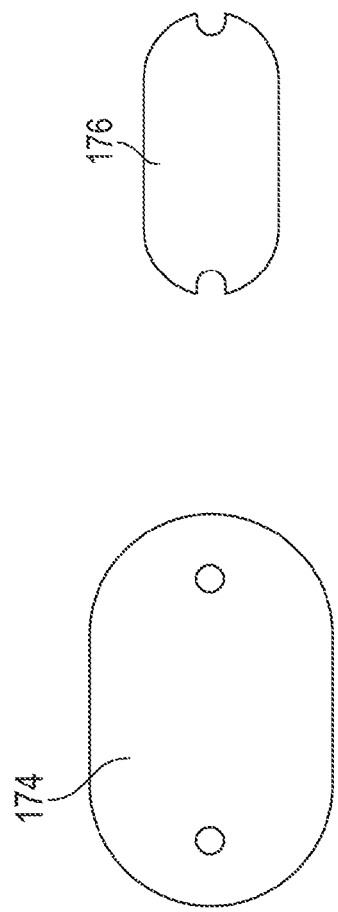
Figure 7D:
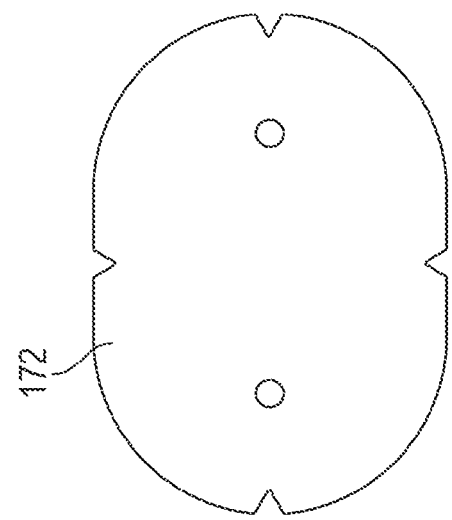
Figure 8A:
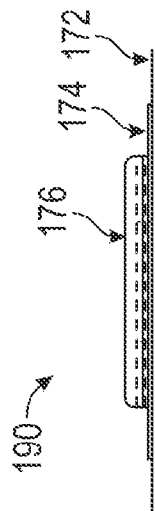
FIGS. 8A-D are views of an attachment in accordance with aspects of the present disclosure.
Figure 8B:
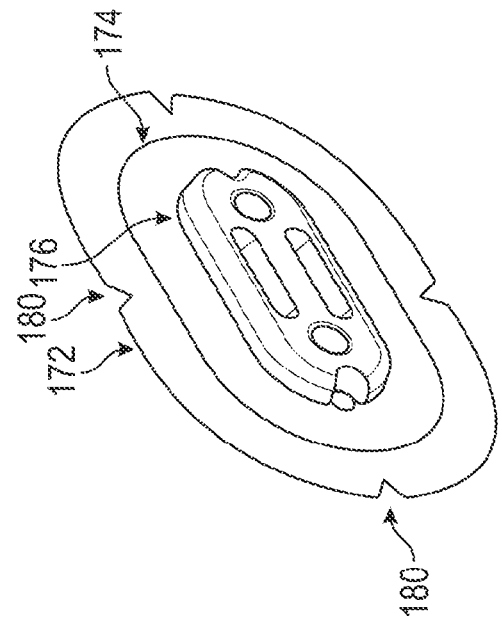
Figure 8C:
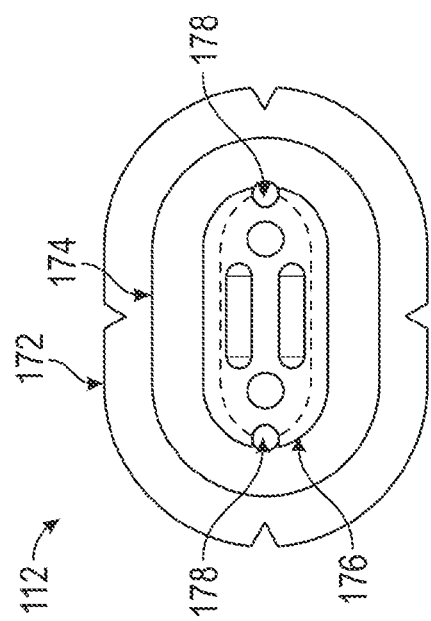
Figure 8D:
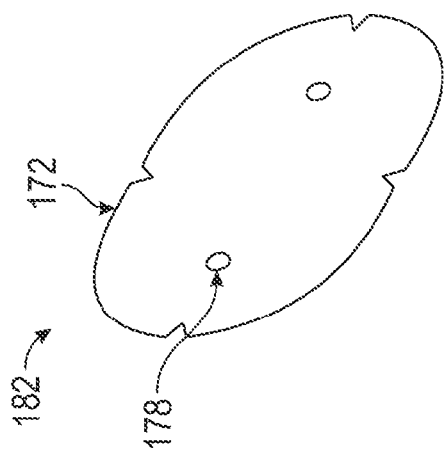
Figure 10B:
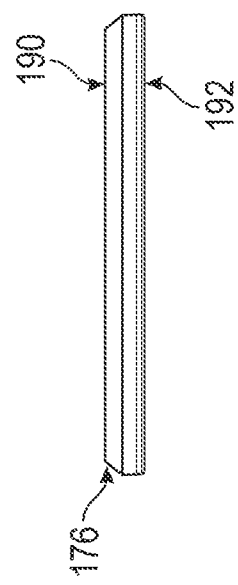
FIGS. 10A-D are views of a pod of the attachment in accordance with aspects of the present disclosure.
Figure 10D:
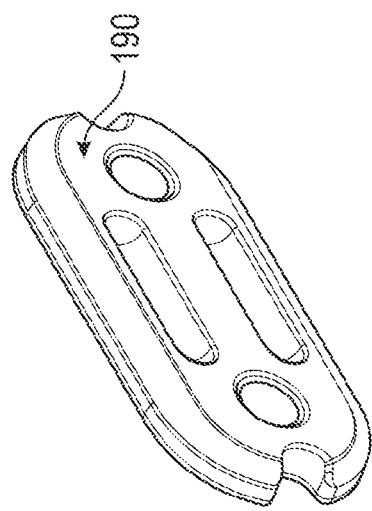
Figure 10A:
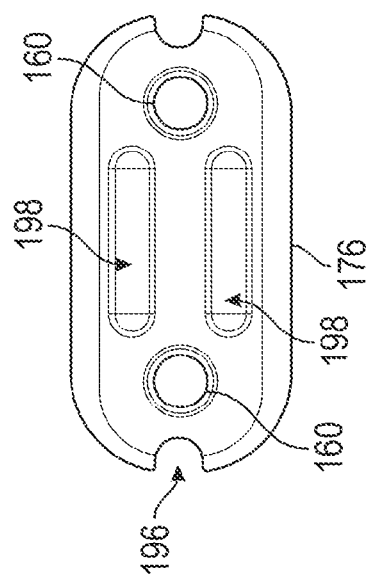
Figure 10C:
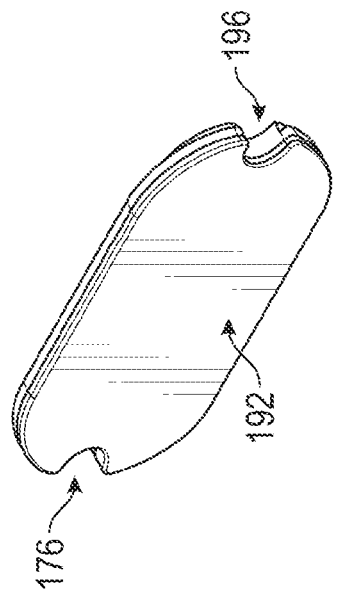

The outer link 144 may couple to the inner link 142 and respective outer ends 136, 138. With reference to FIG. 6, the outer link 144 may be configured to couple to the inner link 142 to facilitate rotation of the respective arms 128, 130 relative to the center hub 116. A screw 162 may be configured to couple the outer link 144 to the inner link 142 to facilitate rotation of the respective arms 128, 130 about the screw 162, all relative to the center hub 116. The screw 162 may align parallel with the length of the respective arm 128, 130. It is to be appreciated that the first and second arms 128, 130 may rotate +/− eighteen degrees, or any other desired amount, in one or more directions. Further yet, and with reference to FIGS. 5A-C, the outer link 144 may be configured to couple to the respective outer ends 136, 138 to facilitate further pivot, flexion, or extension of the respective arms 128, 130 relative to the center hub 116. A pin 164 may be used to couple the outer link 144 and the respective outer ends 136, 138 to allow for further pivot, flexion, or extension, of the respective arms 128, 130 relative to the center hub 116. The pin 164 may be disposed perpendicular to the length of the respective arms 128, 130.

The first and second outer ends 136, 138 may comprise first and second goniometer attachments 168, 170, which may be integral with, or coupled to the respective outer ends 136, 138. It is to be appreciated the goniometer attachments 168, 170 may couple, or be integral with, the arms 128, 130 at any desired location, or in any desired configuration. The first and second goniometer attachments 168, 170 may be configured to removably couple with the attachments 118, 120. Further, each goniometer attachment 168, 170 can comprise one or more bosses 200, and one or more magnets 158 positioned next to the bosses 200 to facilitate the coupling and alignment of the goniometer attachments 168, 170 and the attachments 118, 120. The bosses 200 and magnets 158 further facilitate the alignment of the goniometer 110 relative to the attachments 118, 120. The arms 128, 130 may also include one or more arm alignment holes 140 configured to align with the attachments 118, 120, or an alignment mark on a user 102. The arms 128, 130 may further have one or more wings 202 that extend from a side 126 of the goniometer 110, such as from the first or second goniometer attachments 168, 170. The wings 202 can be formed from or coupled to the first or second goniometer attachments 168, 170. The wings 202 can be a tab or have any other desired shape. The wings 202 may be configured to assist a user in moving the arms 128, 130 of the goniometer perpendicularly relative to the attachments to facilitate uncoupling the goniometer 110 from the attachments 118, 120 without uncoupling the attachments 118, 120 from the user 102.

With reference to FIGS. 7-9, the attachments 118, 120 may comprise first and second layers 172, 174 and a pod 176 coupled together with one another. When coupled to one another, each of the layers 172, 174 and the pod 176 may be concentric with one another. The first attachment 118 may be the same as and interchangeable with the second attachment 120. The first layer 172, the second layer 174, and the pod 176 may be generally oval-shaped or any other desired shape. The first layer 172 may be larger than the second layer 174, and the second layer 174 may be larger than the pod 176. Further, the first layer 172 may be thinner than the second layer 174, and the pod 176 can be thicker than the first and second layers 172, 174.

The first layer 172 may have a top 182 and a bottom 184, and may be formed from a pad, coated paper, plastic, woven fabric, latex, or any other desired material. For example, the top 182 may be formed from a pad and the bottom 184 may comprise an adhesive material 236, such as a medical-grade adhesive or other suitable material. The adhesive material 236 couples to the skin of the user 102 to couple the attachments 118, 120 to the user 102. Further, the top 182 may also have an adhesive layer 194, which may be smaller in area than the first layer 172. Further, the adhesive layer 194 can be less than or equal to the area of the second layer 174. The adhesive layer 194 may be ovular in shape, and define one or more notches or voids in an outer periphery. For example, the first layer 172 can define notches 180 in an outer periphery for assisting in aligning the first attachment 118 relative to a predetermined location, or mark, on the user 102. The notches can be v-shaped or have any other desired shape. Further yet, the first layer 172 may define a pair of voids or alignment holes 178, which may assist in the alignment of the first attachment 118 relative to a predetermined location, or mark, on the user 102.

The second layer 174 may have a top 186 and a bottom 188, and may be formed of a foam material or any other desired material. The second layer 174 may couple to the adhesion layer 194 of the first layer 172. To prevent uncoupling, the foam material of the second layer 174 may dampen forces between the goniometer 110 and the attachments 118, 120. The top 186 of the second layer 174 may also have an adhesive layer 195 on an upper surface 238 of the top 186, which may be smaller in area than the area of the pod 176. The adhesive layer 195 may have an ovular shape with one or more holes, or one or more cutouts that align with the alignment hole 178 of the first layer 172. The adhesive layers 194, 195 can be formed of an adhesive material or any other desired coupling material, such as a hook- or a loop-type material. The first layer 172 can have a length L1 and a width W1. The second layer 174 can have a length L2 and a width W2. The adhesive layer 195 can have a length L3 and a width W3.

As illustrated in FIGS. 10A-D, the pod 176 has a top 190 and a bottom 192. The pod 176 can include one or more notches 196. For example, notches 196 can be located at opposing ends of the pod 176. The notches 196 can be used for alignment of the first coupling apparatus 112, the pod 176, or any other desired feature of the wearable device 100. The pod 176 can include one or more magnets 160. The magnet 160 may be a neodymium magnet or any other desired magnet. The pod 176 can have a recess for housing the magnet 160. The magnet 160 can be circular or any other desired shape. Two magnets 160 can be disposed in the pod 176 at opposing ends of the pod 176. The pod 176 can be sized to be received by and detachably coupled to the upper surface 238 of the second layer 174.

More specifically, the pod 176 has an underside, such as the bottom 192, which may couple to the upper surface 238 of the second layer 174. The bottom 192 can have one or more hooks or loops, to couple to the upper surface 238. Alternatively, the upper surface 238 and the bottom 192 may comprise an adhesive material to facilitate the detachable coupling between the upper surface 238 and the pod 176. The top 190 of the pod 176 may have one or more recesses 198. The recess 198 may be ovular in shape or have any other desired shape. The recesses 198 may also have tapered edges to assist a user 102 in uncoupling from the pod 176 by moving the arms 128, 130 perpendicularly relative to the pod 176. Two recesses 198 may be formed in the pod 176 at opposing ends or sides of the pod 176.

Figure 11A:
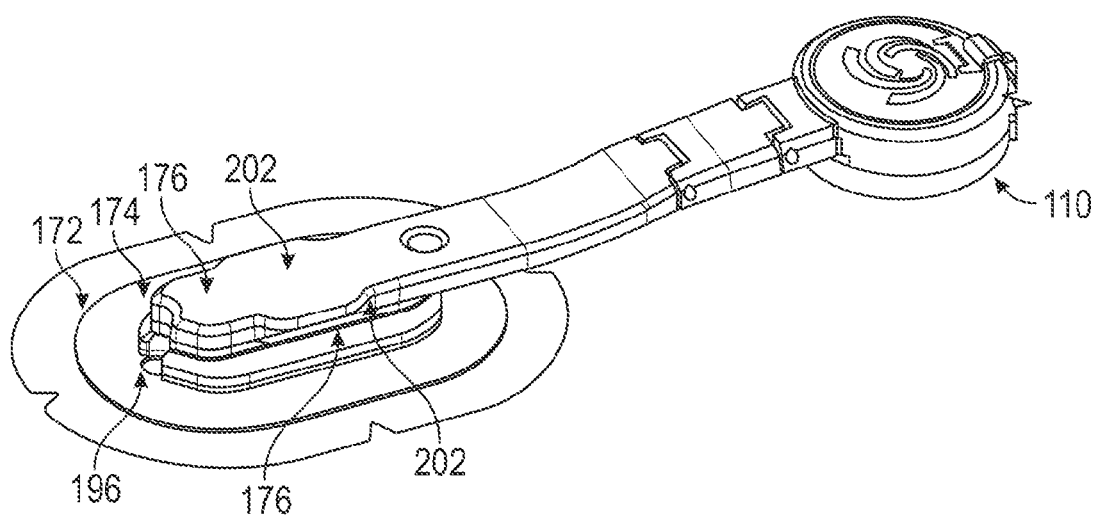
FIGS. 11A and 11B are perspective and cross-sectional views of a coupling apparatus in accordance with aspects of the present disclosure.
Figure 11B:
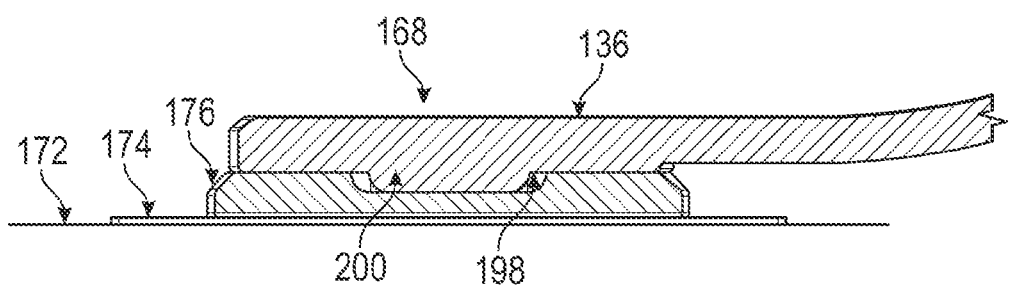
Figure 12A:
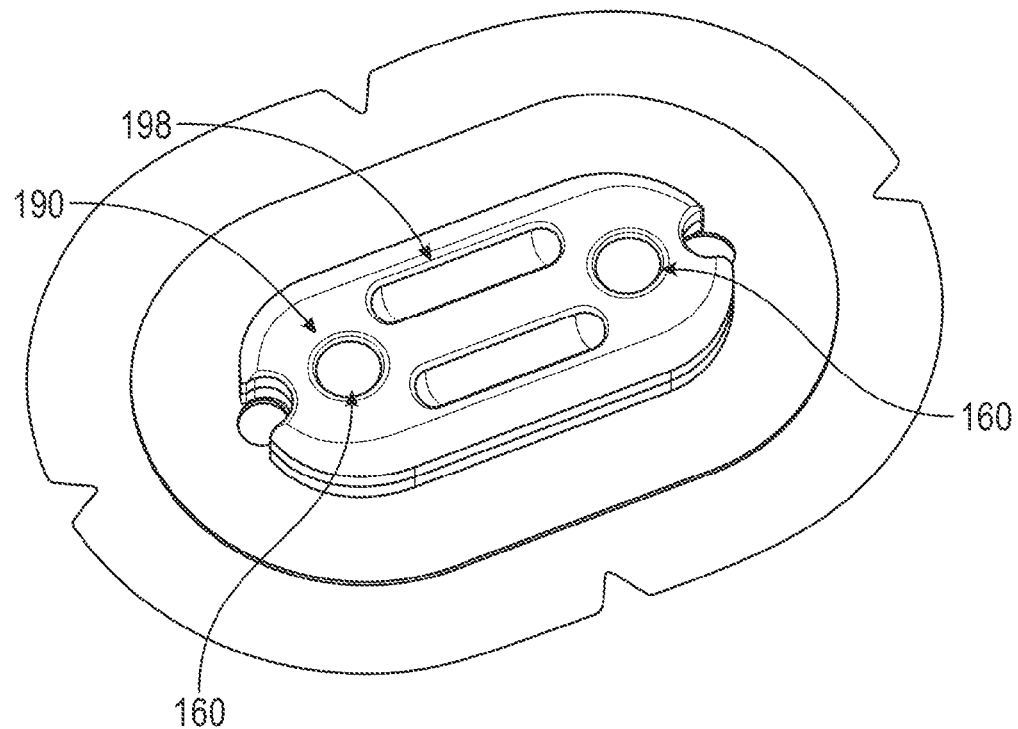
FIGS. 12A and 12B are perspective views of the attachment and a goniometer attachment in accordance with aspects of the present disclosure.
Figure 12B:
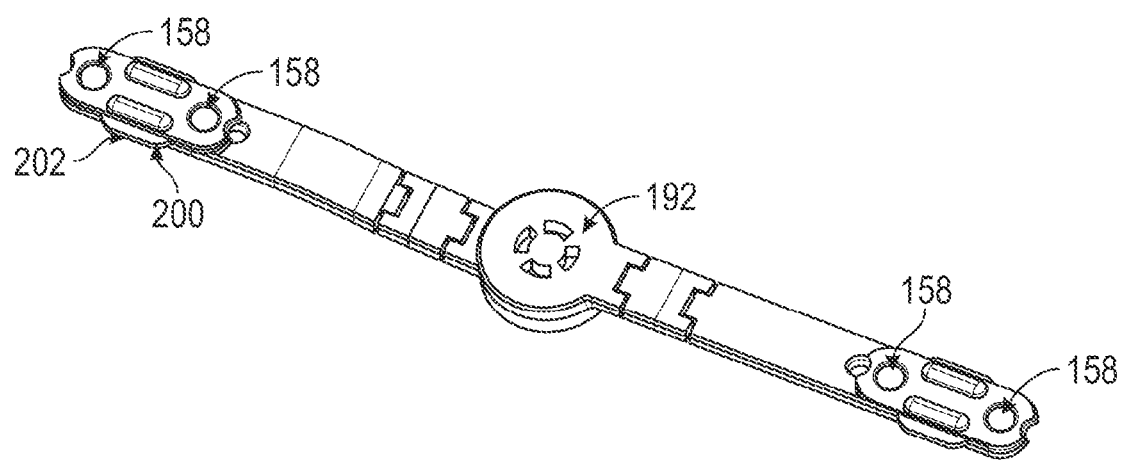

With reference to FIGS. 11-12, the recesses 198 are sized to receive the bosses 200 to align the goniometer 110 relative to the attachments 118, 120. Moreover, the recesses 198 are sized to allow slight movement of the bosses 200 to compensate for slight translational movement of the joints 128, 130 while the goniometer 110 is worn by the user 102. This movement may reduce the stress between, and prevent uncoupling of, the attachments 118, 120 to the skin, clothing, brace, or any other desired location on the user 102.

When the user 102 moves the first or second limb portions 104, 106, the first or second arms 128, 130 move or rotate with the first and second hubs 146, 148. The goniometer 110 can measure the rotation of joint 107 by measuring the angle between the first and second hubs 146, 148. To achieve this, and with reference to FIGS. 4, 13-15, the center hub 116 defines an opening for receiving and containing a printed circuit board (PCB) 152, a sensor 216, a retaining ring 154 or other means of fixation of the hubs 146, 148, a magnet 156, or any other components of the goniometer 110 which cooperate with one another to measure relative angular movement between the arms 128, 130. More specifically, the first and second hubs 146, 148 may define the opening of the center hub 116.

For enclosing the opening, a cover 150 may be attached to the center hub 116, and more specifically to the first hub 146. The cover 150 can be detachably coupled to the first hub 146 or any other desired location. The cover 150 can also be configured to inhibit movement of the PCB 152 and other components located within the center hub 116. For example, when the cover is closed, a bottom portion of the cover 150 may apply direct or indirect pressure to the PCB 152. The cover 150 may have a snap mechanism 226, such as a finger snap or any other desired mechanism, configured to attach and detach the cover to the center hub 116. The assembly may or may not be waterproof. For example, cover 150 may or may not enable the assembly to be waterproof.

The magnet 156 may couple to the second hub 148, and the sensor 216 also disposed in the center hub 116 is configured to detect rotation of the magnet 156. The sensor 216 can be configured to measure the rotation of the magnet 156 to a sensitivity up to one-hundredth of a degree, or to any other desired sensitivity.

Figure 13:
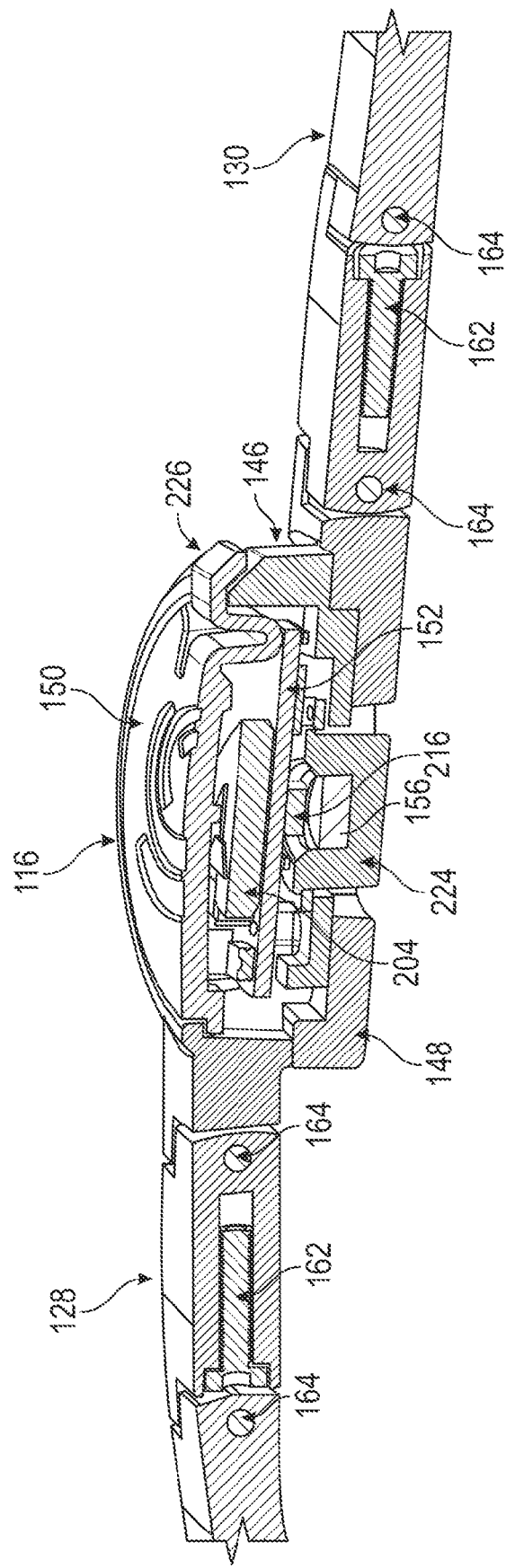
FIG. 13 is a cross sectional view of the goniometer in accordance with aspects of the present disclosure.
Figure 14A:
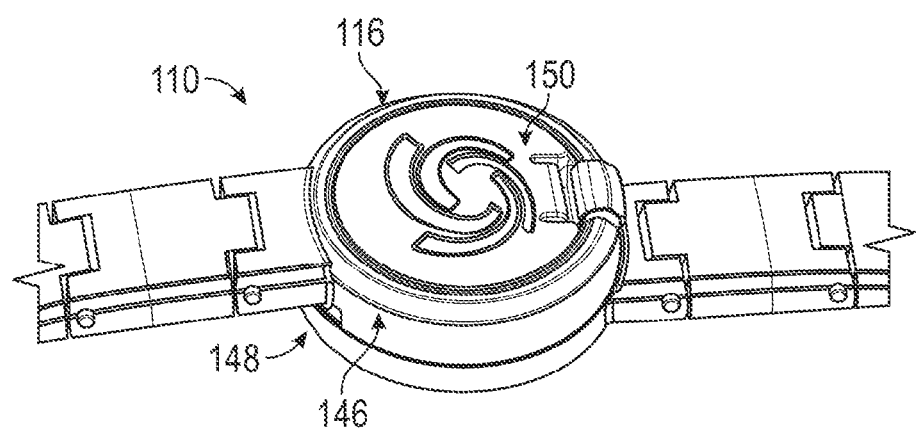

As illustrated in FIGS. 13-14C, the center hub 116 includes the first hub 146 positioned rotatably above the second hub 148. An outward notch 208 may be coupled to the first hub 146, or any other desired location. The outward notch 208 may be formed with the first hub 146 or attached to the first hub 146. The PCB 152 may be removably disposed in the center hub 116. The PCB 152 may have an inward notch 210. The outward notch 208 may be configured to couple with the inward notch 210 to align the sensor 216 and the magnet 156. The alignment can restrict movement of the PCB 152 within the center hub 116.

Figure 14B:
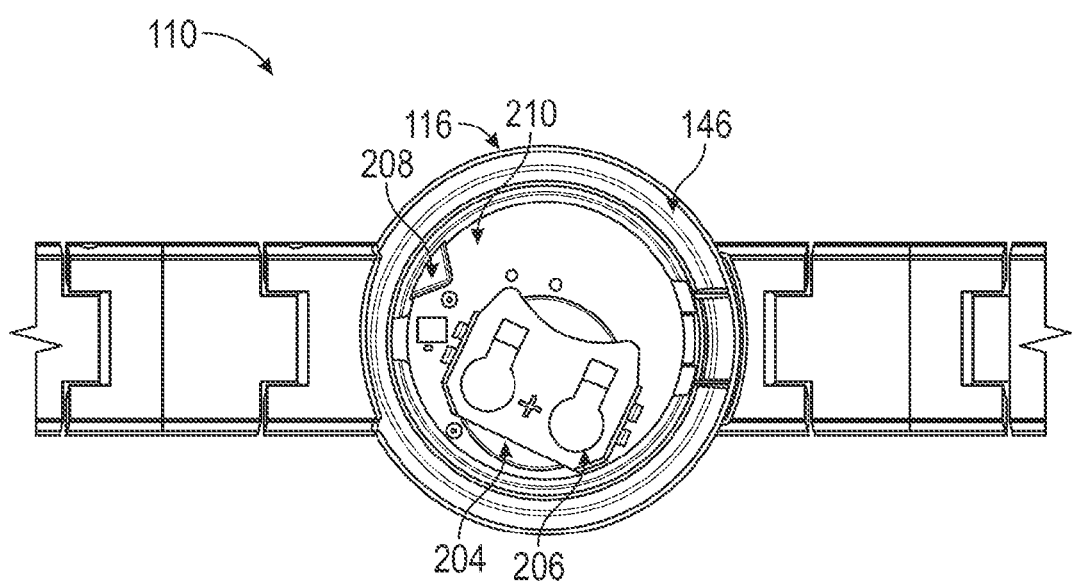

When the cover 150 is removed, the PCB 152 may be accessed. FIG. 14B illustrates a battery housing 206 coupled to the PCB 152. The battery housing 206 may be attached to a top side 212 of the PCB 152. The battery housing 206 may be formed of conductive metal or any other desired material. When the cover 150 is attached to the first hub 146, the cover 150 may apply pressure to the battery housing 206, which may secure PCB 152 within the center hub 116. A battery 204 may be detachably coupled to the battery housing 206. The battery 204 may be a lithium ion battery or any other desired battery or power source. The battery housing 206 may have tabs or any other desired contact points for conduction with the battery 204. The battery 204 may be removed from the battery housing 206 to turn the goniometer 110 off or for replacement of the battery 204. For example, when the cover 150 is opened or removed from the first hub 146, the PCB 152 may be removed from the center hub 116 and the battery 204 may be replaced. To maintain calibration of the goniometer 110 after a battery replacement, the inward notch 210 of the PCB 152 is configured for receiving the outward notch 208 of the first hub 146.

In FIG. 14C, the cover 150 and the PCB 152 are removed from the center hub 116. As shown, the second hub 148 may include a magnet housing 224. The magnet housing 224 may be located in the center of the second hub 148 or any other desired location. The magnet housing 224 may be coupled to the PCB 152 using a weld, an adhesive, a tack, or any other desired attachment. The magnet housing 224 may be configured to receive the magnet 156. The magnet 156 may be configured to have north and south polarity within the center hub 116 or any other desired polarity. The magnet housing 224 may include a lip at a top of the magnet housing 224 or have any other desired configuration. The retaining ring 154 may be configured to couple the magnet 156 to the second hub 148. The retaining ring 154 may be coupled to the second hub 148 around the magnet housing 224. For example, the retaining ring 154 may be positioned between the lip or top of the magnet housing 224 and the second hub 148. The retaining ring 154 may secure the magnet within the magnet housing 224. The retaining ring 154 may be coupled to and move with the second hub 148, and the magnet 156 can be the second hub 148 to rotate with the second arm 130.

Figure 15A:
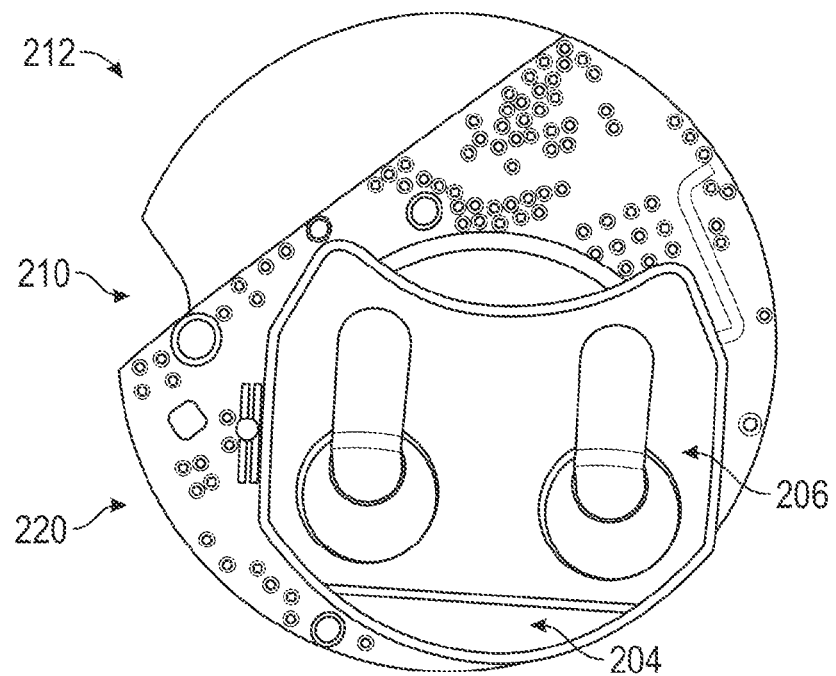
FIGS. 15A and 15B are top and bottom views of a printed circuit board (PCB) in accordance with aspects of the present disclosure.
Figure 15B:
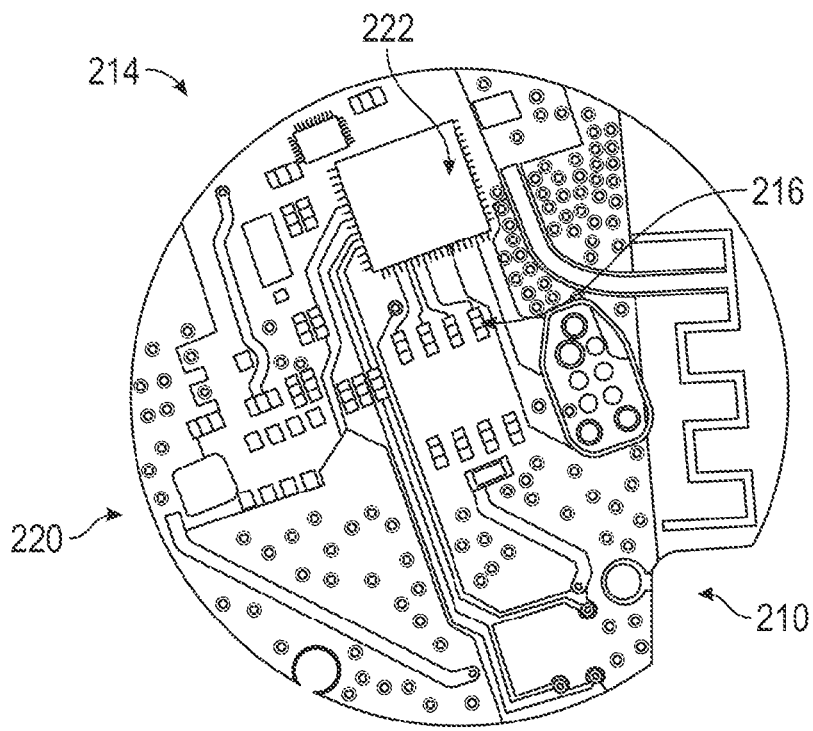

FIG. 15A illustrates the top side 212 of the PCB 152. As described above, the battery housing 206 may be attached to the top side 212. FIG. 15B illustrates a bottom side 214 of the PCB 152 in accordance with aspects of the present disclosure. The PCB 152 includes components coupled to the bottom side 214. The components may comprise a circuit 220 including resistors, LEDs, transistors, capacitors, inductors, transducers, diodes, switches, the sensor 216, a transmitter 222, or any other desired component. The components may be attached to the PCB 152 using a surface mount method, a through-hole method, or any other desired method. Again, the steps of the methods can be performed in various different orders. The PCB 152 may include additional and/or fewer components and is not limited to those illustrated in FIGS. 15A and B.

The circuit 220 may be configured to generate an electrical signal based on the rotation of the magnet 156. The circuit 220 may be configured to transmit the electrical signal in real time. The circuit 220 may transmit the electrical signal. For example, a transmitter 222 may be coupled to the PCB 152 and configured to transmit an electrical signal based on the rotation of the magnet 156 to an external device. The transmitter 222 may include wired or wireless transmission, such as Bluetooth™, WiFi, NFC or any other means or method of desired transmission. The external device may be a mobile phone, a computer, a tablet, or any other desired device. The external device may have a user interface. The user interface may be configured to receive the electrical signal and display data obtained from the electrical signal. The data may include the angle of the joint 107, or any other desired information.

The user interface may include an app that receives the data, manipulates the data, records the data, and displays aspects of the data. For example, the app may display the angle of the joint 107 of a user 102, a history of the angle of the joint 107, duration of the angle, or any other desired information, such as a measurement of the angle in real time.

The sensor 216 may be a Hall Effect sensor, or any other desired sensor (e.g., a magnetic position sensor AS5601 using internal MEMS Hall Effect sensors). The sensor 216 may be coupled to the PCB 152 or any other desired device. The sensor 216 may be coupled to the bottom side 214 of the PCB 152 at a location directly above the magnet 156 when the PCB 152 is disposed within the center hub 116. The PCB 152 and the sensor 216 may rotate with the first hub 146 and the first arm 128. The magnet 156 may rotate with the second hub 148 and the second arm 130. The design of the wearable device 100, including the configuration of the sensor 216 and the magnet 156, may improve the accuracy of the measurements of the angle of the joint 107.

Figure 16B:
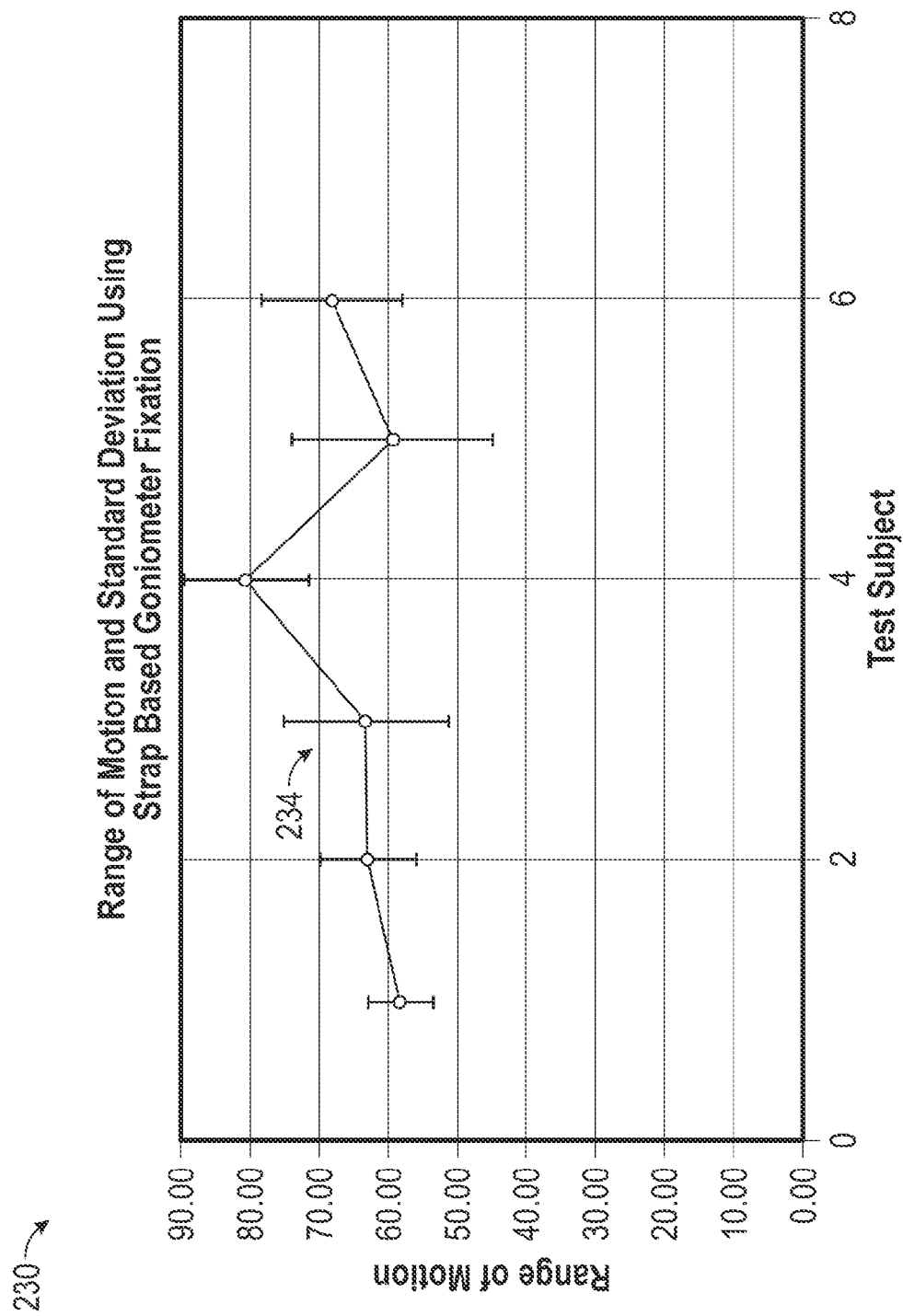
Figure 17A:
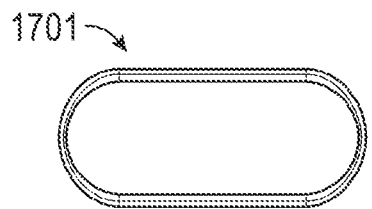
FIGS. 17A-17E are various views of an embodiment of a pedometer that may be coupled to the goniometer in accordance with aspects of the present disclosure.
Figure 17B:
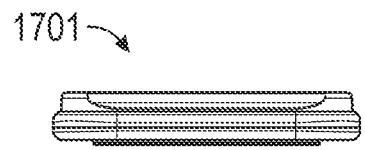
Figure 17C:
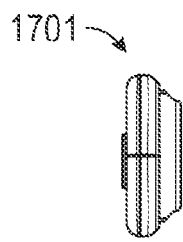
Figure 17D:
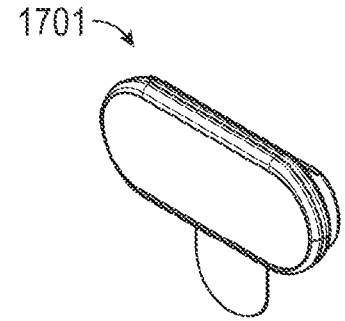
Figure 17E:
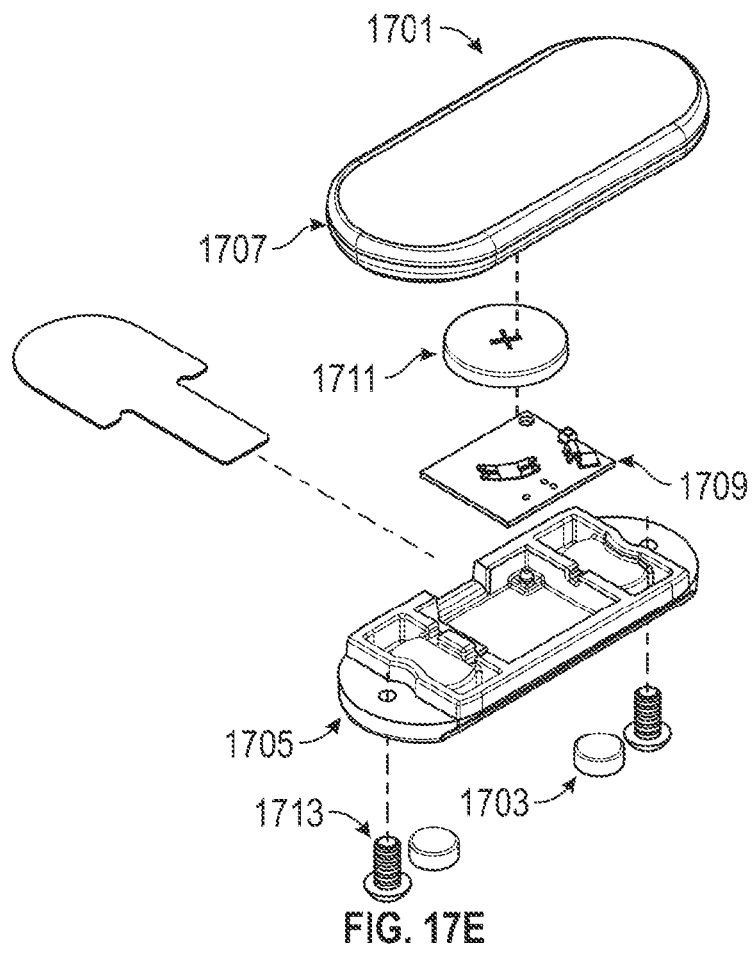

FIG. 16A is an exemplary graph 228 with line 232 depicting, while the wearable device 100 is attached to the user 102, the accuracy of measurements of angles of the joint 107 by the wearable device 100. FIG. 16B is an exemplary graph 230 with line 234 depicting the accuracy of measurements of angles of the joint 107 by a different measurement device attached to a user using Velcro™ straps. The standard deviation of the measurements made by the different measurement device shown by line 234 is greater than the standard deviation of the measurements made by the wearable device 100 shown by line 232. Users, such as clinicians or patients, are able to more accurately initially place and realign the first and second attachments 118 and 120 of the wearable device 100 as compared to using the Velcro™ straps. The configuration of the first and second arms 128, 130 of the wearable device 100 to fit different users may increase accuracy of the measurements. The configuration of the components, including the PCB 152, the sensor 216, and the magnet 156 within the center hub 116 of the wearable device 100 may further increase accuracy of the measurements. The wearable device 100 may be configured to measure the angle of the joint 107 up to an accuracy of measurement up to a one hundredth degree. The different measurement device may have an accuracy up to five degrees. In other words, the measurements taken by the different measurement device may have an accuracy of about +/− five degrees, such as about +/1 1 degree, or even +/− about 0.01 degree from the actual angle of the joint 107.

As described elsewhere herein, the pods can be adhered to the skin. For example, a peel and place pod having a consumable alignment arm and centering pod can help align the epicondyle center point of the knee of the user to the upper and lower points for more accurate placement.

FIGS. 17A-17E depict an embodiment of an ambulation monitor or pedometer 1701. Versions of the pedometer 1701 can count the number of steps that a user takes, such as a daily count of steps post-operatively. Such a device can be carried by the user or attached to the user or to a peripheral of the user, such as the goniometer 110. The pedometer 1701 is operational to track steps of the user even if the user requires a walker or other assistance device.

In some versions, the pedometer 1701 can include the ability to attach to the magnets of the goniometer 110 to ensure accurate tracking of all steps of the user. The pedometer 1701 can include metallic elements that are magnetically attracted to the magnets of the goniometer 110. Alternatively, additional magnets 1703 may be mounted to the pedometer 1701. Embodiments of the pedometer 1701 can further include a body 1705, a removable cap 1707, and a circuit board 1709 having one or more sensors (e.g., a motion sensor such as an accelerometer, mechanical sensor) or other electromechanical sensor, a battery 1711 and fasteners 1713.

Figure 18:
FIG. 18 is an isometric view of an embodiment of a knee brace shown prior to assembly and attachment to a user in accordance with aspects of the present disclosure.
Figure 19:
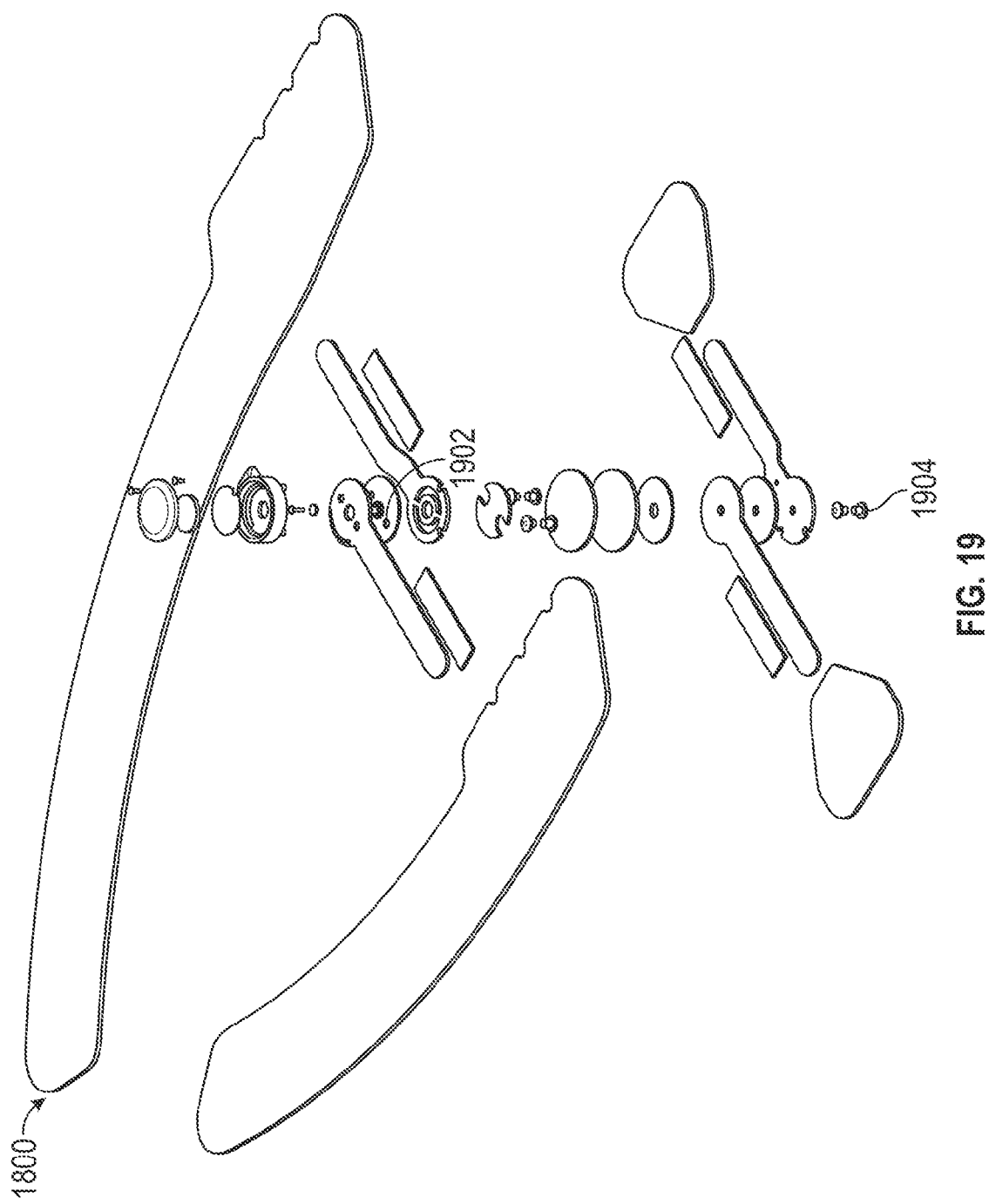
FIG. 19 is an exploded view of an embodiment of the knee brace of FIG. 18 in accordance with aspects of the present disclosure.
Figure 20:
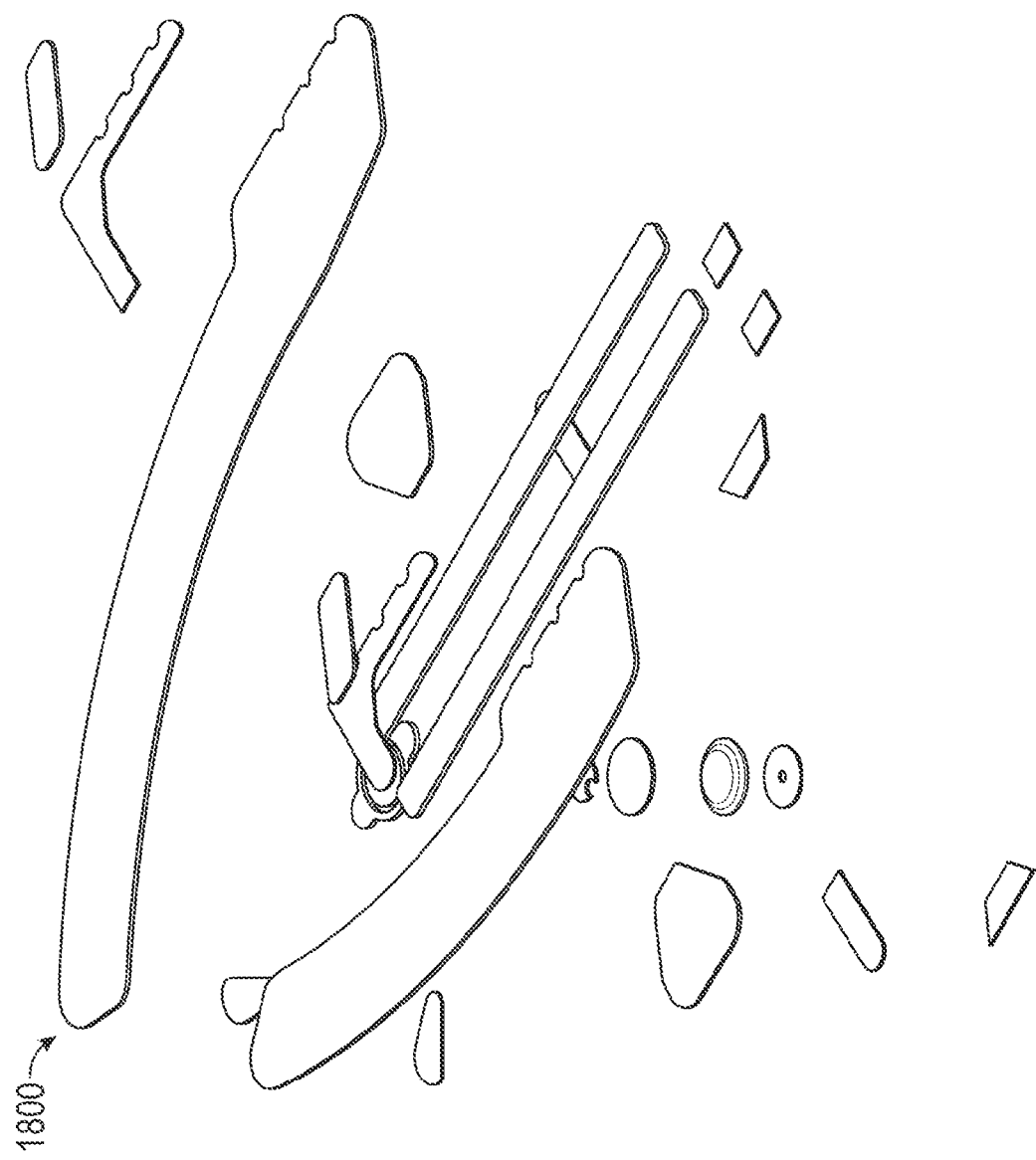
FIG. 20 is an exploded view of additional components of an embodiment of the knee brace of FIG. 18 in accordance with aspects of the present disclosure.

FIGS. 18-23 show embodiments of a knee brace 1800 in accordance with aspects of the disclosure. FIG. 19 shows an exploded view of FIG. 18 showing some sub-components of the knee brace 1800. FIG. 20 shows another exploded view of FIG. 18 showing some sub-components of the knee brace 1800. FIG. 21 shows a picture of components of the knee brace 1800 of FIG. 18. FIGS. 22A-22D show pictures of the knee brace 1800 a leg of a user. FIGS. 23A-23B show pictures of components of the knee brace 1800 being applied to the leg of the user. Where "##(##)" notation is used, the numerals outside the parentheses indicate the figure number, while the numerals inside the parentheses indicate the reference number as shown in the indicated figure. For example, 19(1) refers to the component labeled 1 in FIG. 19).

The knee brace 1800 may include a calf strap 19(14), 20(8), 2304 for connecting the knee brace 1800 to a patient's calf. The calf strap 19(14), 20(8), 2304 may be connected to a lateral calf post 19(1) by a hook pad 19(20). The calf strap 19(14), 20(8), 2304 may include a first set of features to line up the brace with the patient's calf. For example, the calf strap 19(14), 20(8), 2304 may include a set of apertures or holes in the calf strap 19(14), 20(8), 2304, and/or indentations or cutouts on an edge of the calf strap 19(14), 20(8), 2304 (e.g., three holes or three indentations) that allow the practitioner or the patient to place a set of marks on the patient's calf. After the marks have been placed on the patient's calf, the knee brace 1800 may be removed and reapplied to the patient's leg by lining up the marks on the patient's calf with the holes or indentations on the calf strap 19(14), 20(8), 2304.

Figure 23B:
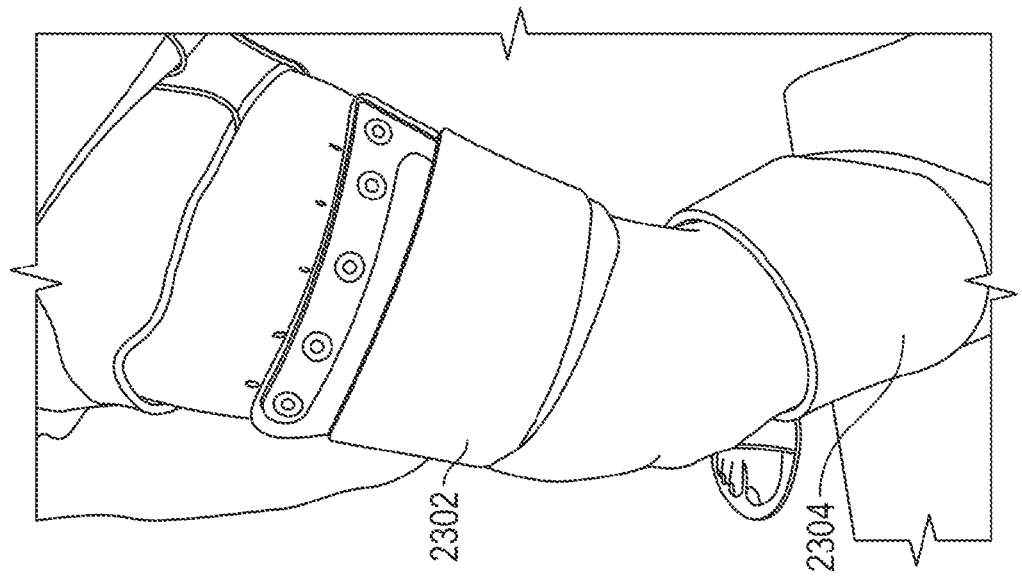
FIGS. 23A-23B are picture views of application of an embodiment of the knee brace being applied to a leg of the user in accordance with aspects of the present disclosure.
Figure 23A:
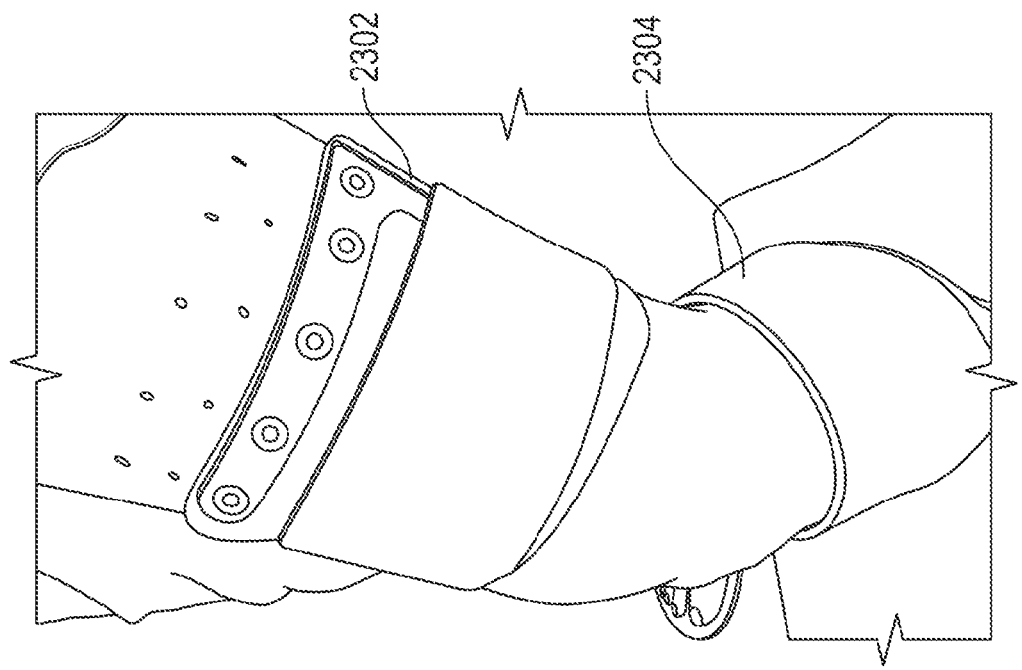

The knee brace 1800 may further include a thigh strap 19(6), 20(9), 2302 for connecting the knee brace 1800 to the patient's thigh. The thigh strap 19(6), 20(9), 2302 may be connected to a lateral thigh post 19(13) by a hook pad 19(20). As shown in FIGS. 23A-23B, the thigh strap 19(6), 20(9), 2302 may include a system to line up the brace with the patient's thigh. For example, the thigh strap 19(6), 20(9), 2302 may include a set of apertures or holes in the thigh strap 19(6), 20(9), 2302 or indentations or cutouts on an edge of the thigh strap 19(6), 20(9), 2302 (e.g., five holes or five indentations) that allow the practitioner or the patient to place a set of marks on the patient's thigh. After the marks have been placed on the patient's thigh, the knee brace 1800 may be removed and reapplied to the patient's leg by lining up the marks on the patient's thigh with the holes or indentations on the thigh strap 19(6), 20(9), 2302. As shown in FIGS. 23A and 23B, two sets of marks may be applied indicating a maximum and minimum height for the thigh strap 19(6), 20(9), 2302 to be applied to the thigh. Specifically, FIG. 23A shows the thigh strap 19(6), 20(9), 2302 applied too low on the thigh, as indicated by the visibility of the markings, while FIG. 23B shows the thigh strap 19(6), 20(9), 2302 applied at a proper height on the thigh, as indicated by the set of holes in the thigh strap 19(6), 20(9), 2302 showing blank skin in the space between the two sets of markings.

A lateral hinge includes the lateral calf post 19(1) and the lateral thigh post 19(13). The lateral calf post 19(1) and the lateral thigh post 19(13) are rotatable relative to one another and are separated by a lateral brace washer 1902. The lateral hinge includes a lateral hub 19(21), 2102 that contains components of a device, such as an electronic device (e.g., a goniometer, a pedometer, etc.). The components may include a sensor, a circuit board 19(3), 2104, and a battery 19(2). The lateral hub 19(21) 2102 may be formed similarly to and function similarly to the first hub 146, as described previously. The lateral hub 19(21) 2102 may be connected to and fixed relative to the lateral calf post 19(1) The circuit board 19(3), 2104 may function as PCB 152 functions and may include the components of PCB 152 (e.g., may be configured to generate an electrical signal based the motion of a magnet, may be configured transmit an electrical signal, may include transistors, etc.). The sensor may function as sensor 216 and may include the components of sensor 216 (e.g., the sensor may be a Hall Effect sensor, the sensor may be coupled to the circuit board 19(3), 2104, etc.). The lateral calf post 19(1) may be connected to the lateral hub 19(21) 2102. By using a pair of fasteners 19(5), 19(11), a lateral cap 19(8) can be fastened to and provide protection for the lateral hub 19(21) 2102 and its contents. In embodiments where the knee brace 1800 includes a pedometer, the pedometer may function as pedometer 1701 functions and may include the components of pedometer 1701. The lateral thigh post 19(13) may be connected to a lateral pad receiver 19(9) by a pair of fasteners 19(22). An alternative embodiment of the lateral pad receiver 19(9) is shown in FIG. 21 as element 2110. The fasteners can enable the two parts of the center hub assembly to rotate on a center axis. The fasteners can be used in slots to allow for rotation. A magnet 19(4), 2106 may be connected to the lateral thigh post 19(13) for interacting with the sensor and allowing the goniometer to detect the change in angular position of the knee brace 1800, and thus the patient's knee. The lateral brace washer 1902 may include a central feature for receiving the magnet 19(4), 2106. The magnet 19(4), 2106 in the goniometer can help determine angularity of the device with a Hall Effect sensor. A knee pad 19(7) for contacting a lateral side of a patient's knee may be connected to the lateral pad receiver 19(9). A stop pin 19(10), 2108 passes through a slot in the lateral calf post 19(1) and into one of a series of holes in the lateral thigh post 19(13) in order to adjustably limit the range of motion of the patient's knee.

The knee brace 1800 may further include a medial hinge, which may include a medial calf post 19(17) and a medial thigh post 19(16), each of which may be connected by a hoop pad 19(20) to a medial cuff pad 19(15). The medial cuff pads 19(15) may be respectively connected to the thigh strap 19(6), 20(9), 2302 and the calf strap 19(14) 20(8), 2304. The connection can be made with hook and loops fasteners. It can be made manually on the medial side of the affected knee. The connection adds stability to the brace and helps in positioning stability as well. The medial calf post 19(17) and the medial thigh post 19(16) may be separated by a medial brace washer 19(18) (e.g., a second washer). The medial hinge may further include a medial pad receiver 19(19) that may be connected to the medial calf post 19(17). One or more fasteners 1904 may extend through central holes within and hold together the medial pad receiver 19(19), the medial calf post 19(17), medial brace washer 19(18), and the medial thigh post 19(16). A knee pad 19(7) for contacting a medial side of the patient's knee may be connected to the medial pad receiver 19(19).

The knee brace 1800 may further include integrated pockets on or about the lateral hinge, the medial hinge, lateral calf post 19(1), the lateral thigh post 19(13), the medial calf post 19(17), the medial thigh post 19(16), the calf strap 19(14) 20(8), 2304, and/or the thigh strap 19(6), 20(9), 2302 for containing ice packs for reducing swelling in the patient's knee. In some embodiments, the integrated pockets are sealable and watertight, allowing for the direct insertion of ice into the integrated pockets and reducing external condensation in the vicinity of the ice packs. The knee brace 1800 may further include connectors on or about the lateral hinge, the medial hinge, lateral calf post 19(1), the lateral thigh post 19(13), the medial calf post 19(17), the medial thigh post 19(16), the calf strap 19(14) 20(8), 2304, and/or the thigh strap 19(6), 20(9), 2302 for connecting an ice pack to the knee brace 1800 for reducing swelling in the patient's knee.

FIG. 20 is an exploded view of the soft goods for the brace. In the center, an alignment device also locates the knee epicondyle and wraps around the knee horizontally, both above and below the incision in the user. This can be used to align the brace.

It is understood that the components of the knee brace may be rearranged and include more components or fewer components without departing from the disclosure. Examples of such rearrangements include moving the goniometer from the lateral hinge to the medial hinge. In some versions, the medial hinge can just be for stability. There can be left leg and right leg versions of the brace. The goniometer can reside on the lateral side of the knee. Other examples can include placing the hub containing the goniometer in contact with a thigh post instead of with a calf post, and forming braces for other joints (e.g., an elbow brace for an elbow joint including one or more forearm posts and one or more upper arm posts, a generic brace for a generic joint including one or more inferior joint posts and one or more superior joint posts) according to the teachings of the disclosure.

Figure 24:
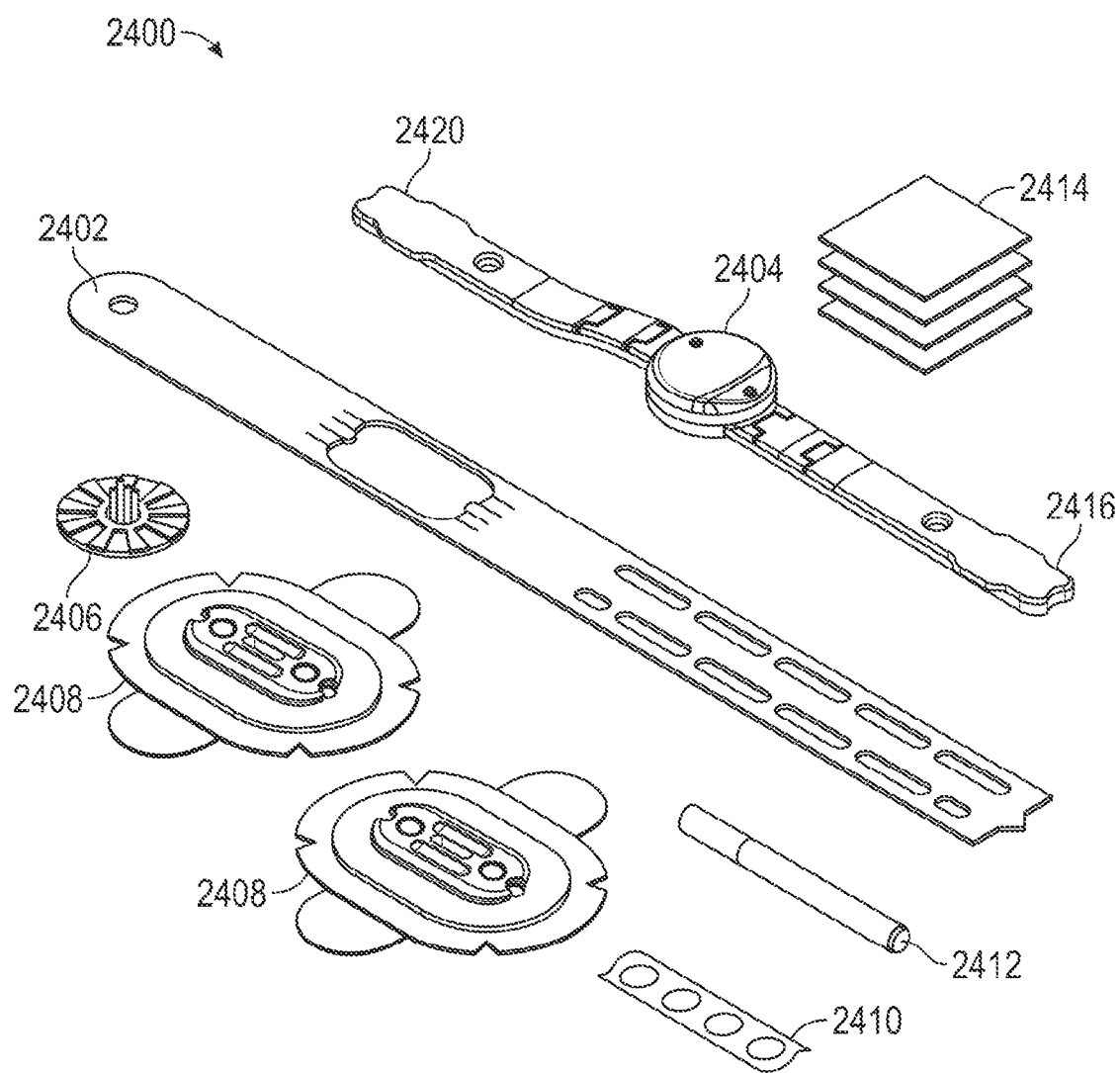
FIG. 24 illustrates a perspective view of an embodiment of a system for attaching two pods to a leg in accordance with aspects of the present disclosure.

FIG. 24 illustrates an embodiment of a system 2400 for attaching a goniometer to a leg of a user. Some versions of the system 2400 may include a pod targeting template 2402, a goniometer 2404, a knee pivot anchor 2406, a pair of anchor pods 2408, a set of four dot stickers 2410, a surgical marker 2412, and four alcohol preparation pads 2414. Examples of the goniometer 2404 may include a pair of goniometer arms 2416, 2420, each of which can include one or more goniometer arm magnets or ferromagnetic materials.

Figure 25:
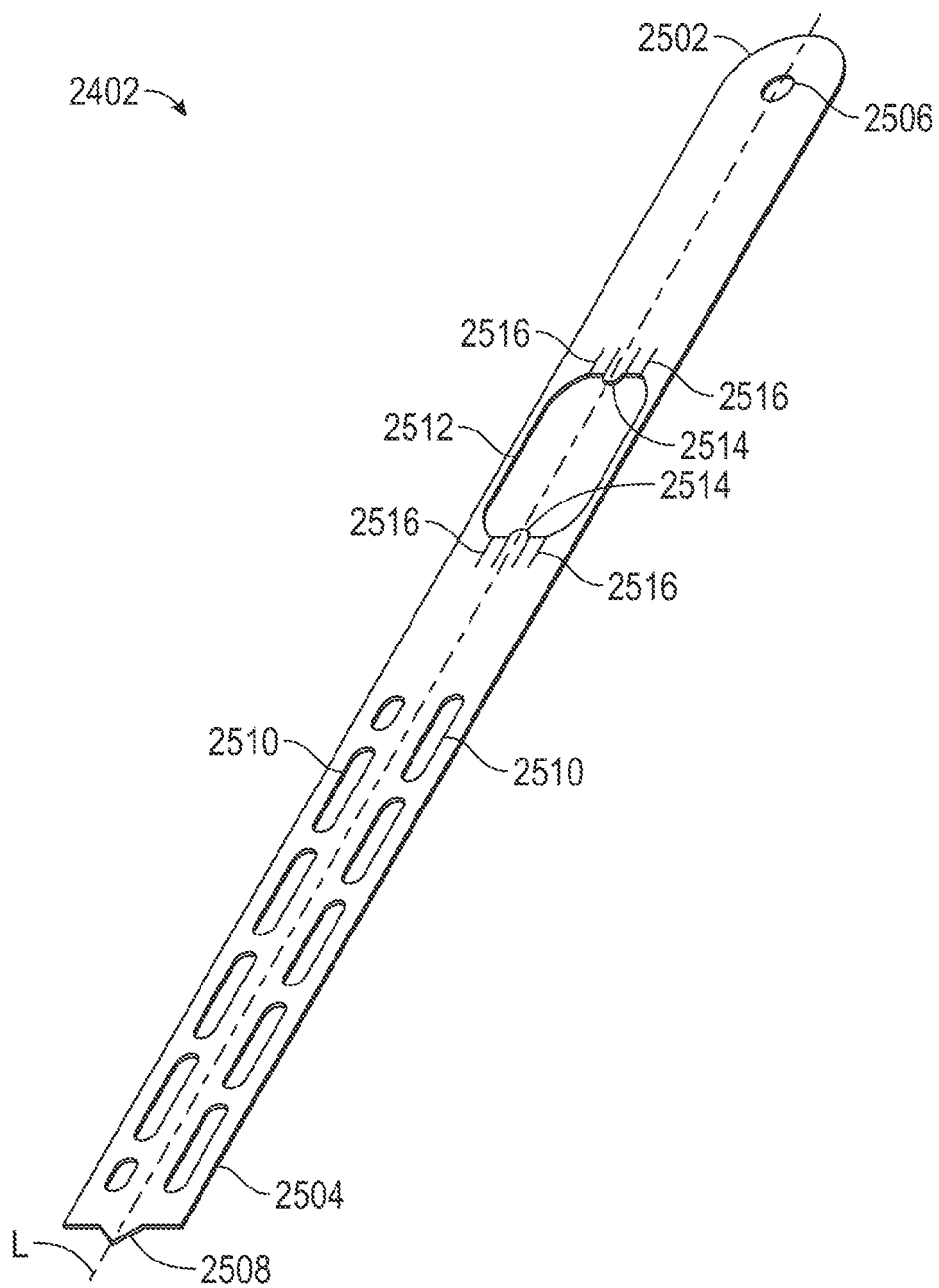
FIG. 25 illustrates perspective views of an example of a pod targeting template in accordance with aspects of the present disclosure.

FIGS. 25A and 25B illustrate perspective views of an example of the pod targeting template 2402 in greater detail. The pod targeting template 2402 may have a proximate end 2502 and a distal end 2504. A knee pivot hole 2506 can be included for receiving and connecting to the knee pivot anchor 2406, and may be located near the proximate end 2502 of the pod targeting template 2402. A triangular tip 2508 may extend from the distal end 2504 of the pod targeting template 2402. A longitudinal axis L may pass through the centerline of the pod targeting template 2402. The pod targeting template 2402 may further include one or more rows of visibility holes 2510 along the pod targeting template 2402 to allow for seeing physiological target markings on shorter people. FIG. 25 shows the pod targeting template 2402 having two rows of visibility holes 2510, but one row (or more than two rows) of visibility holes is also contemplated, as seen in FIGS. 29H and 29I. An aperture or pod reception hole 2512 for receiving and connecting to the anchor pods 2408 may be defined within the pod targeting template 2402. Pod reception tabs 2514 may be placed along the outside of the pod reception hole 2512 and facilitate holding the anchor pods 2408 in place.

Figure 26A:
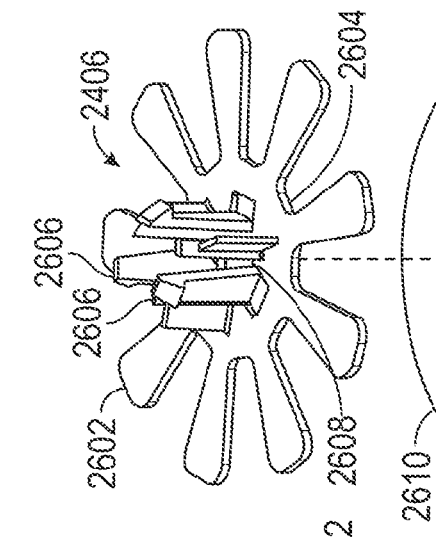
FIGS. 26A-26E illustrate perspective views of an example of a knee pivot anchor in accordance with aspects of the present disclosure.
Figure 26B:
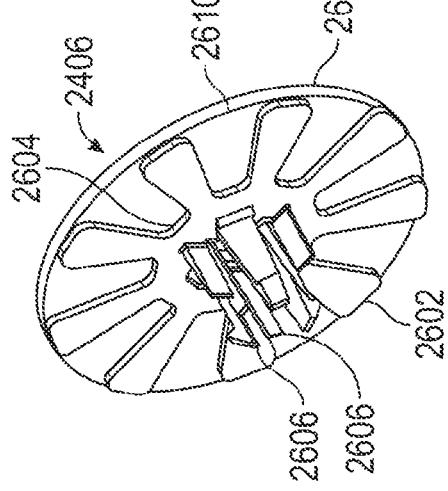
Figure 26C:
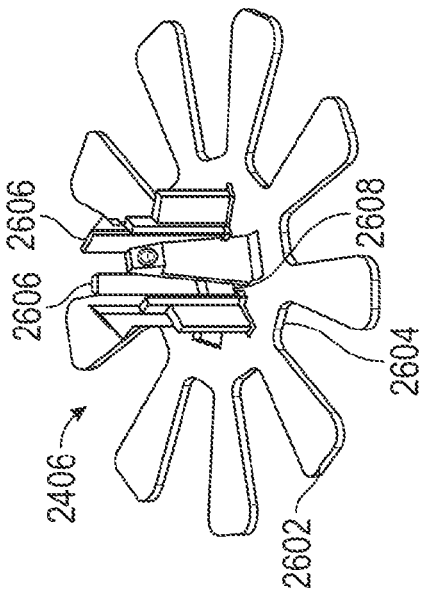
Figure 26E:
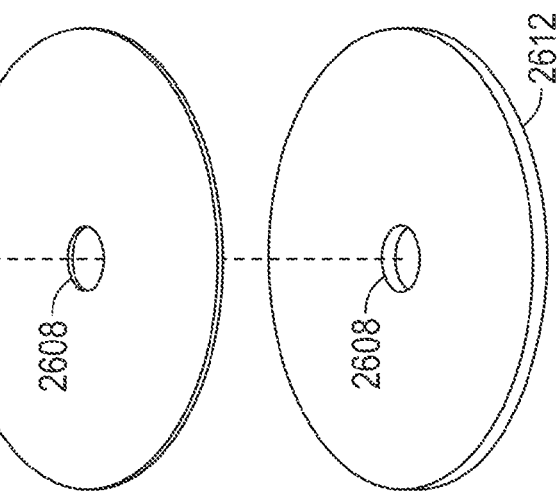
Figure 26D:
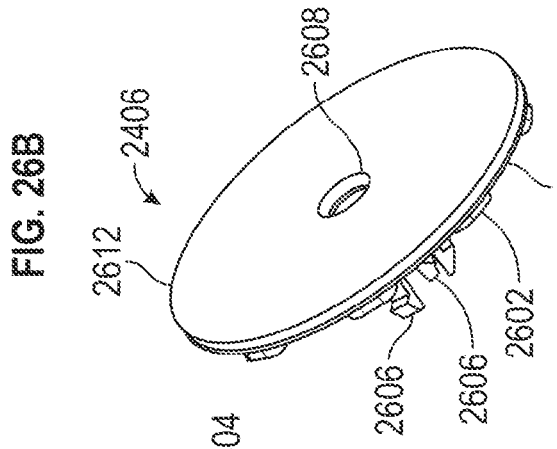

FIGS. 26A-26E illustrate perspective views of an example of the knee pivot anchor 2406, with FIG. 26E being an exploded perspective view, in greater detail. The knee pivot anchor 2406 may include a flat disk structure 2602 having indentations 2604 extending inwards. The indentations 2604 may serve to reduce material requirements and increase the flexibility of the flat disk structure 2602, as the knee pivot anchor 2406 is intended to be fixed to a surface that is generally not flat (i.e., the side of a person's knee). A set of anchor tabs 2606 may extend upward from near the center of the flat disk structure 2602. The anchor tabs 2606 may serve to connect the knee pivot anchor 2406 to the pod targeting template 2402. An anchor hole 2608 may be defined in the center of the knee pivot anchor 2406 for allowing a user to line up the knee pivot anchor 2406 with a mark placed on the skin of a person. A knee pivot adhesive pad 2610 may be fixed to flat disk structure 2602 for allowing the knee pivot anchor 2406 to be fixed to the knee of a person. Knee pivot backing 2612 may cover the adhesive on the knee pivot adhesive pad 2610 until peeled off, preventing the adhesive from being inadvertently attached to a wrong surface. The anchor hole 2608 may also extend through both the knee pivot adhesive pad 2610 and the knee pivot backing 2612.

Figure 27A:
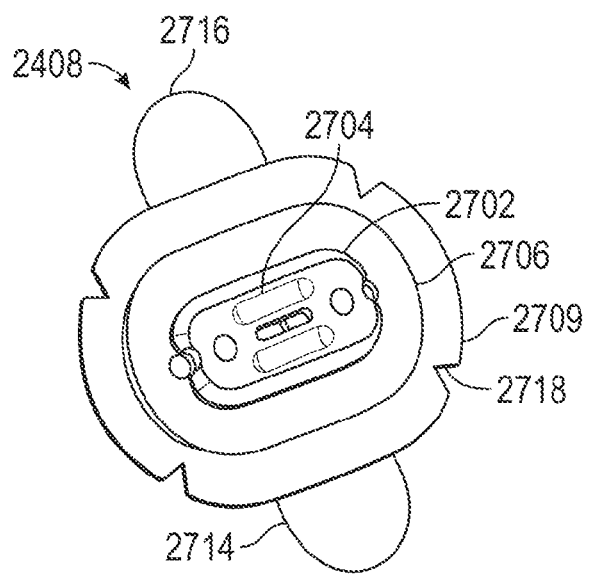
FIGS. 27A-27C illustrate perspective views of an example of an anchor pod in accordance with aspects of the present disclosure.
Figure 27B:
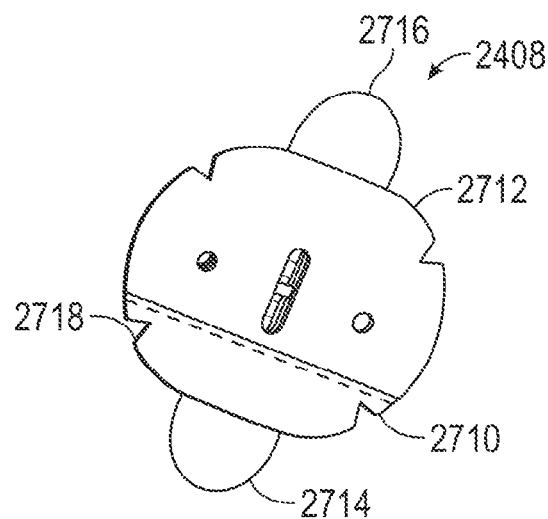
Figure 27C:
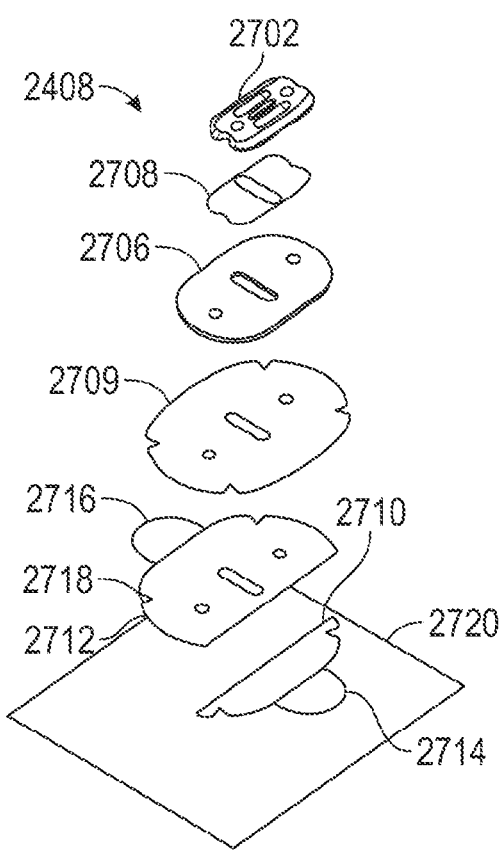

FIGS. 27A-27C illustrate an example of one of the anchor pods 2408, with FIG. 27C being an exploded perspective view, in greater detail. The anchor pods 2408 may each include a reception module 2702 for engaging and connecting to the goniometer arms 2416, 2420. The reception module 2702 may contain a magnet 2704 or ferromagnetic material for attracting or being attracted to the magnet or ferromagnetic material of the goniometer arms 2416, 2420. The reception module 2702 may also contain a central structure 2706. The central structure 2706 may be connected to the reception module 2702 with a first pod adhesive layer 2708. A second pod adhesive layer 2709 may be connected to the other side of the central structure 2706. A first pod backing portion or half 2710 and a second pod backing portion or half 2712 each may cover a portion of the second pod adhesive layer 2709, with the first pod backing half 2710 overlapping and covering a small portion of the second pod backing half 2712. While the term "half" is used, each of the pod backing halves 2710, 2712 may be of differing sizes and cover more or less than half of the second pod adhesive layer 2709. A first backing tab 2714 (labeled with a "1") may be connected to the first pod backing half 2710 to facilitate the removal of the first pod backing half 2710 from the second pod adhesive layer 2709. A second backing tab 2716 (labeled with a "2") may be connected to the second pod backing half 2712 to facilitate the removal of the second pod backing half 2712 from the second pod adhesive layer 2709. The removal process would be to use the first backing tab 2714 to remove the first pod backing half 2710, and then to use the second backing tab 2716 to remove the second pod backing half 2712. Four notches 2718 are defined in the perimeter of the second pod adhesive layer 2709 and the portions of the first pod backing half 2710 and the second pod backing half 2712. These notches 2718 may be used as guides for aligning the anchor pod 2408 during re-application by using the surgical marker 2412 to mark the skin around the notches 2718 and placing the anchor pod 2408 such that the marks line up with the notches 2718 during reapplication. Each anchor pod 2408 may be stored in an assembly pouch 2720 prior to use.

It is understood that the components of the system 2400 may be rearranged and include more components or fewer components without departing from the disclosure. Examples of such rearrangements include having more or fewer intermediate layers or integral parts in the anchor pod 2408 and using different connection means between the anchor pods 2408 and the pod targeting template 2402.

Figure 28A:
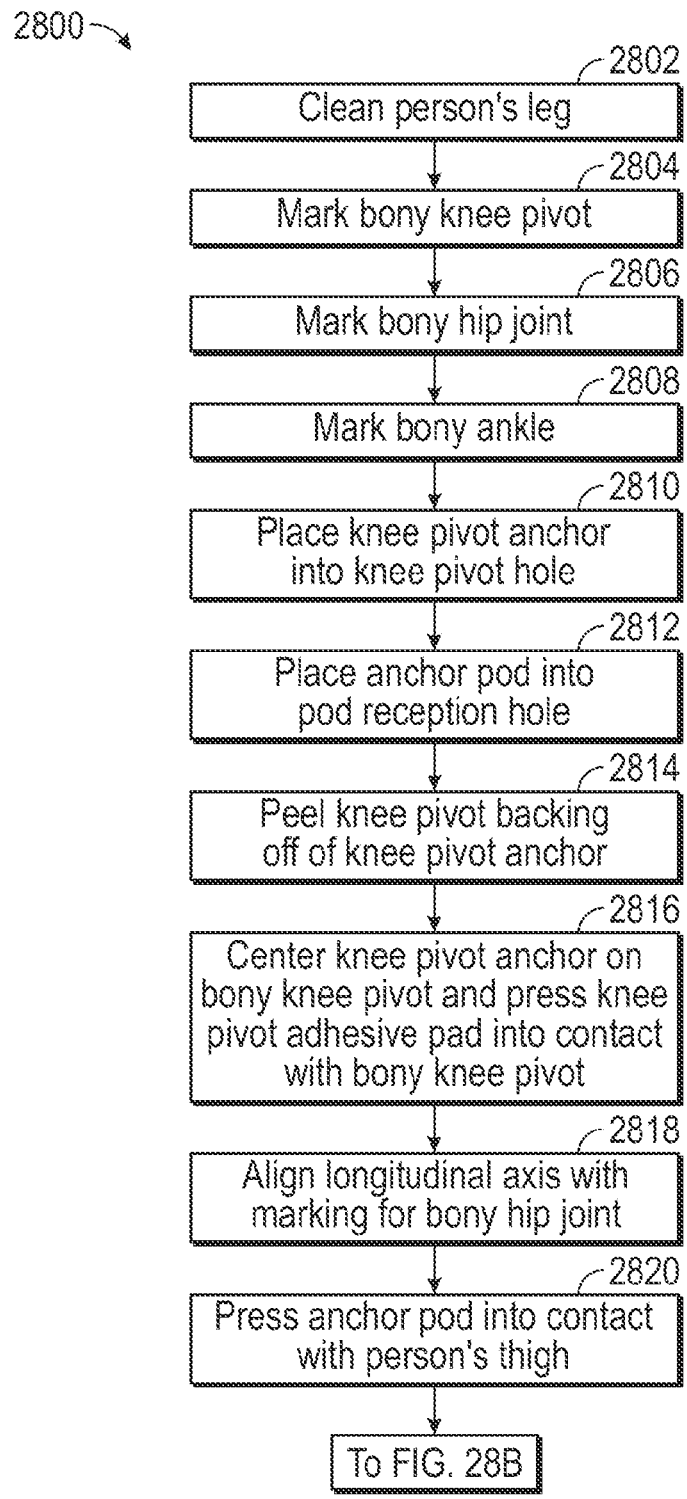
FIGS. 28A-28C, provide a flowchart view for an embodiment of a method of attaching a goniometer to a leg of a person in accordance with aspects of the present disclosure.
Figure 28B:
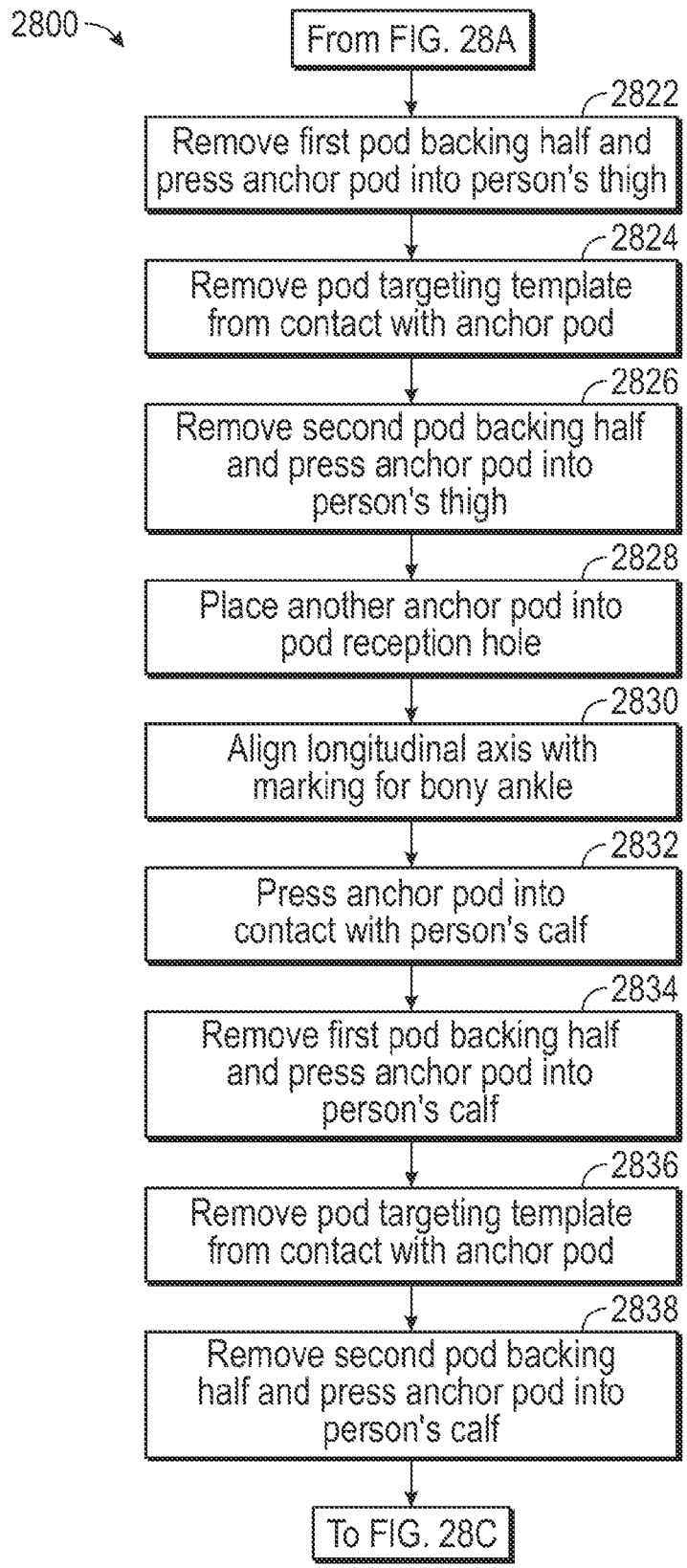
Figure 28C:
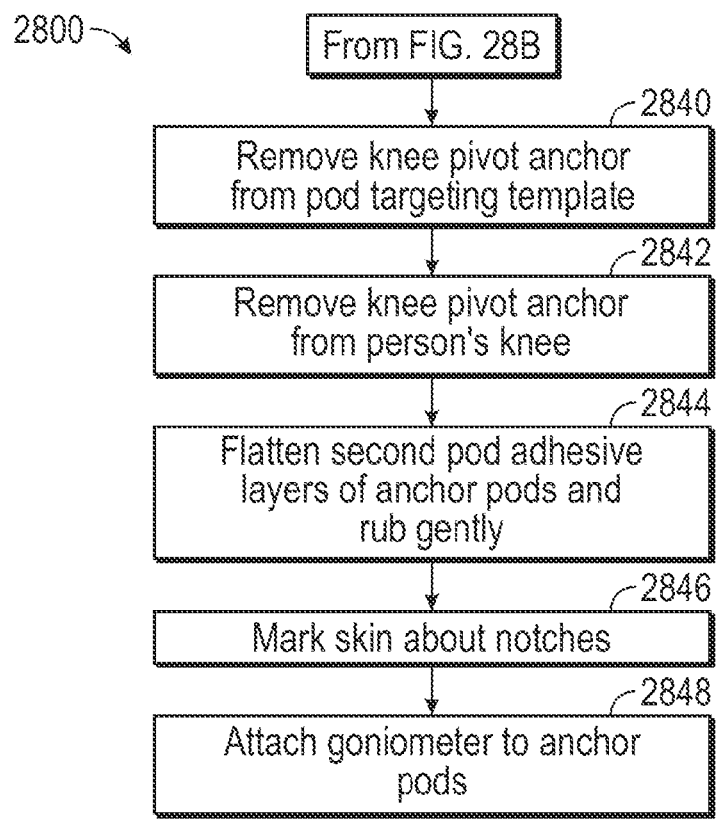

As shown in FIGS. 28A-28C, an embodiment of a method 2800 for attaching a goniometer to a leg of a person is disclosed. FIGS. 29A-29L illustrate another embodiment of steps that can be performed, as referenced below.

At step 2802 in FIG. 28A and as depicted in FIG. 29A, the method 2800 may include cleaning the person's leg. This may include cleaning between 10 inches (25.4 cm) or more above and 10 inches (25.4 cm) or more below the lateral side of the person's knee. The cleaning may be accomplished by using alcohol preparation pads, such as the alcohol preparation pads 2414.

At step 2804, as illustrated in FIG. 29B, the method 2800 may include marking the bony knee pivot 2902 (i.e., the lateral epicondyle) on the lateral side of the knee. The bony knee pivot 2902 may be marked as the point on the skin closest to the widest part of the knee bone structure. The bony knee pivot 2902 may be marked with a marker or other writing device, such as the surgical marker 2412.

At step 2806, as illustrated in FIG. 29C, the method 2800 may include marking the bony hip joint 2904 (i.e., the greater trochanter). The bony hip joint 2904 may be marked at the widest point in the person's hip above the hip joint. The bony hip joint 2904 may be marked with a sticker, such as one of the dot stickers 2410, placed on the person's clothing. The person should avoid moving around if possible after the application, as the sticker is on the person's clothing, which may move relative to the person's bony hip joint 2904.

At step 2808, as illustrated in FIG. 29D the method 2800 may include marking the bony ankle 2906 (i.e., the lateral malleolus). The bony ankle 2906 may be marked on the widest bony point on the outside of the person's ankle. The bony ankle 2906 may be marked with a sticker, such as one of the dot stickers 2410, or a marker or other writing device, such as the surgical marker 2412. If the marking is a sticker on the person's sock, the person should avoid moving around if possible application, as the sock may move relative to the person's bony ankle 2906.

At step 2810, as illustrated in FIG. 29E, the method 2800 may include placing the knee pivot anchor 2406 into the knee pivot hole 2506 of the pod targeting template 2402. This may be accomplished via a snapping action of the anchor tabs 2606 within the knee pivot hole 2506.

At step 2812, as also illustrated in FIG. 29E, the method 2800 may include placing the anchor pod 2408 into the into the pod reception hole 2512 of the pod targeting template 2402. The anchor pod 2408 may be held in place using two pod reception tabs 2514 and four cantilever snap features 2516 located next to the two pod reception tabs 2514.

At step 2814, the method 2800 may include peeling the knee pivot backing 2612 off of the knee pivot anchor 2406 to expose the knee pivot adhesive pad 2610.

Figure 29F:
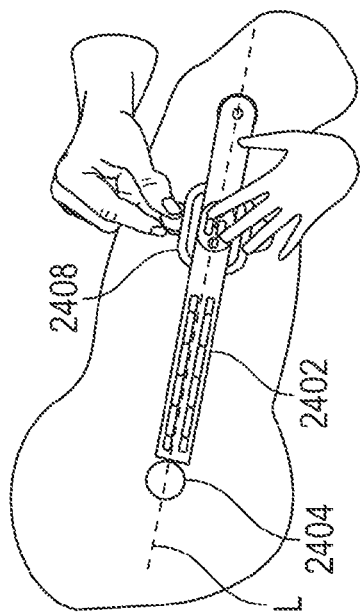

At step 2816, as illustrated in FIG. 29F, the method 2800 may include centering the knee pivot anchor 2406 on the bony knee pivot 2902 as marked at step 2804 and pressing the knee pivot adhesive pad 2610 into contact with the bony knee pivot 2902. Centering may be accomplished by viewing the marking for the bony knee pivot 2902 through the knee pivot hole 2506 and the anchor hole 2608.

Figure 29G:
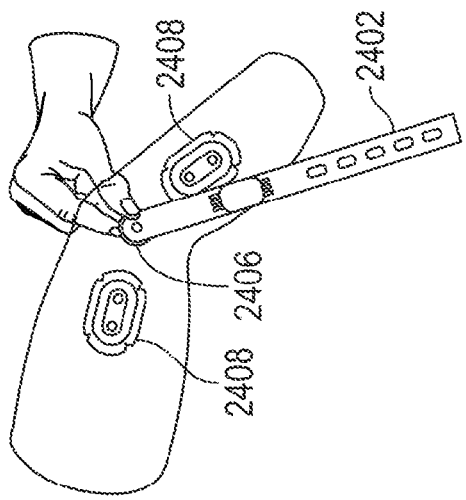
Figure 29H:
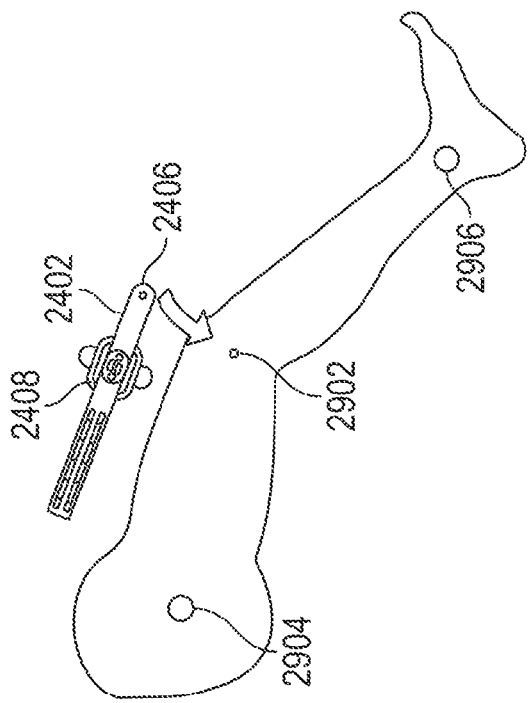
Figure 29I:
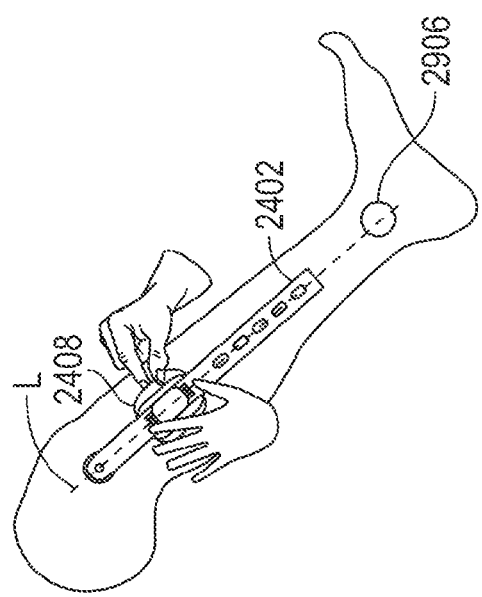

At step 2818, as illustrated in FIG. 29G, the method 2800 may include aligning the longitudinal axis L of the pod targeting template 2402 with the marking for the bony hip joint 2904, such that the longitudinal axis L passes over both the bony knee pivot 2902 and the bony hip joint 2904. Aligning to the bony hip joint 2904 on shorter patients is aided by using the rows of visibility holes 2510. Aligning to the bony hip joint 2904 on taller patients is aided by the triangular tip 2508.

At step 2820, as also illustrated in FIG. 29G, the method may include pressing the anchor pod 2408 into contact with the person's thigh.

At step 2822, as also illustrated in FIG. 29G, the method 2800 may include removing the first pod backing half 2710 by pulling on the first backing tab 2714 and pressing the now-exposed half of the second pod adhesive layer 2709 into contact with the patient's thigh.

At step 2824, the method 2800 may include removing the pod targeting template 2402 from contact with the anchor pod 2408 while leaving the anchor pod 2408 in place on the patient's thigh. Removal may be accomplished by applying force against the pod reception tabs 2514 to release the anchor pod 2408.

At step 2826, the method 2800 may include removing the second pod backing half 2712 by pulling on the second backing tab 2716 and pressing the anchor pod 2408 into contact with the patient's thigh.

At step 2828, the method 2800 may include placing another anchor pod 24 into the into the pod reception hole 2512 of the pod targeting template 2402. The anchor pod 2408 may be held in place using the pod reception tabs 2514.

At step 2830, as illustrated in FIG. 29H, the method 2800 may include aligning the longitudinal axis L of pod targeting template 2402 with the marking for the bony ankle 2906, such that the longitudinal axis L passes over both the bony knee pivot 2902 and the bony ankle 2906. Aligning to the bony ankle 2906 on shorter patients is aided by using the rows of visibility holes 2510. Aligning to the bony ankle 2906 on taller patients is aided by the triangular tip 2508.

At step 2832, the method may include pressing the anchor pod 2408 into contact with the patient's calf.

At step 2834, the method 2800 may include removing the first pod backing half 2710 by pulling on the first backing tab 2714 and pressing the now-exposed half of the second pod adhesive layer 2709 into contact with the patient's calf.

At step 2836, as illustrated in FIG. 29I, the method 2800 may include removing the pod targeting template 2402 from contact with the anchor pod 2408 while leaving the anchor pod 2408 in place on the patient's calf. Removal may be accomplished by applying force against the pod reception tabs 2514 to release the anchor pod 2408.

At step 2838, the method 2800 may include removing the second pod backing half 2712 by pulling on the second backing tab 2716 and pressing the anchor pod 2408 into contact with the patient's calf.

At step 2840, the method 2800 may include removing the knee pivot anchor 2406 from the pod targeting template 2402. Removal may be accomplished by applying force against the anchor tabs 2606 to allow the anchor tabs to slide through the knee pivot hole 2506.

At step 2842, the method 2800 may include removing the knee pivot anchor 2406 from the person's knee. This may be accomplished by gently peeling the knee pivot anchor 2406 away from the person's knee.

Figure 29J:
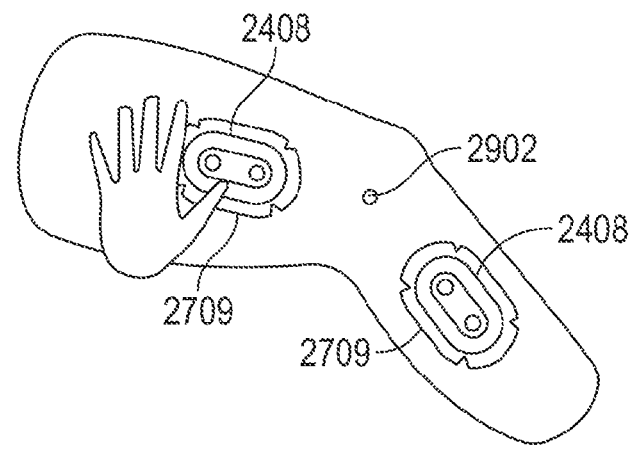
Figure 29K:
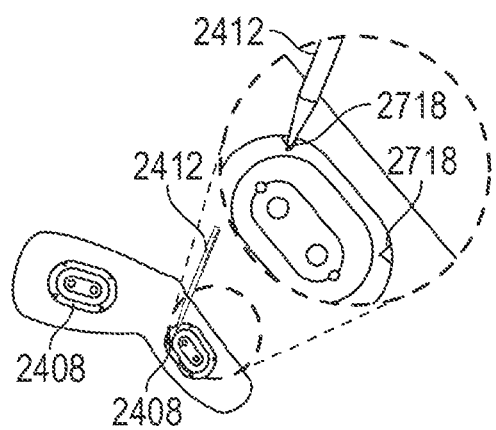

At step 2844, as illustrated in FIG. 29J, the method 2800 may include flattening the second pod adhesive layer 2709 of each of the anchor pods 2408 and rubbing gently to ensure full adhesion with the person's leg.

At step 2846, as illustrated in FIG. 29I<, the method 2800 may include marking the skin about the notches 2718. The marking may be accomplished with a pen or other writing utensil, such as the surgical marker 2412. Making the marking with the surgical marker 2412 will ensure that, should the patient bathe before reapplying the anchor pods 2408, the markings remain visible.

Figure 29L:
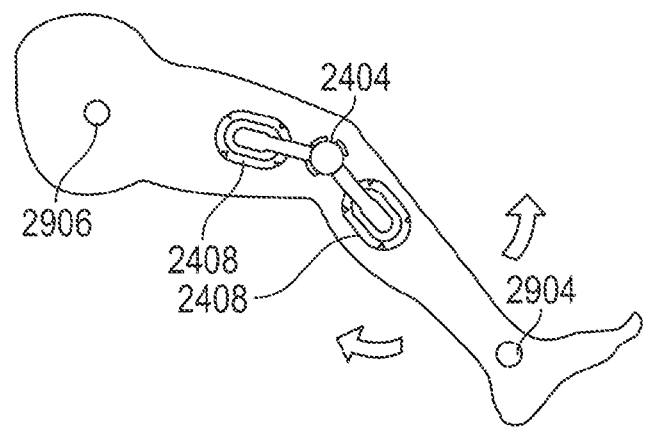

At step 2848, as illustrated in FIG. 29L, the method 2800 may include attaching the goniometer 2404 to the anchor pods 2408. The goniometer 2404 may be attached by allowing the goniometer arm magnets or ferromagnetic material in the goniometer arms 2416, 2420 to come close to the anchor pod magnets and allowing the goniometer arms 2416, 2420 and the anchor pods 2408 to snap together.

Embodiments of the method 2800 is not limited to the steps disclosed and may contain more or fewer steps than those disclosed. Certain steps may be omitted (e.g., step 2840 may be skipped entirely and the knee pivot anchor 2406 may be removed from the patient's knee while still attached to the pod targeting template 2402). The steps may be performed in any suitable order (e.g., steps 2818-2826 placing one of the anchor pods 2408 onto the person's thigh may be performed before or after steps 2830-2838, but step 2804 marking the bony knee pivot 2902 may not be performed after step 2816 placing the knee pivot anchor 2406 into contact with the bony knee pivot 2902).

Figure 30A:
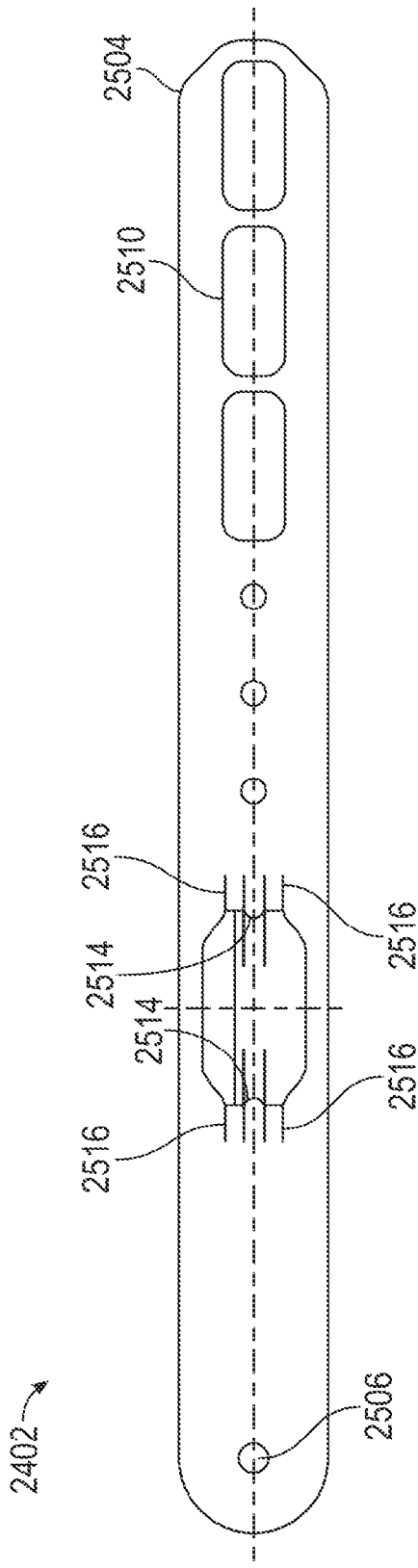
FIGS. 30A and 30B illustrate top views of alternative embodiments of the pod targeting template of FIG. 25 in accordance with aspects of the present disclosure.
Figure 30B:
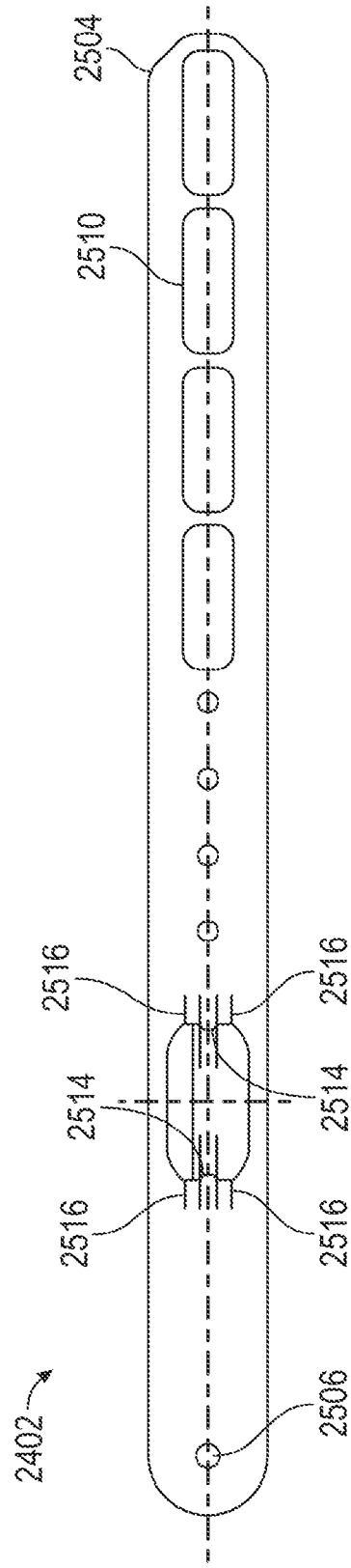

FIGS. 30A and 30B illustrate top views of alternative embodiments of the pod targeting template 2402. As previously noted, the pod targeting template 2402 may include a single row of visibility holes 2510. The pod targeting template 2402 may vary in length. These versions of the pod targeting template 2402 can be used in the same or similar manner as the other versions described herein.

Figure 31:
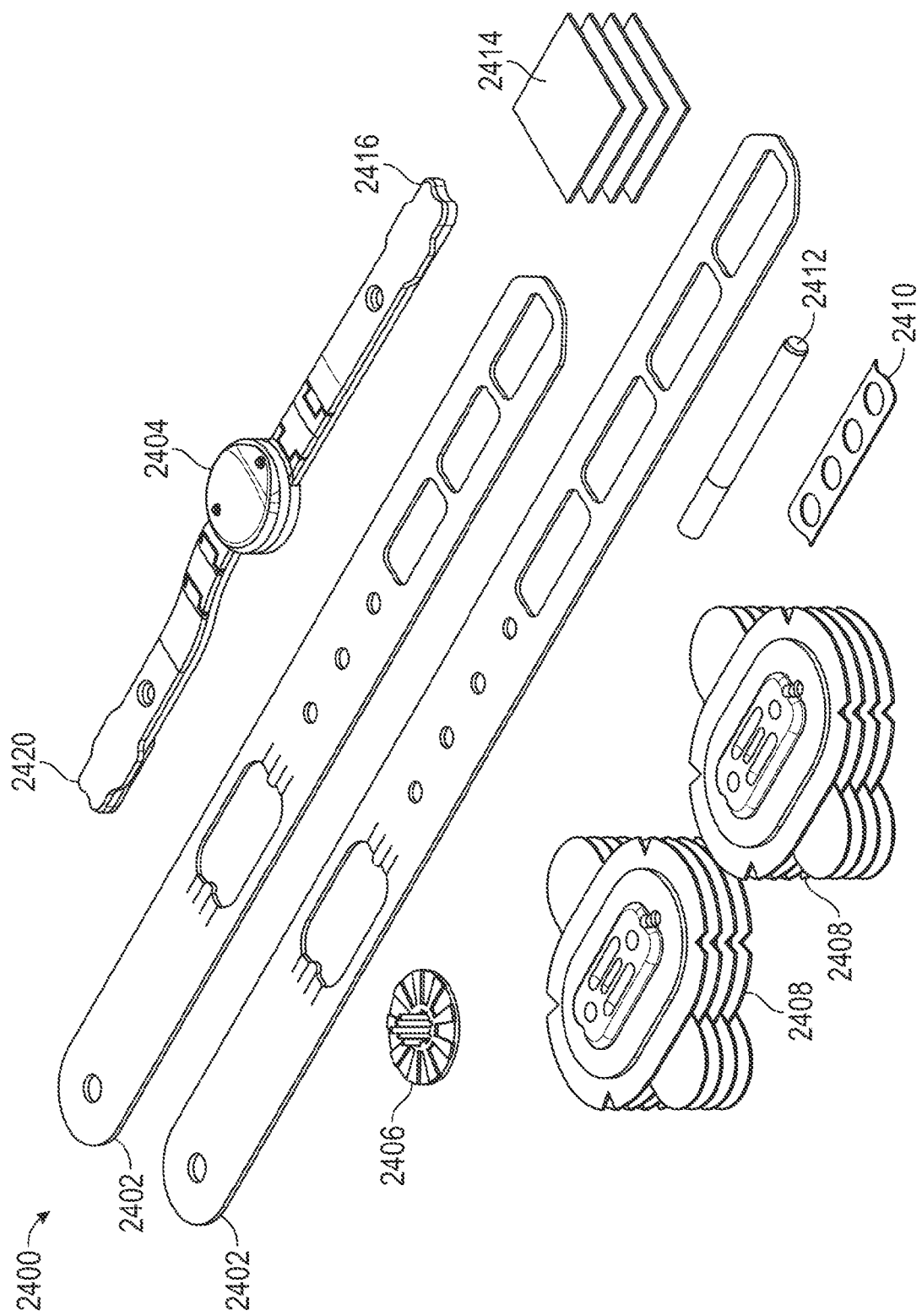
FIG. 31 illustrates a top perspective view of an alternative embodiment of the system of FIG. 24 in accordance with aspects of the present disclosure.

FIG. 31 illustrates an alternative embodiment of the system 2400 having eight anchor pods 2408 and two pod targeting templates 2402. The two pod targeting templates 2402 have different lengths, and can be used in the same or similar manner as the other versions described herein.

Figure 32:
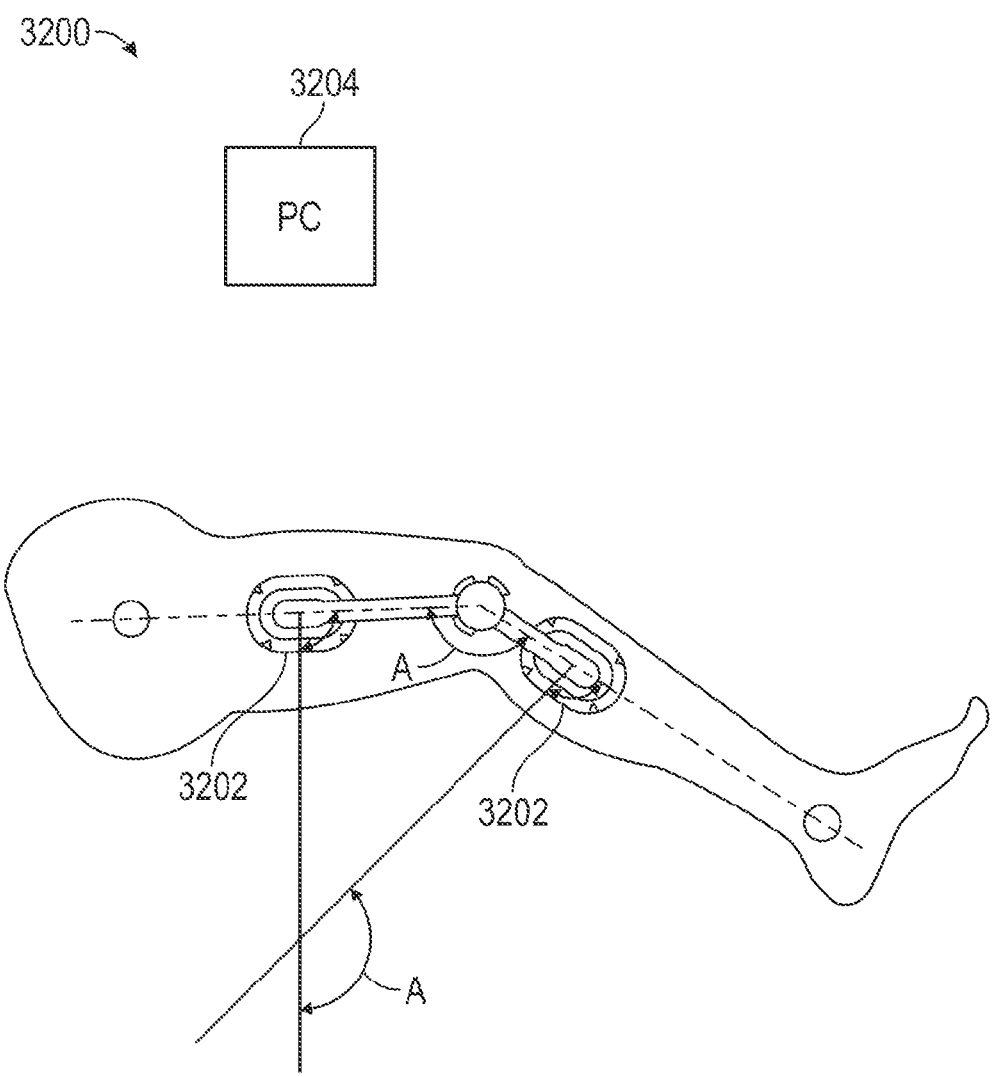
FIG. 32 illustrates a system for using accelerometer pods for determining joint motion in accordance with aspects of the present disclosure.

FIG. 32 illustrates a system 3200 for determining an angle A of a joint of a user. The system may include two accelerometer pods 3202 containing accelerometers. As shown, one of the accelerometer pods 3202 is placed on the upper leg of a user, while the other accelerometer pod 3202 is placed on the lower leg of the user. In some embodiments, one or both of the accelerometer pods 3202 may contain a wireless network device (e.g., a Bluetooth device). In some embodiments, the accelerometer pods 3202 may be in wireless communication with one another by way of respective wireless network devices. In some embodiments, one or both of the accelerometer pods 3202 may be in communication with a remote computing device 3204 by way of respective wireless network devices. The accelerometers may be used to determine the orientation of the accelerometer pods 3202 relative to gravity, transmit the orientation to each-other or to the remote computing device 3204, allowing for determination of angle A of the user's joint.

The accelerometer pods 3202 may be attached in the same manner and using the same methods as are used with the anchor pods 2402 as discussed previously in the present disclosure. The accelerometer pods 3202 may be placed in proximity to the legs using a band, such as an elastic thigh band or calf band. Using accelerometer pods 3202 may allow for reduced complexity and size.

The accelerometer pods 3202 may include one or more memory devices in communication with the accelerometers. In some embodiments, the one or more memory devices may be in communication with the wireless network devices. The memory devices may be used for storing orientation information to later be transmitted to the remote computing device 3204. In some embodiments, the accelerometer devices 3202 may include batteries for powering the various subcomponents.

Figure 33A:
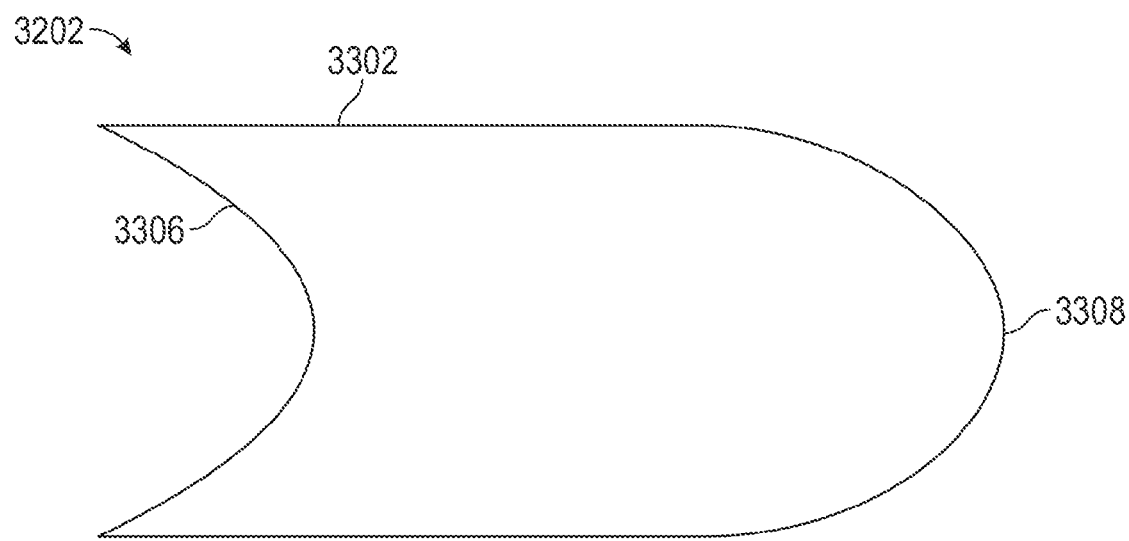
FIGS. 33A-33C illustrate various views of an accelerometer pod in accordance with aspects of the present disclosure.
Figure 33B:
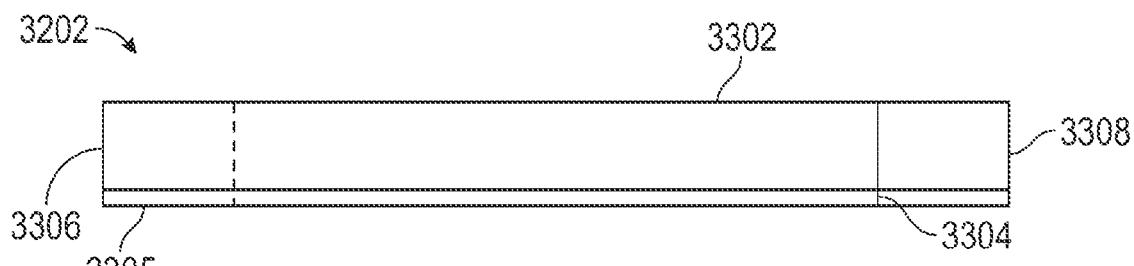
Figure 33C:
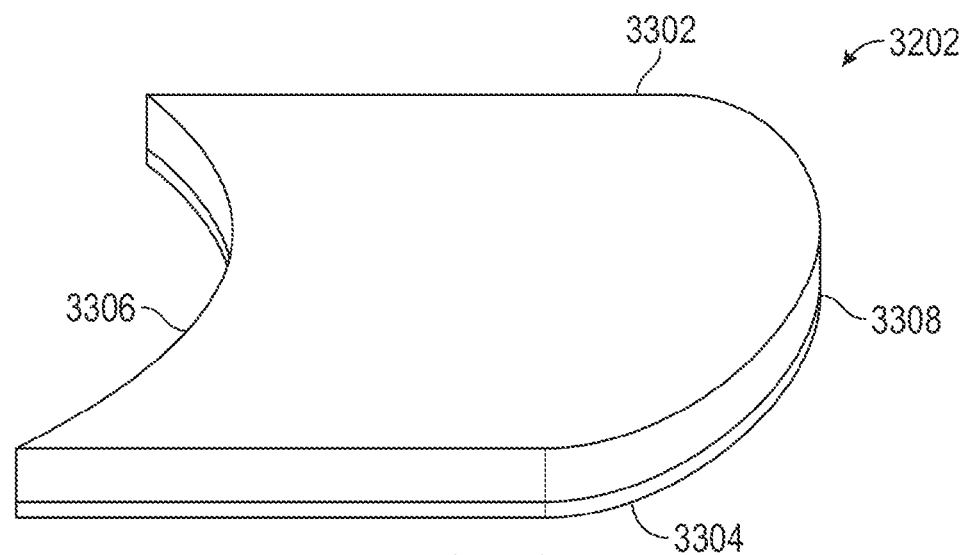

As illustrated in FIGS. 33-34, the accelerometer pod 3202 may have a body portion 3302 and an adhesive portion 3304. A release liner 3305 may be removed from the adhesive portion 3304 to expose the adhesive to secure the body portion 3302 to the user. The accelerometer pod 3202 may further include a first end 3306 and a second end 3308 formed such that the first end 3306 of a first accelerometer pod 3402*a*, 3402*b* can engage with the second end 3304 of a second accelerometer pod 3402*c*, 3402*d*. For example, as illustrated in FIGS. 33-34, the first end 3306 may be formed to be concave, and the second end 3308 may be formed to be convex, such that the first end 3306 of the first accelerometer pod 3202a, 3402b can engage the second end 3308 of the second accelerometer pod 3402c, 3402d without substantial gaps. In other words, the first and second ends 3306, 3308 can be complementary in shape to each other such that they can closely nest or mate together. Other shapes can be used for the first end 3306 and the second end 3308 (e.g., zig-zagging or wave-shaped ends), while still allowing the first ends 3306 of the first accelerometer pods 3402 to engage the second ends 3308 of the second accelerometer pods 3406 without any substantial gaps therebetween.

Figure 34A:
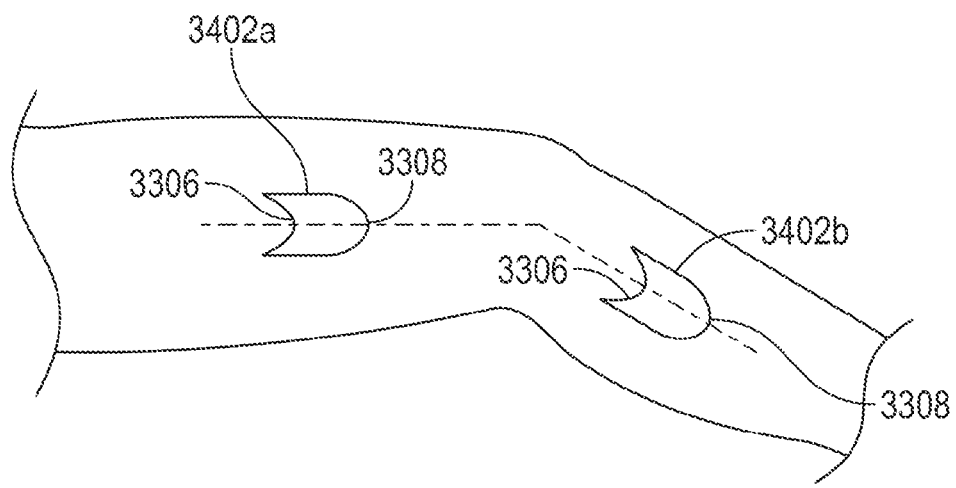
FIGS. 34A-34C illustrate placement and replacement of accelerometer pods in accordance with aspects of the present disclosure.

FIG. 34A illustrates two first accelerometer pods 3402a, 3402b initially attached to the thigh and the calf, respectively. These may be attached as previously described relative to the anchor pods 2408.

Figure 34B:
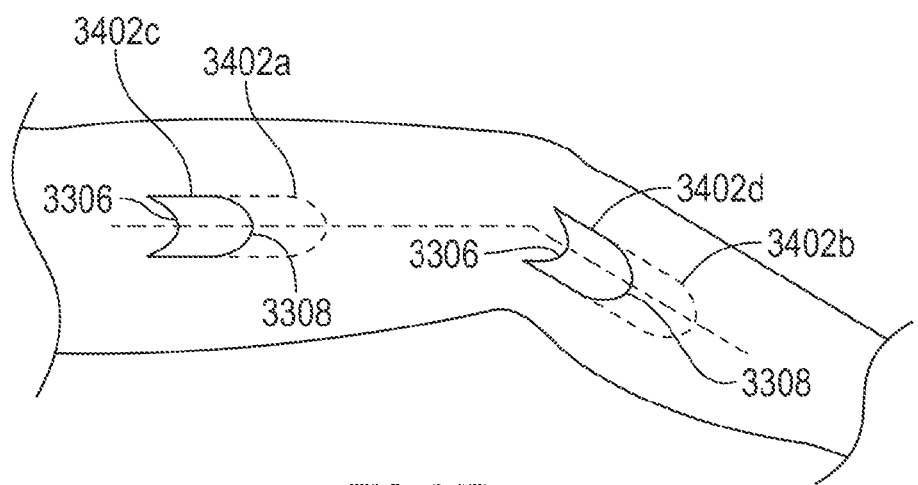

FIG. 34B illustrates two second accelerometer pods 3402c, 3402d attached to the thigh and the calf, respectively. Just before removing the two first accelerometer pods 3402a, 3402b, the two second accelerometer pods 3402c, 3402d (identical to the two first accelerometer pods 3402a, 3402b) are placed so as to be engaged with the respective two first accelerometer pods 3402a, 3402b, such that the first ends 3306 of the two first accelerometer pods 3402a, 3402b engage the second ends 3308 of the second accelerometer pods 3402c, 3402d without any substantial gaps therebetween (e.g., they can abut each other). As such, a user can, without professional help, place the second accelerometer pods 3402c, 3402d while maintaining the alignment of the initially installed first accelerometer pods 3402a, 3402b. The user may then remove the first accelerometer pods 3402a, 3402b to allow the user's skin that was beneath them to breathe and avoid maceration.

Figure 34C:
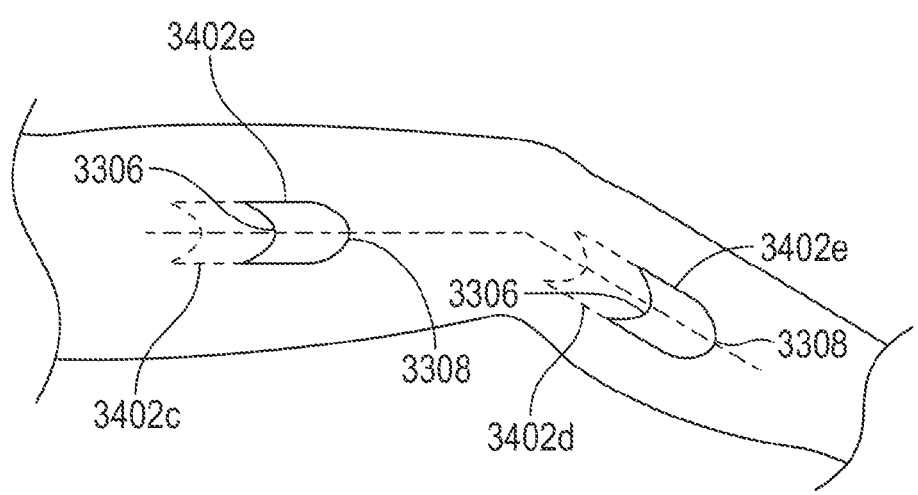

FIG. 34C illustrates two third accelerometer pods 3402e, 3402f (identical to the two first accelerometer pods 3402a, 3402b and the second accelerometer pods 3402c, 3402d) attached to the thigh and calf, respectively. The two third accelerometer pods 3402e, 3402f are placed so as to be engaged with the respective two second accelerometer pods 3402c, 3402d, such that the first ends 3306 of the two third accelerometer pods 3402e, 3402f engage the second ends 3308 of the second accelerometer pods 3402c, 3402d without any substantial gaps therebetween (e.g., again, they can abut each other). The user may then remove the second accelerometer pods 3402c, 3402d to allow the user's skin that was beneath them to breathe and avoid maceration. This replacement technique and method for the pods 3402a, 3402b, 3402c, 3402d, 3402e, 3402f can be repeated as needed.

Consistent with the above disclosure, the examples of assemblies enumerated in the following clauses are specifically contemplated and are intended as a non-limiting set of examples.

Clause 1. A method of installing devices on a user, the method comprising:
 (a) locating a lateral epicondyle at a knee of the user and indicating same to define a knee indicator;
 (b) installing a knee pivot anchor at the knee indicator;
 (c) locating a greater trochanter at a hip of the user and indicating same to define a hip indicator;
 (d) locating a lateral malleolus at an ankle of the user and indicating same to define an ankle indicator;
 (e) mounting a proximal portion of a template to the knee pivot anchor, pivoting the template about the knee pivot anchor, and aligning a distal portion of the template with the hip dot;
 (f) placing a first pod in an aperture of the template and, with the distal portion of the template aligned with the hip dot, securing the first pod to a proximal location on the user;
 (g) pivoting the template about the knee pivot anchor and aligning the distal portion of the template with the ankle dot;
 (f) placing a second pod in the aperture of the template and, with the distal portion of the template aligned with the ankle dot, securing the second pod to a distal location on the user; and
 (g) removing the template and the knee pivot anchor from the user.

Clause 2. The method of clause 1 further comprising mounting a goniometer to the user such that a proximal portion of the goniometer is mounted to the first pod, a distal portion of the goniometer is mounted to the second pod, and a center pivot of the goniometer substantially aligns with the knee dot.

Clause 3. The method of any preceding clause, further comprising placing a third pod aligned and in engagement with the first pod.

Clause 4. The method of any preceding clause, further comprising removing the first pod.

Clause 5. The method of any preceding clause, wherein at least one of the first pod or the second pod contains an accelerometer.

Clause 6. The method of any preceding clause, wherein at least one of the first pod or the second pod contains a wireless network device.

Clause 7. The method of any preceding clause further comprising mounting a goniometer to a brace and mounting the brace to the user, such that a proximal portion of the goniometer is mounted to the first pod, a distal portion of the goniometer is mounted to the second pod, and a center pivot of the goniometer substantially aligns with the knee dot.

Clause 8. The method of any preceding clause further comprising replacing the first and second pods by:
 locating notches in each of the first and second pods and marking first and second notch locations, respectively, on the user;
 removing the first and second pods from the user;
 installing a third pod on the user by aligning notches in the third pod with the first notch locations on the user; and
 installing a fourth pod on the user by aligning notches in the fourth pod with the second notch locations on the user.

Clause 9. The method of any preceding clause wherein:
 step (a) comprises marking the knee such that the knee indicator comprises a knee mark;
 step (c) comprises marking the hip such that the hip indicator comprises a hip mark; and
 step (d) comprises marking the ankle such that the ankle indicator comprises an ankle mark.

Clause 10. The method of any preceding clause wherein:
 step (a) comprises placing a first adhesive pad on the knee such that the knee indicator comprises a knee dot;
 step (c) comprises placing a second adhesive pad on the hip such that the hip indicator comprises a hip dot; and
 step (d) comprises placing a third adhesive pad on the ankle such that the ankle indicator comprises an ankle dot.

Clause 11. A kit for installing devices on a user, the kit comprising:
- an indicator set comprising a marker configured to place markings on the user, and a set of adhesive pads configured to be placed on the user;
- a knee pivot anchor configured to be attached to the user;
- a template having a proximal portion configured to be pivotally mounted to the knee pivot anchor, a distal portion configured to be positioned at different locations on the user, and an aperture;
- a set of pods configured to be interchangeably located in the aperture of the template, and each pod is configured to be secured to respective locations on the user; and
- the template and the knee pivot anchor are configured to be removed from the user with the pods remaining in place on the user.

Clause 12. The kit of any preceding clause, further comprising a goniometer configured to be removably mounted to the pods on the user.

Clause 13. The kit of any preceding clause, further comprising cleaning wipes configured to clean portions of the user prior to using other components of the kit.

Clause 14. The kit of any preceding clause, wherein the knee pivot anchor is configured to be removably bonded to the user.

Clause 15. The kit of any preceding clause, wherein the pods each further comprise:
- a first end and a second end disposed opposite one-another, the first end and the second end being shaped such that the first end of a first pod may engage the second end of the a second pod without any substantial gaps therebetween.

Clause 16. The kit of any preceding clause, wherein the first end has a concave shape and the second end has a convex shape.

Clause 17. The kit of any preceding clause, wherein at least one of the pods contains a battery.

Clause 18. The kit of any preceding clause, wherein at least one of the pods contains an accelerometer.

Clause 19. The kit of any preceding clause, wherein at least one of the pods contains a wireless network device.

Clause 20. The kit of any preceding clause, wherein at least one of the pods includes an adhesive portion.

Clause 21. A knee brace for supporting a knee of a patient, the knee brace comprising:
- a first hinge having a first calf post configured to be attached to a calf of the patient, and a first thigh post configured to be attached to a thigh of the patient, wherein the first thigh post is pivotable relative to the first calf post; and
- an electronic device coupled to the first hinge.

Clause 22. The knee brace of any preceding clause wherein the electronic device comprises a goniometer.

Clause 23. The knee brace of any preceding clause wherein the first hinge further comprises a magnet that is coupled to one of the first calf post and the first thigh post; and
- the goniometer is coupled to the other of the first calf post and the first thigh post, and the goniometer further comprises a sensor for detecting a position of the magnet.

Clause 24. The knee brace of any preceding clause wherein the first hinge further comprises a hub, and the goniometer is disposed within the hub.

Clause 25. The knee brace of any preceding clause wherein the first calf post is connected to a calf strap and the first thigh post is connected to a thigh strap.

Clause 26. The knee brace of any preceding clause wherein the calf strap further comprises a set of features selected from a group consisting of holes, apertures, and indentations; and
- wherein the features are configured to allow for markings to be applied to the calf of the patient such that the markings can be lined up with the features during reapplication of the knee brace.

Clause 27. The knee brace of any preceding clause wherein the thigh strap further comprises a set of features selected from a group consisting of holes, apertures, and indentations; and
- wherein the features are configured to allow for markings to be applied to the thigh of the patient such that the markings can be lined up with the features during reapplication of the knee brace.

Clause 28. The knee brace of any preceding clause wherein the first hinge is configured to have a selectable range of motion.

Clause 29. The knee brace of any preceding clause further comprising a second hinge having a second calf post configured to attach to the calf of the patient, a second thigh post configured to be attached to the thigh of the patient, and the second thigh post is pivotable relative to the first calf post.

Clause 30. The knee brace of any preceding clause wherein the first hinge is a lateral hinge, the first calf post is a lateral calf post, the first thigh post is a lateral thigh post, the second hinge is a medial hinge, the second calf post is a medial calf post, and the second thigh post is a medial thigh post.

Clause 31. The knee brace of any preceding clause further comprising a washer disposed between the first calf post and the first thigh post.

Clause 32. The knee brace of any preceding clause wherein the electronic device comprises a pedometer.

Clause 33. The knee brace of any preceding clause wherein one of the first calf post and the first thigh post is connected to a knee pad configured to contact a side of the knee of the patient.

Clause 34. A knee brace for supporting a knee of a patient, the knee brace comprising
- a first hinge having a first calf post configured to attach to a calf of the patient, a first thigh post configured to attach to a thigh of the patient, and the first thigh post is pivotable relative to the first calf post; and
- a hub containing an electronic device and coupled to one of the first calf post and the first thigh post;
- a second hinge having a second calf post configured to attach to the calf of the patient, a second thigh post configured to attach to the thigh of the patient, and the second thigh post is pivotable relative to the first calf post.

Clause 35. The knee brace of any preceding clause wherein the electronic device comprises a goniometer.

Clause 36. The knee brace of any preceding clause wherein the first hinge further comprises a magnet coupled to one of the first calf post and the first thigh post; and
- the goniometer is coupled to the other of the first calf post and the first thigh post, and the goniometer further comprises a sensor for detecting a position of the magnet.

Clause 37. The knee brace of any preceding clause wherein the first hinge is configured to have a selectable range of motion.

Clause 38. The knee brace of any preceding clause wherein the first calf post is connected to a calf strap and the first thigh post is connected to a thigh strap.

Clause 39. The knee brace of any preceding clause wherein the calf strap further comprises a set of features selected from a group consisting of holes, apertures, and indentations; and
    wherein the features are configured to allow for markings to be applied to the calf of the patient such that the markings can be lined up with the features during reapplication of the knee brace.

Clause 40. The knee brace of any preceding clause wherein the thigh strap further comprises a set of features selected from a group consisting of holes, apertures, and indentations; and
    wherein the features are configured to allow for markings to be applied to the thigh of the patient such that the markings can be lined up with the features during reapplication of the knee brace.

Clause 41. The knee brace of any preceding clause further comprising:
    a first washer disposed between the first calf post and the first thigh post; and
    a second washer disposed between the second calf post and the second thigh post.

Clause 42. The knee brace of any preceding clause wherein the first hinge is a lateral hinge, the first calf post is a lateral calf post, the first thigh post is a lateral thigh post, the second hinge is a medial hinge, the second calf post is a medial calf post, and the second thigh post is a medial thigh post.

Clause 43. The knee brace of any preceding clause wherein one of the first calf post and the first thigh post is connected to a knee pad for contacting a side of the knee of the patient.

Clause 44. The knee brace of any preceding clause wherein the electronic device is a pedometer.

Clause 45. A knee brace for supporting a knee of a patient, the knee brace comprising
    a first hinge comprising:
    a first calf post configured to attach to a calf of the patient;
    a first thigh post pivotable relative to the first calf post and configured to attach to a thigh of the patient;
    a first washer disposed between the first calf post and the first thigh post;
    a magnet coupled to one of the first calf post and the first thigh post; and
    a hub having a goniometer and coupled to one of the first calf post and the first thigh post, wherein the goniometer rotates separately from the magnet and comprises a sensor configured to detect motion of the magnet; and
    a second hinge comprising:
    a second calf post configured to attach to the calf of the patient;
    a second thigh post configured to attach to the thigh of the patient, and the second thigh post is pivotable relative to the first calf post; and
    a second washer disposed between the second calf post and the second thigh post.

Clause 46. The knee brace of any preceding clause wherein the first calf post is connected to a calf strap and the first thigh post is connected to a thigh strap;
    wherein the calf strap further comprises a set of features selected from a group consisting of holes, apertures, and indentations;
    wherein the features are configured to allow for markings to be applied to the calf of the patient such that the markings can be lined up with the features during reapplication of the knee brace.

Clause 47. The knee brace of any preceding clause wherein the first calf post is connected to a calf strap and the first thigh post is connected to a thigh strap;
    wherein the thigh strap further comprises a set of features selected from a group consisting of holes, apertures, and indentations; and
    wherein the features are configured to allow for markings to be applied to the thigh of the patient such that the markings can be lined up with the features during reapplication of the knee brace.

Clause 48. An elbow brace for supporting an elbow of a patient, the elbow brace comprising:
    a first hinge having a first forearm post configured to attach to a forearm of the patient, a first upper arm post configured to attach to an upper arm of the patient, and the first upper arm post is pivotable relative to the first forearm post; and
    an electronic device coupled to the first hinge.

Clause 49. The elbow brace of any preceding clause wherein the first forearm post is connected to a forearm strap and the first upper arm post is connected to an upper arm strap.

Clause 50. The elbow brace of any preceding clause wherein the upper arm strap further comprises a set of features selected from a group consisting of holes, apertures, and indentations; and
    wherein the features are configured to allow for markings to be applied to the upper arm of the patient such that the markings can be lined up with the features during reapplication of the elbow brace.

Clause 51. The elbow brace of any preceding clause wherein the forearm strap further comprises a set of features selected from a group consisting of holes, apertures, and indentations; and
    wherein the features are configured to allow for markings to be applied to the forearm of the patient such that the markings can be lined up with the features during reapplication of the elbow brace.

Clause 52. A joint brace of any preceding clause for supporting a bendable joint of a patient, the joint brace comprising:
    a first hinge having a first inferior joint post configured to attach to an inferior joint of the patient, a first superior joint post configured to attach to a superior joint of the patient, and the first superior joint post is pivotable relative to the first inferior joint post; and
    an electronic device coupled to the first hinge.

Clause 53. The joint brace of any preceding clause wherein the first inferior joint post is connected to an inferior joint strap and the first superior joint post is connected to a superior joint strap.

Clause 54. The joint brace of any preceding clause wherein the inferior joint strap further comprises a set of features selected from a group consisting of holes, apertures, and indentations; and
    wherein the features are configured to allow for markings to be applied to the inferior joint of the patient such that the markings can be lined up with the features during reapplication of the joint brace.

Clause 55. The joint brace of any preceding clause wherein the superior joint strap further comprises a set of features selected from a group consisting of holes, apertures, and indentations; and
    wherein the features are configured to allow for markings to be applied to the superior joint of the patient such that the markings can be lined up with the features during reapplication of the joint brace.

Benefits, other advantages, and solutions to problems have been described above with regard to specific embodiments. However, the benefits, advantages, solutions to problems, and any feature(s) that can cause any benefit, advantage, or solution to occur or become more pronounced are not to be construed as a critical, required, sacrosanct or essential feature of any or all the claims.

After reading the specification, skilled artisans will appreciate that certain features which, for clarity, are described herein in the context of separate embodiments, can also be provided in combination in a single embodiment. Conversely, various features that are, for brevity, described in the context of a single embodiment, can also be provided separately or in any subcombination. Further, references to values stated in ranges include each and every possible value within that range.

Consistent with the above disclosure, the examples of assemblies enumerated in the following clauses are specifically contemplated and are intended as a non-limiting set of examples.

What is claimed is:

1. A method of installing devices on a user, the method comprising:
   (a) locating a lateral epicondyle at a knee of the user and indicating same to define a knee indicator;
   (b) installing a knee pivot anchor at the knee indicator;
   (c) locating a greater trochanter at a hip of the user and indicating same to define a hip indicator;
   (d) locating a lateral malleolus at an ankle of the user and indicating same to define an ankle indicator;
   (e) mounting a proximal portion of a template to the knee pivot anchor, pivoting the template about the knee pivot anchor, and aligning a distal portion of the template with a hip dot;
   (f) placing a first pod in an aperture of the template and, with the distal portion of the template aligned with the hip dot, securing the first pod to a proximal location on the user;
   (g) pivoting the template about the knee pivot anchor and aligning the distal portion of the template with an ankle dot;
   (f) placing a second pod in the aperture of the template and, with the distal portion of the template aligned with the ankle dot, securing the second pod to a distal location on the user; and
   (g) removing the template and the knee pivot anchor from the user.

2. The method of claim 1, further comprising mounting a goniometer to the user such that a proximal portion of the goniometer is mounted to the first pod, a distal portion of the goniometer is mounted to the second pod, and a center pivot of the goniometer substantially aligns with a knee dot.

3. The method of claim 1, further comprising mounting a goniometer to a brace and mounting the brace to the user, such that a proximal portion of the goniometer is mounted to the first pod, a distal portion of the goniometer is mounted to the second pod, and a center pivot of the goniometer substantially aligns with a knee dot.

4. The method of claim 1, further comprising replacing the first and second pods by:
   locating notches in each of the first and second pods and marking first and second notch locations, respectively, on the user;
   removing the first and second pods from the user;
   installing a third pod on the user by aligning notches in the third pod with the first notch locations on the user; and
   installing a fourth pod on the user by aligning notches in the fourth pod with the second notch locations on the user.

5. The method of claim 1, wherein:
   step (a) comprises marking the knee such that the knee indicator comprises a knee mark;
   step (c) comprises marking the hip such that the hip indicator comprises a hip mark; and
   step (d) comprises marking the ankle such that the ankle indicator comprises an ankle mark.

6. The method of claim 1, wherein:
   step (a) comprises placing a first adhesive pad on the knee such that the knee indicator comprises a knee dot;
   step (c) comprises placing a second adhesive pad on the hip such that the hip indicator comprises the hip dot; and
   step (d) comprises placing a third adhesive pad on the ankle such that the ankle indicator comprises the ankle dot.

7. The method of claim 1, further comprising placing a third pod aligned and in engagement with the first pod.

8. The method of claim 7, further comprising removing the first pod.

9. The method of claim 1, wherein at least one of the first pod or the second pod contains an accelerometer.

10. The method of claim 1, wherein at least one of the first pod or the second pod contains a wireless network device.

11. A kit for installing devices on a user, the kit comprising:
    an indicator set comprising a marker configured to place markings on the user, and a set of adhesive pads configured to be placed on the user;
    a knee pivot anchor configured to be attached to the user;
    a template having a proximal portion configured to be pivotally mounted to the knee pivot anchor, a distal portion configured to be positioned at different locations on the user, and an aperture;
    a set of pods configured to be interchangeably located in the aperture of the template, and each pod is configured to be secured to respective locations on the user; and
    the template and the knee pivot anchor are configured to be removed from the user with the pods remaining in place on the user.

12. The kit of claim 11, further comprising a goniometer configured to be removably mounted to the pods on the user.

13. The kit of claim 11, further comprising cleaning wipes configured to clean portions of the user prior to using other components of the kit.

14. The kit of claim 11, wherein the knee pivot anchor is configured to be removably bonded to the user.

15. The kit of claim 11, wherein the pods each further comprise:
    a first end and a second end disposed opposite one-another, the first end and the second end being shaped such that the first end of a first pod may engage the second end of a second pod without any substantial gaps therebetween.

16. The kit of claim 11, wherein the first end has a concave shape and the second end has a convex shape.

17. The kit of claim 11, wherein at least one of the pods contains a battery.

18. The kit of claim 11, wherein at least one of the pods contains an accelerometer.

19. The kit of claim 11, wherein at least one of the pods contains a wireless network device.

20. The kit of claim 11, wherein at least one of the pods includes an adhesive portion.

\* \* \* \* \*